(12) United States Patent
Soukka et al.

(10) Patent No.: US 8,993,246 B2
(45) Date of Patent: Mar. 31, 2015

(54) LUMINESCENCE ASSAY METHOD

(75) Inventors: Tero Soukka, Turku (FI); Urpo Lamminmaki, Vanhalinna (FI)

(73) Assignee: Oy Arctic Partners AB, Turku (FI)

( * ) Notice: Subject to any disclaimer, the term of this patent is extended or adjusted under 35 U.S.C. 154(b) by 0 days.

(21) Appl. No.: 13/257,595

(22) PCT Filed: Mar. 23, 2010

(86) PCT No.: PCT/FI2010/050222
§ 371 (c)(1),
(2), (4) Date: Sep. 19, 2011

(87) PCT Pub. No.: WO2010/109065
PCT Pub. Date: Sep. 30, 2010

(65) Prior Publication Data
US 2012/0009566 A1    Jan. 12, 2012

Related U.S. Application Data

(60) Provisional application No. 61/162,752, filed on Mar. 24, 2009.

(30) Foreign Application Priority Data

Mar. 24, 2009  (FI) ...................................... 20095302

(51) Int. Cl.
*G01N 33/53* (2006.01)
*G01N 33/536* (2006.01)
(Continued)

(52) U.S. Cl.
CPC ............ *G01N 33/542* (2013.01); *C12Q 1/6818* (2013.01); *G01N 33/582* (2013.01)
USPC .............. 435/7.1; 436/537; 436/540; 436/81; 436/172

(58) Field of Classification Search
CPC ........... C12Q 1/6818; C12Q 2563/137; G01N 33/542; G01N 33/582
See application file for complete search history.

(56) References Cited

U.S. PATENT DOCUMENTS 5,760,191 A * 6/1998 Snow et al. ..................... 534/10
5,827,653 A   10/1998 Sammes et al. .................. 435/6
(Continued)

FOREIGN PATENT DOCUMENTS

JP    2004-000213    1/2004
WO    WO 95/08642    3/1995

OTHER PUBLICATIONS

Coates et al. Enhancement of luminescence of europium (III) ions in water by use of synergistic chelation. Part 1.1: 1 and 2:1 complexex. J. Chem. Soc. Perkin Trans 1996, vol. 2, pp. 1275-1282.*
(Continued)

*Primary Examiner* — Shafiqul Haq
(74) *Attorney, Agent, or Firm* — James C. Lydon

(57) ABSTRACT

A bioassay employing a first group including a lanthanide ion carrier chelate and a first recognition element, a second group including an antenna ligand and a second recognition element; where the lanthanide ion carrier chelate binds strongly to lanthanide, or the lanthanide ion carrier chelate binds moderately to lanthanide, and an agent complexing the lanthanide ion is additionally employed at a concentration of at least 1 pmol/l. The antenna ligand binds weakly to the lanthanide ion. Analyte recognition by the first recognition element and by the second recognition element results in either chelate complementation and increased fluorescence, or chelate dis-complementation and decreased fluorescence.

14 Claims, 25 Drawing Sheets

(51) Int. Cl.
| | |
|---|---|
| G01N 33/24 | (2006.01) |
| G01N 21/76 | (2006.01) |
| G01N 33/542 | (2006.01) |
| C12Q 1/68 | (2006.01) |
| G01N 33/58 | (2006.01) |

(56) References Cited

U.S. PATENT DOCUMENTS

| | | | |
|---|---|---|---|
| 6,242,268 B1 | 6/2001 | Wieder et al. | 436/538 |
| 6,565,828 B2 * | 5/2003 | Liu | 424/1.53 |

OTHER PUBLICATIONS

Kitamura et al., "Template-directed Formation of Luminescent Lanthanide Complexes: Versatile Tools for Colorimetric Identification of Single Nucleotide Polymorphism," 102 *J. Inorganic Biochemistry* 1921 (2008).

Bunzli et al., "Taking Advantage of Luminescent Lanthanide Ions," 34 *Chem.Soc.Rev.* 1048 (2005).

Karhunen et al., "Luminescent Switching by Hybridization-directed Mixed Lanthanide Complex Formation," 82 *Anal. Chem.* 751 (2010).

Takalo et al., "Synthesis of Europium(III) Chelates Suitable for Labeling of Bioactive Molecules," 5 *Bioconjugate Chem.* 278 (1994).

Mukkala et al., "The Synthesis and Use of Activated N-Benzyl Derivatives of Diethylenetriaminetetraacetic Acids: Alternative Reagents for Labeling of Antibodies With Metal Ions," 176 *Anal. Biochem.* 319 (1989).

Wang et al., "Homogeneous Time-resolved Fluorescence DNA Hybridization Assay by DNA-mediated Formation of an EDTA-EU(III)-β-Diketone Ternary Complex," 299 *Anal.Biochem.* 169 (2001).

Yuan et al., "Lanthanide-based Luminescence Probes and Time-resolved Luminescence Bioassays," 25 *Trends in Anal.Chem.* 490 (2006).

Kitamura et al., "Colorimetric Allele Analysis Based on the DNA-directed Cooperative Formation of Luminous Lanthanide Complexes," 50 *Nucleic Acids Symposium Series* 105 (2006).

Soukka et al., "Photon Upconversion in Homogeneous Fluorescence-based Bioanalytical Assays," 1130 *Annals NY Acad. Sci.* 188 (2008).

* cited by examiner

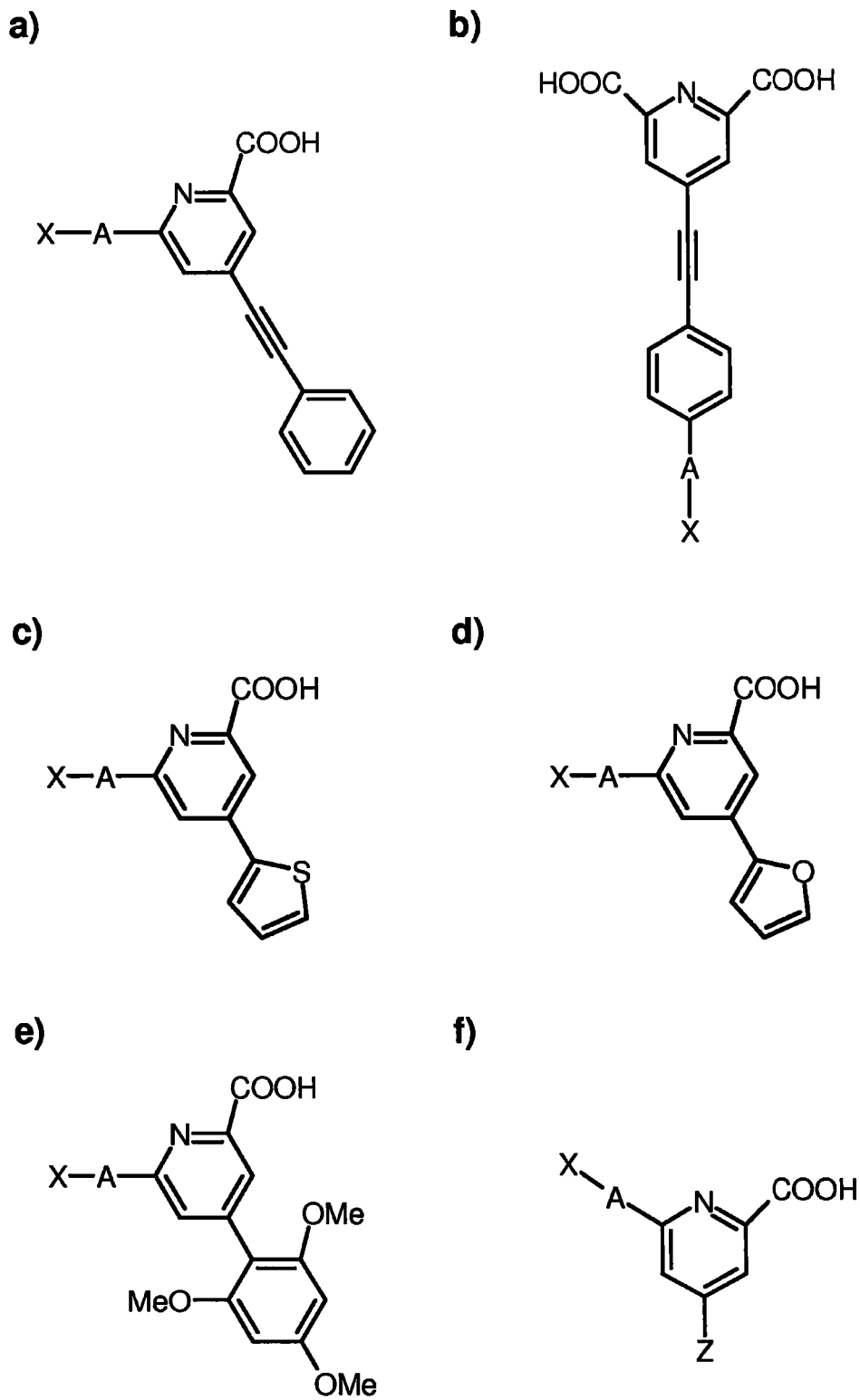
Figure 5/i

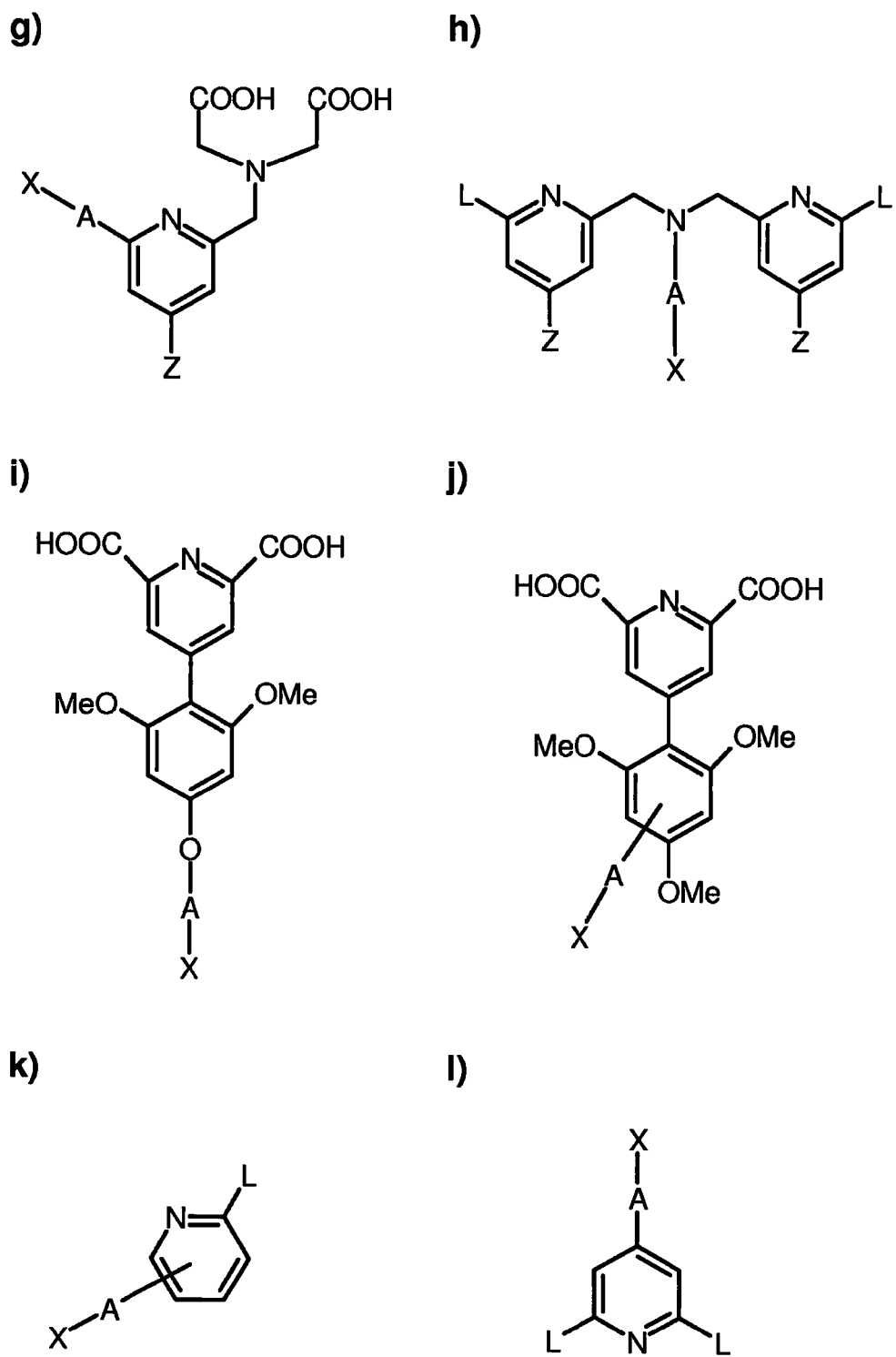
Figure 5/ii

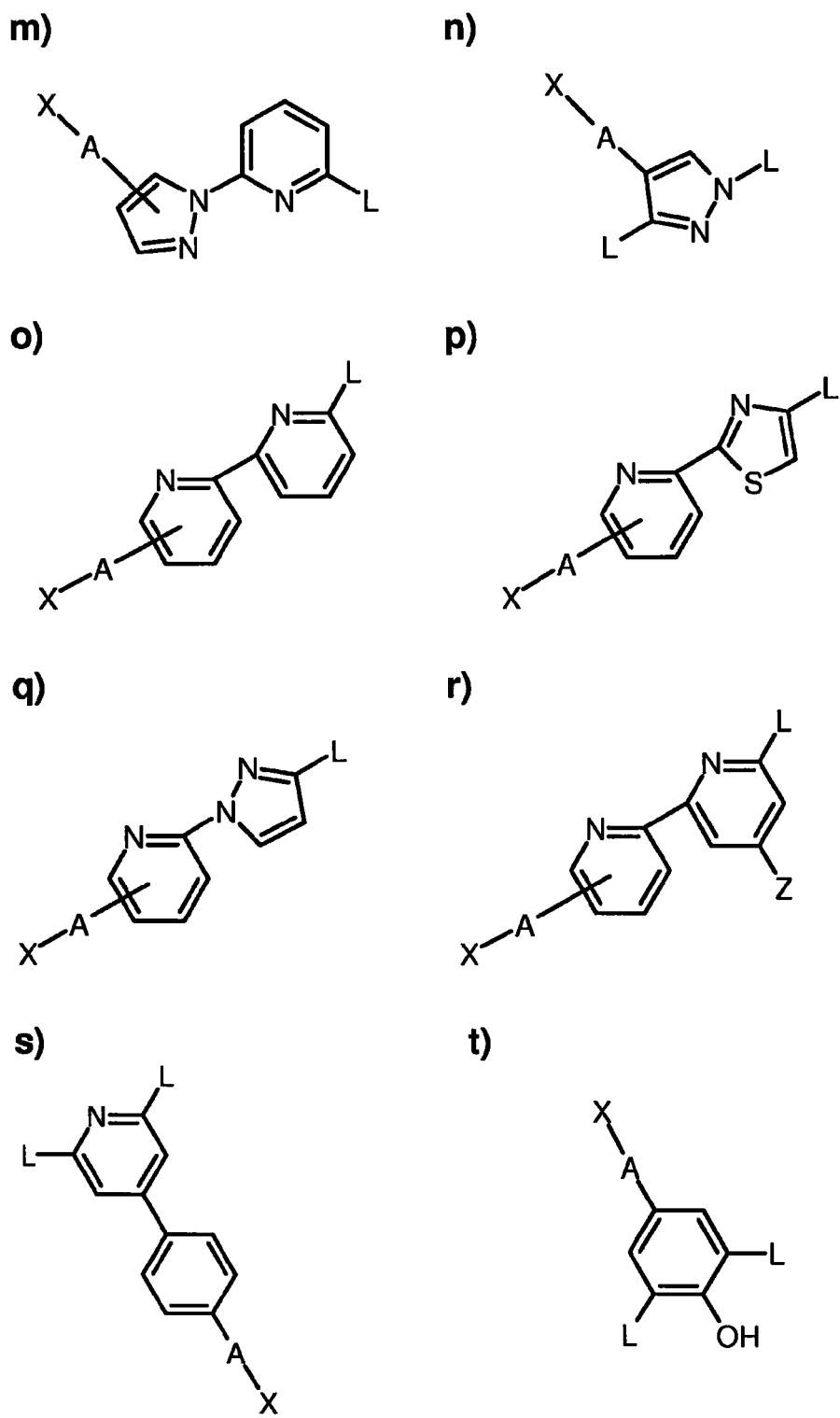
Figure 5/iii u)
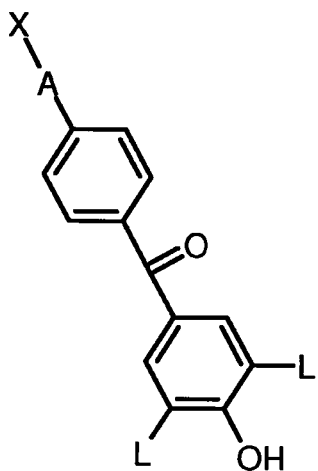
v)
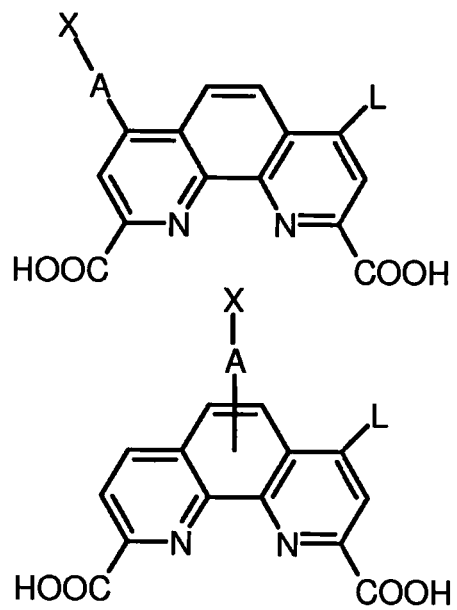
w)
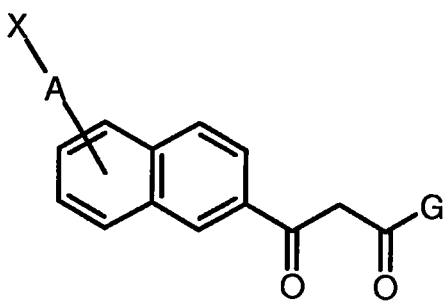
x)
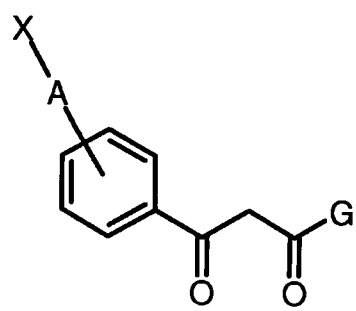
y)
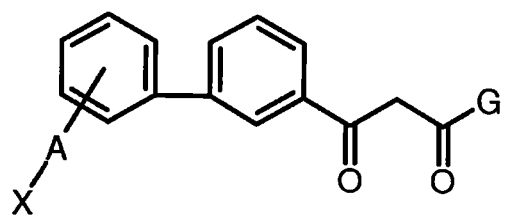
z)
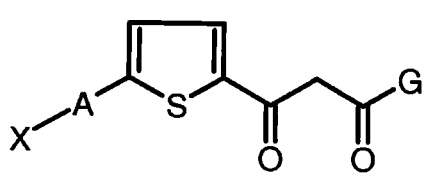
Figure 5/iv a) 
b) 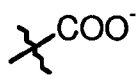
c) 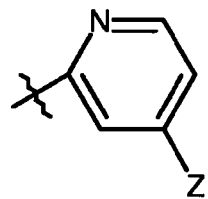
d) 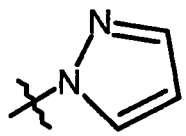
e) 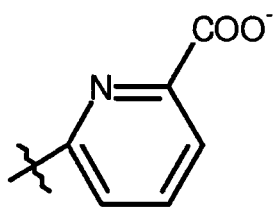
f) 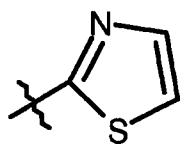
g) 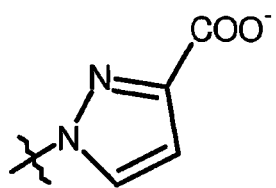
h) 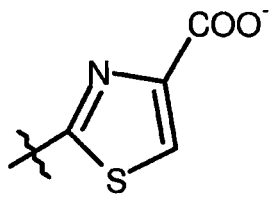
i) 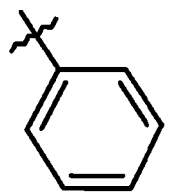
j) 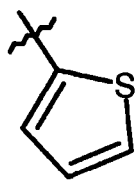
k) 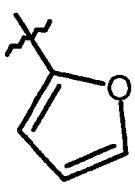
l) 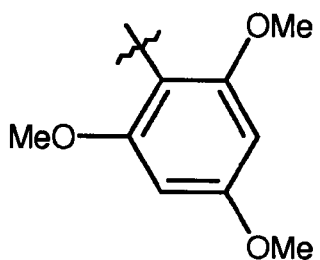
Figure 6

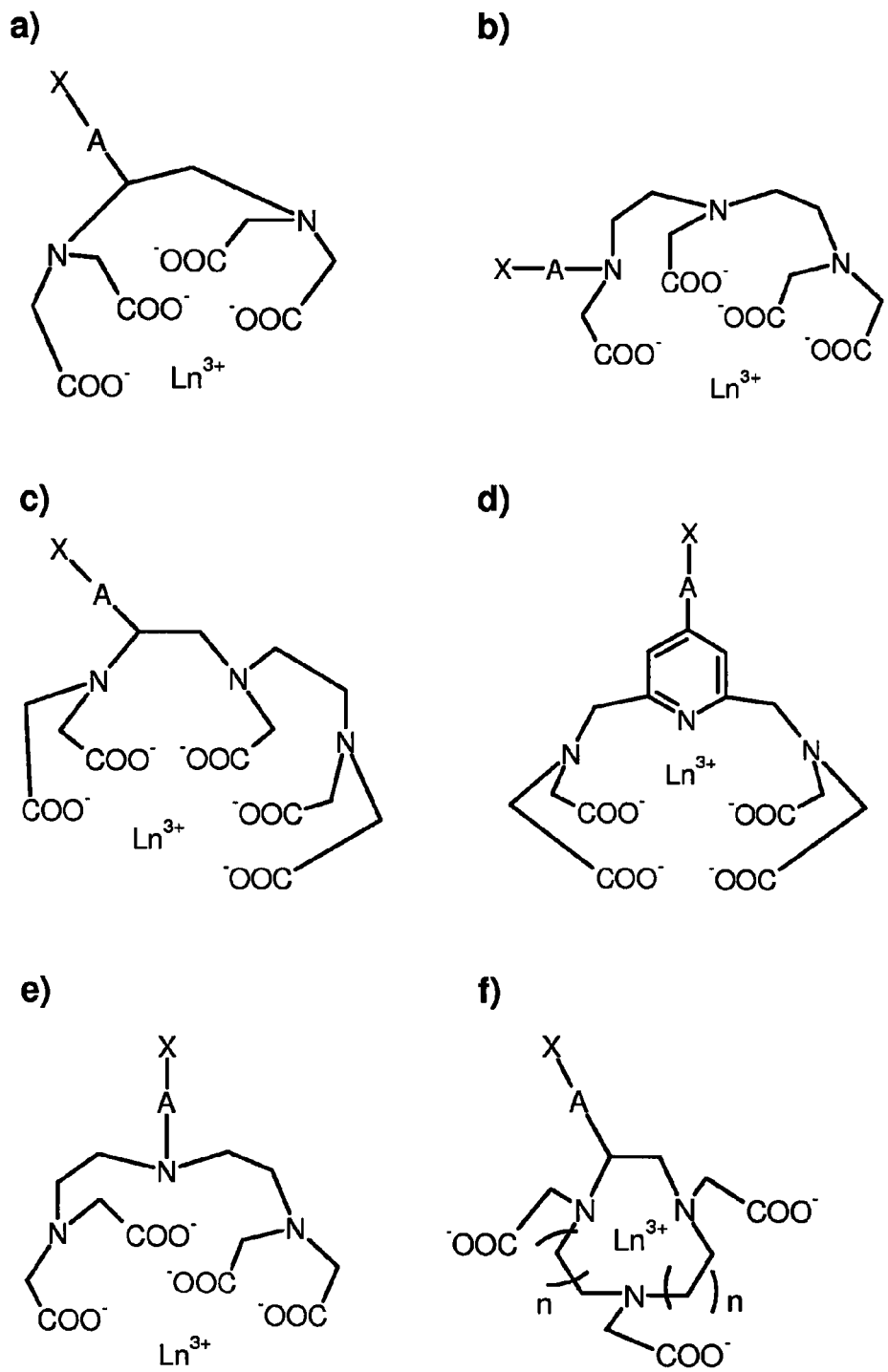
Figure 7/i g)
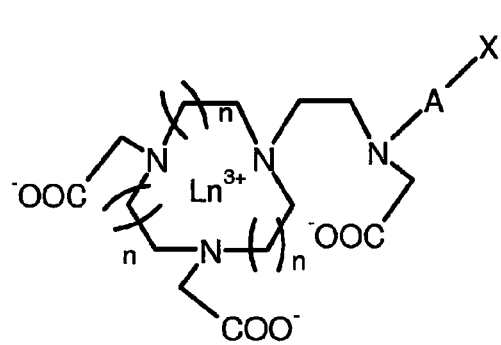
h)
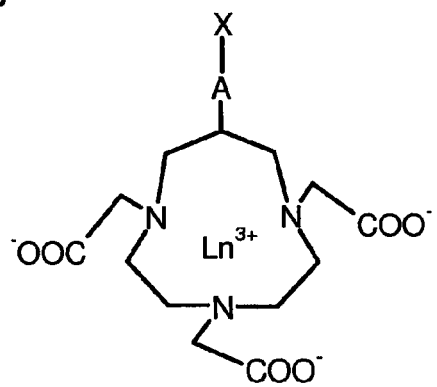
i)
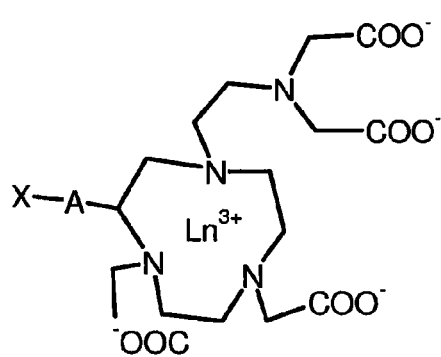
j)
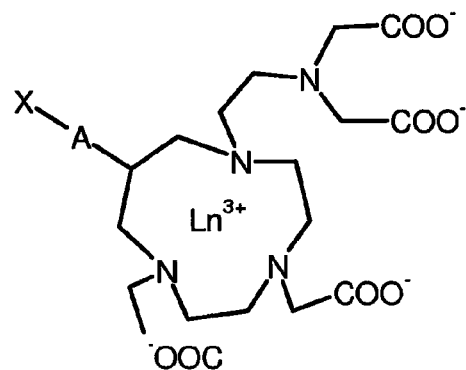
k)
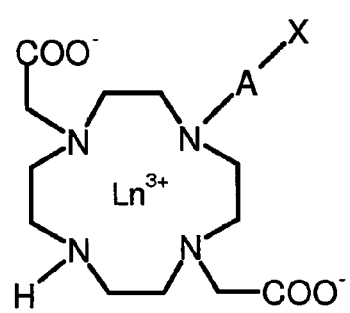
l)
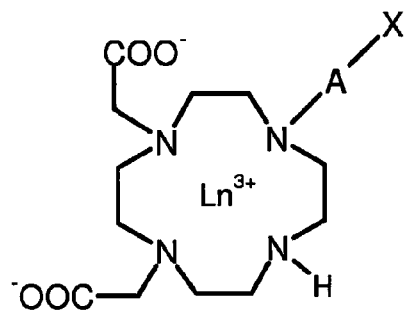
Figure 7/ii m)
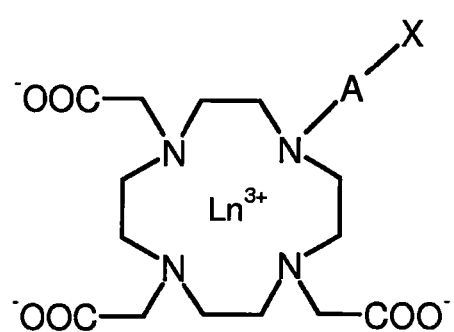
n)
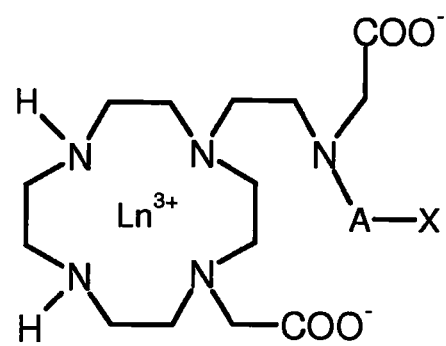
o)
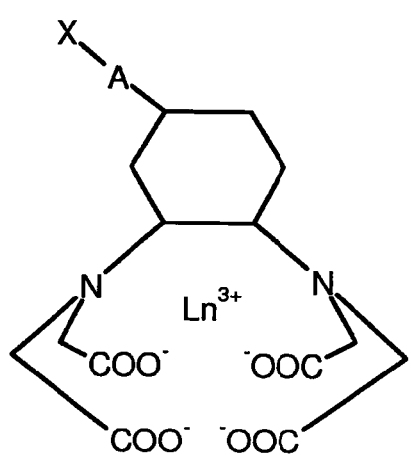
p)
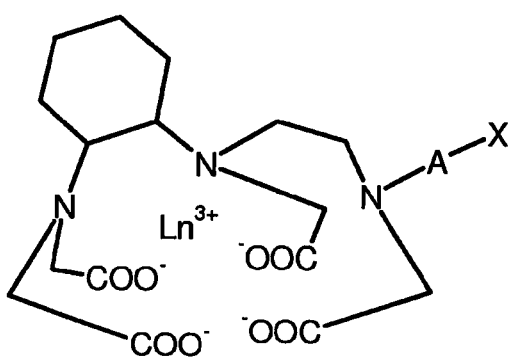
Figure 7/iii

SEQUENCE LISTING

```
<160> NUMBER OF SEQ ID NOS: 11

<210> SEQ ID NO 1
<211> LENGTH: 32
<212> TYPE: DNA
<213> ORGANISM: Artificial Sequence
<220> FEATURE:
<223> OTHER INFORMATION: E1/E6 target DNA nucleotide

<400> SEQUENCE: 1
gatgcagtag caggaagagg atcgtagcaa tg                                    32

<210> SEQ ID NO 2
<211> LENGTH: 16
<212> TYPE: DNA
<213> ORGANISM: Artificial Sequence
<220> FEATURE:
<223> OTHER INFORMATION: E1/E4/E6 probe A

<400> SEQUENCE: 2
cattgctacg atcctc                                                      16

<210> SEQ ID NO 3
<211> LENGTH: 16
<212> TYPE: DNA
<213> ORGANISM: Artificial Sequence
<220> FEATURE:
<223> OTHER INFORMATION: E1/E4/E6 probe B

<400> SEQUENCE: 3
ttcctgctac tgcatc                                                      16

<210> SEQ ID NO 4
<211> LENGTH: 32
<212> TYPE: DNA
<213> ORGANISM: Artificial Sequence
<220> FEATURE:
<223> OTHER INFORMATION: E2 target oligonucleotide

<400> SEQUENCE: 4
ctgctctatc cacggcgccc gcggctcctc tc                                    32
```

<210> SEQ ID NO 5
<211> LENGTH: 16
<212> TYPE: DNA
<213> ORGANISM: Artificial Sequence
<220> FEATURE:
<223> OTHER INFORMATION: E3 probe C

<400> SEQUENCE: 5
cattgctacg atcctc                                                          16

<210> SEQ ID NO 6
<211> LENGTH: 34
<212> TYPE: DNA
<213> ORGANISM: Artificial Sequence
<220> FEATURE:
<223> OTHER INFORMATION: E4 biotinylated target oligonucleotide

<400> SEQUENCE: 6
ttgatgcagt agcaggaaga ggatcgtagc aatg                                      34

<210> SEQ ID NO 7
<211> LENGTH: 159
<212> TYPE: DNA
<213> ORGANISM: Artificial Sequence
<220> FEATURE:
<223> OTHER INFORMATION: E8 template

<400> SEQUENCE: 7
cttcagcgct acacacgctc aaatcatcga ggaaaaccgt atgagaaacg gatctaagct          60
tgtcatttga taaagcatca tgcaacatta acccgagata cgatttgtcc atatctttga         120
tacgacgccg caaaagctct tcccaagccg agtctacag                                159

<210> SEQ ID NO 8
<211> LENGTH: 24
<212> TYPE: DNA
<213> ORGANISM: Artificial Sequence
<220> FEATURE:
<223> OTHER INFORMATION: E8 5 primer

<400> SEQUENCE: 8
ctgtagactc ggcttgggaa gagc                                                 24

<210> SEQ ID NO 9
<211> LENGTH: 25
<212> TYPE: DNA
<213> ORGANISM: Artificial Sequence
<220> FEATURE:
<223> OTHER INFORMATION: E8 3 primer

<400> SEQUENCE: 9
aagccttccc tttatacgct caagc                                                25

<210> SEQ ID NO 10
<211> LENGTH: 20
<212> TYPE: DNA
<213> ORGANISM: Artificial Sequence
<220> FEATURE:
<223> OTHER INFORMATION: E8 probe A

<400> SEQUENCE: 10
aatcgtatct cgggttaatg                                                      20

<210> SEQ ID NO 11
<211> LENGTH: 20

```
<212> TYPE: DNA
<213> ORGANISM: Artificial Sequence
<220> FEATURE:
<223> OTHER INFORMATION: E8 probe B

<400> SEQUENCE: 11
ttgcatgatg ctttatcaaa                                           20
```

US 8,993,246 B2

LUMINESCENCE ASSAY METHOD

This application is the National Stage of International Application No. PCT/FI2010/050222, filed Mar. 23, 2010, which claims benefit of U.S. provisional application 61/162,752, filed Mar. 24, 2009 and Finnish priority application 20095302, also filed Mar. 24, 2009.

FIELD OF THE INVENTION

This invention relates to a bioassay method for detecting and/or quantitating an analyte.

BACKGROUND OF THE INVENTION

The publications and other materials used herein to illuminate the background of the invention, and in particular, cases to provide additional details respecting the practice, are incorporated by reference.

A number of assays based on bioaffinity binding reactions or enzymatically catalyzed reactions have been developed to analyze biologically important compounds from or their activity or their biological effect or its modulation induced by various biological samples, samples in environmental studies, industrial processes and compound libraries. Some of these assays rely on specific bioaffinity recognition reactions, where e.g. natural biological binding components, artificially produced binding compounds or moulded plastic imprints (molecular imprinting) are used as recognition elements to form the specific binding assay. Other assays rely on activity or modulation of the activity of compounds present in sample or added into reaction (e.g. biologically active enzymes, chemical compounds with activity on biological molecules, enzyme substrates, enzyme activators, enzyme inhibitors, enzyme modulating compounds) and so on. Such assays generally rely on a label or a combination of multiple labels generating signals to e.g. quantitate the formed complexes after recognition and binding reactions. In heterogeneous assays a separation step (separations like precipitation and centrifugation, filtration, affinity collection to e.g. plastic surfaces such as coated assay tubes, slides or microparticles, solvent extraction, gel filtration, or other chromatographic systems, and so on) is generally required before e.g. the free or bound fraction of the label signal can be measured. In homogeneous assays the signal of the label or labels is modulated or formed due to binding reaction or enzymatic activity or other measured effect, and no separation step is needed before measurement of the label signal. Both in heterogeneous and homogeneous assays the measurement of the label signal from free or bound fraction of the label generally enables the calculation of the analyte or activity in the sample directly or indirectly, generally through use of a set of standards to which unknown samples are compared. Various binding assay methods have been reviewed in Principles and Practice of Immunoassay, 2nd ed., C. P. Price and D. J. Newman, eds., Palgrave Macmillan, Hampshire, UK, 2001; and The Immunoassay Handbook, 2nd ed. David Wild, ed., Nature Publishing Group, New York, N.Y., 2001.

Development of simple, sensitive, and quantitative, preferably homogeneous and multiplexed nucleic acid hybridization assays has been an important objective in evolution of fluorescent labels and detection techniques. Homogeneous methods have received much attention, because they eliminate the need for cumbersome steps of separation of bound and free label, and significantly simplify construction of an instrument required to perform an assay automatically. Further, homogeneous methods are required for e.g. techniques involving real-time monitoring of nucleic acid amplification reactions [Higuchi, R., et al. (1992) Biotechnology 10: 413-417; Higuchi, R., et al. (1993) Biotechnology 11:1026-1030]. Currently available label technologies suitable for homogeneous, non-separative monitoring of nucleic acid hybridization still suffer from interference of sample matrices, the technologies cannot be universally employed, e.g. are not suitable for 5' nuclease assays [U.S. Pat. No. 5,210,015], or they simply do not enable detection sensitive enough to be performed using a rapid read-out required, or the instrumentation required for detection is too complex or expensive to be feasibly constructed or miniaturized.

Homogeneous detection techniques based on photoluminescence have received much attention, since several types of physical and chemical interactions can be employed to modulate the emission of photoluminescent labels due to formation of specific biomolecular complexes. The commonly employed methods are based on polarization of the emitted light or non-radiative energy-transfer (resonance energy transfer) between two photoluminescent compounds (donor and acceptor) or between a photoluminescent and a non-luminescent compound (donor and quencher) [Hemmilä I, Clin Chem 1985; 31:359-370].

Resonance Energy Transfer

Förster resonance energy transfer (FRET) is a strongly distance dependent (to inverse sixth power) non-radiative energy transfer mechanism between two properly chosen fluorescent molecules present in close proximity [Förster, T (1948) Ann Physik 2: 55-75]. Resonance energy transfer (RET) occurs at practical efficiency when a donor and an acceptor fluorophore are within Förster radius (typical values 4-7 nm) and the donor emission spectrum and the acceptor absorption spectrum overlap. The RET is typically monitored either by measuring a decrease of donor emission or an increase of acceptor emission intensity (known as sensitized acceptor emission) [Selvin, P R (1995) Biochem Spectroscopy 246: 300-334] resulting from proximity of donor and acceptor. In case of non-fluorescent acceptor (known as quencher) a change of donor emission intensity is monitored.

Although FRET is a widely employed and an essential technique in many applications, it has severe performance limitations [Hemmilä, I (1985) Clin Chem 31: 359-370.] and, in practice, the RET probes fail to comply with the strict requirements of true proximity probes. Proximity probing is a technique capable of detecting the nearness of the two proximity probes and is used for specific, sensitive and rapid detection of various biomolecules. A proximity probe consists typically of a binding moiety (recognition element) or other recognition site (with specific affinity for the target molecule i.e. analyte) and the target molecule is able to direct binding of the two similar or different proximity probes into adjacent positions. The proximity between the probes is thus provided when two probes bind e.g. to their respective binding sites on a target molecule. Characteristics to the true proximity probes is that they do not generate any significant signal (i.e. are not detectable) when the probe pair is not in immediate proximity directed by the target molecule, but the probe pair is switched to a detectable state due to specific recognition events in presence of target molecule. Proximity probing using monovalent proximity probes, performed in solution with no washing steps, has been described in WO 01/61037; Schallmeiner et al. (2006) Nature Methods 4: 135-137 and WO/2003/044231.

The conventional FRET-based assays are susceptible to i) direct excitation of the acceptor (the acceptor is weakly excited at the same wavelength where the donor is excited), ii) crosstalk of donor emission (the donor has some emission at the same wavelength where the acceptor emission is measured), iii) radiative energy transfer (less distance dependent; to inverse second power) through absorption of donor emission (photons) by acceptor fluorophores not necessarily in proximity, and iv) scattered excitation light and autofluorescence (from sample, other assay components, plastics and detection instrument itself) generating background signal. Thus, conventional fluorophores and RET probes do not provide the specificity in signal generation required for the proximity probe binding-principle. Further, it is difficult to measure more than two parameters simultaneously in a multiparametric FRET-based assay due to wide spectral coverage of an individual donor-acceptor pair.

Time-Resolved Fluorometry

Detection sensitivity of conventional fluorescence based techniques is limited by autofluorescence, scattered excitation light and absorbance of biological sample matrices, and in acceptor-based resonance energy transfer based assays also by crosstalk of the emission of the donor at acceptor-specific emission wavelength and direct excitation of the acceptor at the donor-specific excitation wavelength. Many compounds and proteins present in biological fluids or serum are naturally fluorescent, and the use of conventional fluorophores leads to serious limitations of sensitivity [Soini E and Hemmilä I (1979) Clin Chem 25: 353-361; Wu P and Brand L (1994) Anal Biochem 218:1-13]. Another major problem when using homogeneous fluorescence techniques based on intensity measurements is the inner filter effect and the variability of the optical properties of a sample. Sample dilution has been used to correct this drawback, but always at the expense of analytical sensitivity. Feasibility of fluorescence resonance energy transfer in assay applications was significantly improved when fluorescent lanthanide cryptates and chelates with long-lifetime emission and large Stokes' shift were employed as donors in the 1990's [Mathis G (1993) Clin Chem 39:1953-1959; Wu P and Brand L (1994) Anal Biochem 218, 1-13; Selvin P R et al. (1994) Proc Natl Acad Sci USA 91:10024-10028; Stenroos K et al. (1998) Cytokine 10:495-499; WO 98/15830; U.S. Pat. No. 5,998,146; WO 87/07955; Blomberg, K et al. (1999) Clin Chem 45:855-61].

Lanthanide chelates and cryptates, due to their enhanced detectability compared to traditional organic fluorophores, are nowadays widely used in the analysis of various biological molecules. Luminescent chelates of lanthanides (rare earths, e.g. trivalent europium, terbium, samarium and dysprosium) are an exceptional group of photoluminescent compounds [Bünzli, J C G and Piguet, C (2005) Chem Soc Rev 34: 1048-1077]. The lanthanide ions themselves have very low absorption and, in addition, the excited state of the lanthanide is efficiently quenched by coordinated water molecules. Thus, the only practical solution to their excitation is to use a coordinating ligand comprising a light harvesting moiety, such as an organic antenna chromophore in the intrinsically luminescent lanthanide(III) chelate. In practice, the photoluminescence efficiency (product of absorption coefficient and quantum yield) of the lanthanide ion chelated to an efficient antenna ligand, displacing all the coordinating water molecules, can be readily enhanced up to 100 000-fold compared to a bare ion. Further, the distinct emission bands characteristic to lanthanide ion enable simultaneous measurement of up to four different lanthanides with minimal spectral crosstalk. The luminescence properties of lanthanides enable also efficient separation of the background noise from biological material and thus increase of the sensitivity of the assay [J. Yuan, G. Wang (2005) J Fluoresc. 15, 559].

Lanthanide ions complexed to a suitable chelate (e.g. aminopolycarboxylic acid) containing organic light harvesting antenna moiety or chromophore possess unusual fluorescence characteristics compared to conventional fluorophores: large Stokes shift (150-300 nm), narrow and distinct emission bands characteristic to lanthanide ions, and long luminescence lifetime (up to 2000 microseconds). The exceptional fluorescence lifetime enables efficient background separation by selection of such a temporal gate (typically hundreds of microseconds) that detection is performed only when the background fluorescence (short living) has decayed away, while the lanthanide luminescence is still reasonable intense. Moreover, the large Stokes shift and the narrow emission bands enable efficient wavelength filtering to spectrally select the lanthanide luminescence, resulting in highly sensitive reporter technology (equal performance to enzyme amplified chemiluminescence) and possibility for multiparametric measurement. The technology utilizes a dedicated detection method known as (microsecond) time-resolved fluorometry [Soini E and Kojola H (1983) Clin Chem 29: 65-68]. The long-lifetime fluorescence of luminescent lanthanide chelates is typically excited at ultraviolet or blue visible light [Yang C, et al. (2004) Angew Chem Intl Ed 43: 5010-5013] and the emission is detected at green and red visible wavelengths. In case of erbium, neodymium and ytterbium the excitation can be at visible wavelenghts and the emission at visible or at infrared wavelengths [Werts, M. H. V., et al. (1997). Chem Phys Lett 276: 196-201]. Also platinum (III) and palladium (III) should be noted to have similar spectral and temporal properties when complexed to phorphyrins [de Haas, R. R., et al. (1999) J Histochem Cytochem 47: 183-196].

The excitation mechanism of lanthanide(III) chelates, where an organic light harvesting antenna is used to excite the emissive lanthanide(III) ion via energy-transfer, is exceptional among fluorescent reporters [Hemmilä, I. and Laitala, V. (2005) J Fluoresc 15: 529-542]. Luminescent lanthanide (III) chelates comprise a reactive group, light-harvesting antenna and chelating groups, which chelate the lanthanide (III) ion through coordination bonds. The organic light harvesting chromophore is first excited from ground singlet state ($S_0$) to first singlet state ($S_1$) by light absorption, and the chromophore undergoes transition to triplet state ($T_1$) by intersystem crossing (ISC). The triplet state of the antenna chromophore can transfer the excitation energy to appropriate 4f energy level of the lanthanide(III) ion. Thereafter, the lanthanide ion produces characteristic f-f transition luminescence with distinct emission bands and with a long luminescence lifetime due to forbidden transition.

The development of a stable lanthanide chelate structure containing an efficient light-harvesting antenna originally turned out difficult. The problem was circumvented in heterogeneous assays by labelling the biomolecular binder with an ion carrier chelate and using a separate chelating solution (with low pH) to dissociate the ion from the carrier chelate to form a new highly fluorescent lanthanide complex. The ion carrier chelate used for labelling contain, in addition to the lanthanide ion and carrier chelate, a reactive group for covalent coupling.

The chelate complexes of metals (coordination compounds) are formed through binding of ligand (or chelating molecule) to metal ion through coordinated groups. The total number of points of attachment of the ligand to the central metal ion is termed the coordination number. The ligands can be characterized for points of attachment, listing them as monodentate, bidentate, etc., where the concept of teeth (dent) reflects the number of atoms bonded to the metal centre in the chelate. The chelate (or chelate complex) is a compound that comprises at least a single ligand, which has at least two teeth (called bidentate), and at least one metal ion bound by the ligand. The stability of chelate complexes in solution is described by the magnitude of stability (or formation) constant for association of the metal (cations) to ligands (neutral or anionic). The larger the stability (or formation) constant, the higher proportion of the metal is complexed in presence of the ligand. For binding of multiple ligands stepwise stability constants can be defined and the stability constant is then the product of stepwise stability constants. Since the stability constants can vary with tens of magnitudes, the value is typically expressed as logarithm (log 10). Multidentate ligands form stronger metal ion complexes than monodentate ligands. Typically the stability constant increases with number of coordination dentates of the ligand, but in addition the structure of the ligand is important. Ring or cyclic structures reducing the freedom of conformations of the binding ligand often also result in higher stability constants. Determination of stability constants for europium(III) complexes is described e.g. by Wu, S L and Horrocks, W D (1997) Journal of the Chemical Society-Dalton Transactions 1497-1502. Typically neighbouring lanthanides (e.g. Eu(III) and Gd(III)) in the periodic table have very similar stability constants with the same ligand.

The stability (or formation) constant describes the maximum stability of the lanthanide chelate at alkaline conditions, where the ligand is fully deprotonated and the protons do not significantly compete with binding to metal ion. The conditional stability constants (known also as effective formation constant), taking into account the pH and prototation of the ligand, are more appropriate to describe the actual stability of the complex at e.g. physiological pH and conditions typically prevailing in bioassays. Description of the terms "Determination of conditional stability constants for europium(III) complexes is described e.g. by Siaugue, J. M. et al. (2003) *J Photochem Photobiol A: Chem* 156: 23-29.

Examples of both stability constants and conditional stability constants at physiological pH as well as kinetic stability data are described in Morcos, S. K. (2007) "Chelates and stability", pp. 155-160 in Medical Radiology, 2nd revised edition by Thomsen, H. S. and Webb, J. A. W, Springer, Berlin, 2009. A large collection of stability constants is compiled to the IUPAC stability constant database commercially available from Academic Software, Yorks, United Kingdom.

The technique based on an ion carrier chelate and a separate chelating solution was known as dissociation enhanced lanthanide fluoroimmunoassay assay [U.S. Pat. No. 4,565,790; Hemmilä, I et al. (1984) *Anal Biochem* 137: 335-343; Soini, E and Lövgren, T (1987) *CRC Crit Rev Anal Chem* 18: 105-154; and Siitari, H et al. (1983) *Nature* 301: 258-260]. The technology is widely applied in heterogeneous biomolecular binding assays and has later been improved to speed up the dissociation by utilizing an antenna ligand being able to form lanthanide complex at lower pH [WO 2003/076939, U.S. Pat. No. 7,211,440, U.S. Pat. No. 7,381,567 and EP 1 483 582]. The enhancement-based assays typically utilize moderately strong aminopolycarboxylate-based lanthanide (III) ion carrier chelates (such as derivatives of EDTA and DTPA, described in e.g. U.S. Pat. No. 4,822,594 and U.S. Pat. No. 6,190,923) as labelling reagents and beta-diketone-based antenna ligands in enhancement solution to create luminescence. Also ion carrier chelates and labelling reagents based on DOTA and TETA have been presented [Hemmilä, I. (1995) *J. Alloys Comp* 225: 480-485]. To derivatize the ligand for labelling, e.g. one carboxylic acid of DOTA can be replaced with a group for attachment to biomolecules. The stability of the lanthanide(III) ion carrier chelates used for dissociation enhancement, however, should be only moderate and the dissociation kinetics quite rapid especially at low pH, as otherwise the ion is not released fast enough for fluorescence enhancement. On the other hand, the development of very stable carrier chelates for gadolinium(III) ion has been in focus in development of contrast agents for magnetic resonance imaging [Brücher, E. (2002) Topics in Current Chemistry 221: 103-122; Morcos, S. K. (2007) "Chelates and stability", pp. 155-160 in Medical Radiology, 2nd revised edition by Thomsen, H. S. and Webb, J. A. W, Springer, Berlin, 2009; and Woods, M. et al. (2006) Journal of Supramolecular Chemistry, Vol 2., 1-15].

Several intrinsically fluorescent lanthanide chelates have been developed [Alpha, B et al. (1987) *Angew Chem Int Ed Engl* 26: 1266-1267; H. Takalo et al. Bioconjugate Chem. 1994, 5, 278; Takalo, H et al. (1997) *Helv Chim Acta* 80: 372-387; von Lode, P et al. (2003) *Anal Chem* 75: 3193-3201; Beeby, A. (2000) *J. Chem. Soc., Perkin Trans.* 2, 1281-1283; Hakala, H. et al. (2002) *Inorg Chem Comm* 5: 1059-1062; Li, M. and Selvin, P. R. (1995) JACS 117: 8132-8138; and WO 2005/021538]. These stable, luminescent lanthanide complexes include both cryptates and highly luminescent chelates (mainly aminopolycarboxylic based chelating structures) for several lanthanides [europium(III), terbium(III), samarium (III) and dysprosium(III)]. The chelating ligands are designed to combine a moderately strong or strong binding of the lanthanide(III) ion and light-harvesting part to the one and same molecule and they can be used as donors in FRET based assays. In most of the chelates, the light-harvesting (energy-absorbing) and mediating part is composed of derivatized pyridine or pyridine manifold. Some antenna structures contain other heteroatomic conjugated ring structures such as pyrazole. In addition to the lanthanide ion, light-harvesting organic moiety and carrier ligand, the intrinsically luminescent lanthanide complexes used for labeling contain a reactive group for covalent conjugation.

Lanthanide luminescence yield can be enhanced by co-luminescence based enhancement utilizing additional antenna ligands and non-luminescent lanthanide ions [e.g. yttrium(III) or gadolinium(III)] to absorb excitation light and transfer the energy via triplet-triplet migration to an antenna ligand coordinated to a luminescent lanthanide ion [e.g. europium(III)], that is present either in the same self-assembled polymeric lanthanide complex or in the same micellar environment. Intermolecular energy migration greatly enhances the number of effective light harvesting antennas per luminescent lanthanide and results in enhancement of the luminescence intensity of certain luminescent lanthanide ions up to hundred-fold or even more [Xu, Y Y et al. (1991) *Analyst* 116: 1155-1158; Latva, M et al. (1995) *J Chem Soc Perkin Trans* 2 995-999].

Lanthanide-Based RET

Two novel resonance energy transfer-based methods utilizing different photoluminescent lanthanide-based reporters [Mathis, G (1993) *Clin Chem* 39: 1953-1959; Blomberg, K et al. (1999) *Clin Chem* 45: 855-861] have been introduced to largely solve the major problems associated with conventional FRET-based homogeneous assays. Both of these methods provide significant advantages compared to the conventional methods, but the specificity in signal generation is still limited by the radiative energy transfer (absorption of donor emission), especially when the labeled probes are present in high concentration (e.g. to achieve a large dynamic range, or to facilitate binding in case of weak interactions) [H. Bazin, M. et al. (2001) *Spectrochim. Acta, Part A,* 57]. Excess of the unbound acceptor result in slowly-decaying radiative background signal at the acceptor-specific wavelength, but also donor cross-talk at the measurement wavelength can increase the background signal unless sufficient spectral resolution is used. The utilization of non-overlapping acceptor (non-overlapping FRET) with lanthanide chelate donor [Hemmilä, I. and Laitala, V. (2005) *Anal. Chem.* 77:1483-1487; Laitala, V. and Hemmilä I. (2005) *Analytica Chimica Acta* 551: 73-78] can further eliminate possible background through reabsorption of donor emission.

In case of a long-lifetime fluorescent lanthanide chelate (or cryptate) as a donor in combination with a conventional, short-lifetime fluorescent acceptor [Mathis, G (1993) *Clin Chem* 39: 1953-1959; Blomberg, K et al. (1999) *Clin Chem* 45: 855-861] the energy-transfer excited acceptor emission can be temporally resolved (with time-resolved fluorometry) from the short-lifetime, directly-excited fluorescence of the acceptor and the background fluorescence. The crosstalk of donor emission to acceptor emission wavelength is also nearly completely avoided due to narrow "line like" emission bands of donor emission. The same advantages are obtained by using upconverting (anti-Stokes photoluminescent) lanthanide-doped compounds [Heer, S et al. (2004) *Adv Mater* 16: 2102-2105; Kuningas, K et al. (2005) *Anal Chem* 77: 7348-7355] as donors in combination with a conventional, fluorescent acceptor and measuring the energy-transfer excited acceptor emission specifically at visible wavelengths under infrared excitation of the donor. The infrared illumination does not directly excite the conventional fluorescent acceptor nor generate any autofluorescence at visible wavelengths, and the narrow banded donor emission effectively eliminates the potential crosstalk.

Anti-Stokes emission of up-converting lanthanide-doped nanocrystals occurs at shorter wavelength (at visible wavelengths) than infrared excitation, providing a large anti-Stokes shift (up to over 300 nm) and efficient spectral separation of the autofluorescence and scattered excitation light (without temporal resolution) from the emission at visible wavelengths [Soukka, T. et al. (2005) *J Fluorescence* 15: 513-528]. Upconversion is a unique feature of certain lanthanide-based materials (with exception of a few transition metals) capable of converting infrared to visible light via sequential non-coincident absorption of two infrared photons with efficiency greatly enhanced compared to simultaneous two-photon absorption. The upconversion mechanism is based on either one type of lanthanide ion or two different lanthanide ions in proximity. The lanthanide dope ions have long-lifetime excited states, which operate as metastable states excited from a ground state to be excited again to an emission state, or transfer energy to another lanthanide ion. The lanthanide-based upconversion can provide extreme detectability, as the observed photoluminescence background is equivalent to that achieved in luminescence counting limited only by the dark current and sensitivity of the detector.

Up-converting chelates have been described in U.S. Pat. No. 5,891,656, Xiao, X. et al. (2002) *Opt Lett.* 30: 1674-1676; and Faris G W and Hryndza M, Proc SPIE—Int Soc Opt Eng 2002; 4626: 449-452. In an up-converting lanthanide chelate a single rare earth ion [e.g. Er(III), Tm(III) or Ho(III)] or a combination of different lanthanide ions is chelated to a mono or multinuclear complexing ligand or multiple ligands [WO 2004/086049 and Soukka, T. et al. (2008) *Annals of the New York Academy of Sciences* 1130: 188-200]. The ligand may or may not contain a light harvesting structure. The light collection efficiency of individual ions and chelated ligands without light harvesting structure is poor and requires relatively high excitation light intensity. Therefore, up-converting rare earth chelates can be designed to contain a ligand with light-harvesting organic or inorganic structures, e.g. another ion such as Yb(III), incorporated. The collected energies of two or more photons are transferred one after another by intramolecular non-radiative processes from the singlet to the triplet state of the organic structure, then from the triplet state sequentially to the emissive level of the rare earth ion, which then emits a single photon of characteristic emission.

Homogeneous fluorescence-based nucleic acid hybridization assays are typically based on either a quenched probe (donor and quencher in a cleavable oligonucleotide probe) [U.S. Pat. No. 5,538,848] or two energy-transfer probes (separate donor and acceptor labelled probes, which hybridize next to each other to adjacent positions). FIG. 1 describes a energy-transfer probe based hybridization assay, where two oligonucleotide probes (1 and 2), labelled with donor and acceptor fluorophores (4 and 5, respectively) hybridize (6) to adjacent positions on a complementary target sequence (3). The acceptor is excited at one wavelength ($\lambda_1$) and the (energy-transfer excited) sensitized acceptor emission (8), which is dependent on the hybridization (7), is detected at another wavelength ($\lambda_2$). Although, fluorescence resonance energy-transfer (FRET) is an extremely versatile technology, especially the energy-transfer probe-based assay is limited by energy-transfer efficiency (relatively low signal) and background through reabsorption of the donor emission (limited dynamic range). Further, the quenched probe based assay requires specific labeling with two different dyes and is dependent on the specificity of only a single hybridization event.

Different methods for real-time monitoring of nucleic acid amplification are presented by Koch, W. H (2004) *Nature Reviews Drug Discovery* 3: 749-761. For example, a FRET-pair using one dye coupled to a primer and another to an adjacently hybridizing probe has been presented by Lay, M. J. et al. (1997) *Clinical Chemistry* 43: 2262-2267; FRET-pair using two differently labelled adjacently hybridizing probes by Bernard, P. S., et al. (1998) *American Journal of Pathology* 153: 1055-1061; and competitive hybridization of FRET-pair labelled with complementary probes by Kiviniemi, et al. (2005) *Clinical Biochemistry* 38: 1015-1022.

Feasibility of lanthanide-label technology in fluorescence quenching based assays has been described [Karvinen J et al. (2002) *J Biomol Screen* 7:223-231; Karvinen, J et al. (2004) *Anal Chem.* 76:1429-36; Karvinen, J et al. (2004) *Anal Biochem.* 325: 317-25].

Two approaches have been presented for hybridization dependent formation of fluorescent lanthanide complexes. The first approach was based on a pair of oligonucleotides forming a fluorescent terbium(III) complex upon hybridization; one oligonucleotide was labeled with DTPA-terbium (III) (non-fluorescent terbium chelate) and the other with energy-donor salicylate (light harvesting ligand) [Oser A and Valet G (1990) *Angew Chem Int Ed Engl* 29: 1167-1169]. The second approach was based on similar formation of a fluorescent europium(III) complex but required hybridization of only one probe; the oligonucleotide probe was labeled with EDTA-terbium(III) (non-fluorescent europium chelate) and an energy-donor compound was coupled to an intercalating agent capable of binding to double stranded DNA [Coates et al. (1994) *J. Chem. Soc., Chem. Commun.* 2311-2312; Mullins S T et al. (1996) *J Chem Soc, Perkin Trans* 1 1991: 85-81; Coates J et al. *J Chem Soc, Chem Commun* 1995: 2311-2312; and WO 95/08642]. The first approach has also been used later [Wang et al. (2001) Analytical Biochemistry 299, 169-172; Yuan and Wang (2005) Journal of Fluorescence Vol. 15, No. 4, July, 559-568; Kitamura Y. et al. (2008) Journal of Inorganic Biochemistry Vol 102, No. 10, 1921-1931; and Kitamura, Y. et al. (2006) Nucleic Acids Symposium Series, No. 50, 105-106].

Lanthanide complex-based sensor probes have been described for detection of metal ions e.g. by Leonard, J. P. and Gunnlaugsson, T. (2005) Journal of Fluorescence, 15:585-595 and Viquier and Hulme (2006) Biology, J. Am. Chem. Soc. 128: 11370-11371. For metal cations these sensors work in a competitive manner and utilizing an antenna effect, where the binding of the antenna ligand to the lanthanide ion is blocked by another metal ion present in solution.

Quantitative 5'-nuclease based polymerase chain reaction assay (TaqMan; Applied Biosystems, Foster City, Calif.) is a nucleic acid sequence detection method wherein a single-stranded self-quenching oligonucleotide probe, containing both a fluorescent moiety and a quencher moiety, is cleaved by the nuclease action of nucleic acid polymerase upon hybridisation during nucleic acid amplification [Lie Y S, Petropoulos C J. (1998) *Curr Opin Biotechnol.* 9: 43-48; and Orlando C et al. (1998) *Clin Chem Lab Med.* 36: 255-269].

Molecular beacons are single-stranded oligonucleotide hybridization probes that form a stem-and-loop structure [Tan W et al. (2004) *Curr Opin Chem Biol.;* 8: 547-553; and Tan W et al. (2000) *Chemistry;* 6: 1107-1111]. The loop contains a nucleic acid probe sequence that is complementary to a target sequence, and the stem is formed by annealing of complementary arm sequences that are located on either side of the probe sequence. A fluorescent moiety is covalently linked to the end of one arm and a quencher is covalently linked to the end of the other arm. Due to the proximity of a fluorescent moiety and a quencher moiety molecular beacons do not fluoresce when they are free in solution. However, when they hybridize to a complementary nucleic acid strand containing a target sequence they undergo a conformational change increasing the distance between fluorescent moiety and the quencher moiety that enables the probe to fluoresce. In the absence of a complementary target sequence, the beacon probe remains closed and there is no fluorescence due to intramolecular quenching.

Both self-quenched fluorescent probes and molecular beacons are also used to monitor nucleic acid amplification processes in a thermal cycler; for example in a quantitative polymerase chain reaction the amount of fluorescence at any given cycle, or following cycling, depends on the amount of specific product. The probes bind to the amplified target following each cycle of amplification and the resulting signal upon hybridisation, and in case of Taqman probes upon cleavage, is proportional to the amount of the amplified oligonucleotide sequence. Fluorescence is measured during each annealing step when the molecular beacon is bound to its complementary target or after an elongation step when the Taqman probe is cleaved. The information is then used during quantitative PCR or quantitative RT-PCR (reverse transcriptase PCR) experiments to quantify initial copy number of amplified target nucleic acid sequence based on the threshold cycle number. For endpoint analysis, PCR or RT-PCR reactions containing molecular beacons can be run on any 96-well thermal cycler and then read in a fluorescence reader.

Sensitive and specific proximity probe-based analysis of proteins and potential in medical diagnostics has been described by Gustafsdottir, S. M. (2005) *Anal Biochem* 345: 2-9 utilizing proximity ligation of two oligonucleotide probes.

OBJECT AND SUMMARY OF THE INVENTION

One object of the present invention is to provide a bioassay method for detecting and/or quantitating an analyte.

The present invention provides a bioassay method for detecting and/or quantitating an analyte employing a first group comprising a lanthanide ion carrier chelate and a first recognition element, wherein said lanthanide ion carrier chelate comprises a lanthanide ion carrier ligand and a lanthanide ion; a second group comprising an antenna ligand and a second recognition element; wherein a) said lanthanide ion carrier chelate binds, in the conditions prevailing in said bioassay method, strongly enough to said lanthanide to result in that essentially no, i.e. less than 1 nmol/L, preferably less than 10 pmol/L, free lanthanide ion is present in the conditions prevailing in said bioassay method; or b) said lanthanide ion carrier chelate binds, in the conditions prevailing in said bioassay method, strongly enough to said lanthanide, to result in that essentially no, i.e. less than 1 nmol/L, preferably less than 10 pmol/L, free lanthanide ion is present and an agent complexing said lanthanide ion at a concentration of at least 1 pmol/l is additionally employed; and said antenna ligand binds weakly to said lanthanide ion, i.e. said antenna ligand is either monodentate, bidentate, tridentate or tetradentate; and wherein recognition of said analyte by said first recognition element of said first group and by said second recognition element of said second group results in either i) chelate complementation, i.e. formation of a mixed lanthanide chelate complex through complementation of said lanthanide ion carrier chelate carrying said lanthanide with said antenna ligand, and accordingly in increased fluorescence; or ii) chelate discomplementation, i.e. said lanthanide ion carrier chelate carrying said lanthanide is separated from said antenna ligand, and accordingly in decreased fluorescence.

BRIEF DESCRIPTION OF THE DRAWINGS

FIG. 5/i-iv show examples of schematic chemical structures of light-harvesting antenna ligands applicable to lanthanide chelate complementation. Abbreviations L and Z are used to represent alternative parts of the chemical structures.

FIG. 6 shows examples of schematic structures for alternative parts L (a-h) and Z (j-l) of the light-harvesting antennas presented in FIG. 5/i-iv.

FIG. 7/i-iii shows examples of schematic chemical structures of lanthanide(III) carrier chelates applicable to the lanthanide chelate complementation.

DETAILED DESCRIPTION OF THE INVENTION

Figure 1:
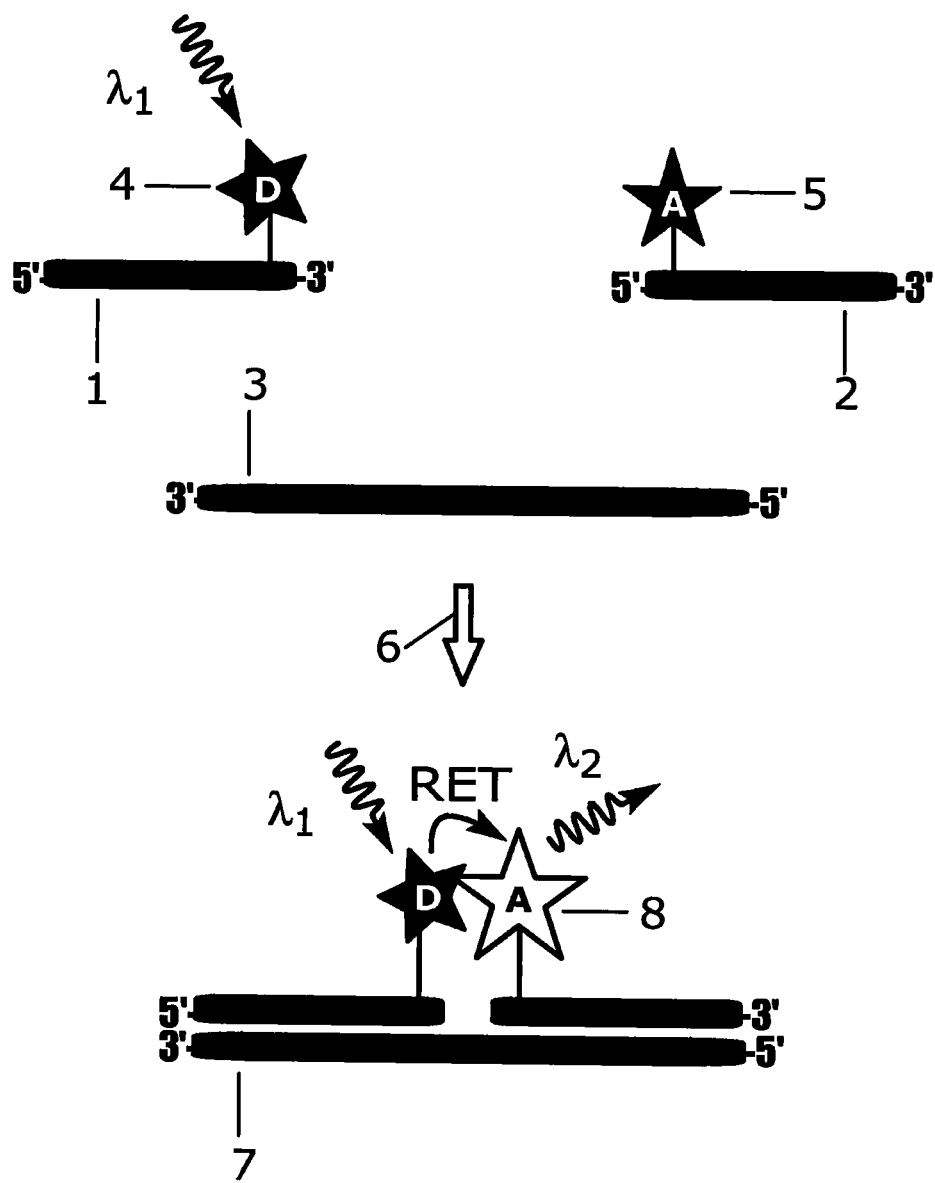
FIG. 1 illustrates a hybridization assay based on energy-transfer probe pair and measurement of the energy transfer between donor and acceptor after hybridization. The probe pair is hybridized to the target sequence next to each others.

In modern bioanalytical assays the measurement of analyte is based on biomolecular recognition and the use of a detectable reporter moiety; e.g. a fluorescent label to enable a rapid read-out. Advances in reporters and detection technologies have resulted in that the reporter per se no more limits the sensitivity, but the signal generated through non-specific interactions of the labelled reagent. These interactions depend on poorly controllable factors and are practically impossible to avoid completely.

"Single-copy" analyte detection has been demonstrated with recent groundbreaking technologies enabling improved specificity in signal generation. These methods, such as proximity ligation assays, where the signal generation is dependent on ligation of two oligonucleotide probes, are yet too complicated for practical applications. The absolute requirement for strict modulation of the reporter signal from a totally dark state to a bright state induced by two recognition events is still an unresolved problem with simple reporter technologies. Only a molecular contact-based complete state switching mechanism would enable adequate specificity in signal generation and even the best Förster resonance energy transfer-based proximity sensing methods do not comply with this.

The inventors have found that lanthanides can provide a unique approach to realize a reporter technology with extraordinary degree of modulation by separating the lanthanide ion carrier chelate and the light harvesting antenna ligand to different reporter moieties. They have solved how to construct a switchable proximity probe-based reporter system, where the dark state of the reporter does not produce fluorescence, which has been a problem in prior art described. The proposed approach surpasses the limitations of FRET, and enables a true fluorescence-based proximity-dependent reporter technology of high specific activity. Signal generation is strictly dependent on self-assembly and complementation of the chelate (molecular contact between the two reporter moieties) guided by other molecular recognition events. A complementing lanthanide-based reporter system can thus be constructed by utilizing two reporter moieties, a non-luminescent ion carrier chelate and a separate antenna ligand, and self-assembly of the complete long-lifetime luminescent chelate (molecular contact at correct orientation) via two simultaneous recognition events guiding the moieties together. This long-lifetime lanthanide fluorescence-based approach provides significant advantages over state-of-the art and can be extended further to lanthanide-based upconversion and anti-Stokes photoluminescence.

According to one embodiment of the present invention the recognition of the analyte by two separate recognition elements brings the lanthanide ion carrier chelate and the antenna ligand to a close proximity allowing the chelate complementation, i.e. the formation of a mixed lanthanide complex and consequently increasing the intensity of the lanthanide luminescence in aqueous solution.

Characteristics to the current invention is that it enables complete switching of the lanthanide luminescence from dark state (non-luminescent state) to bright state (luminescent state) (or vice versa) and no significant fluorescence background is present at dark state in contrast to prior art methods, where the modulation of lanthanide luminescence has been very limited due to observable background fluorescence.

Figure 2:
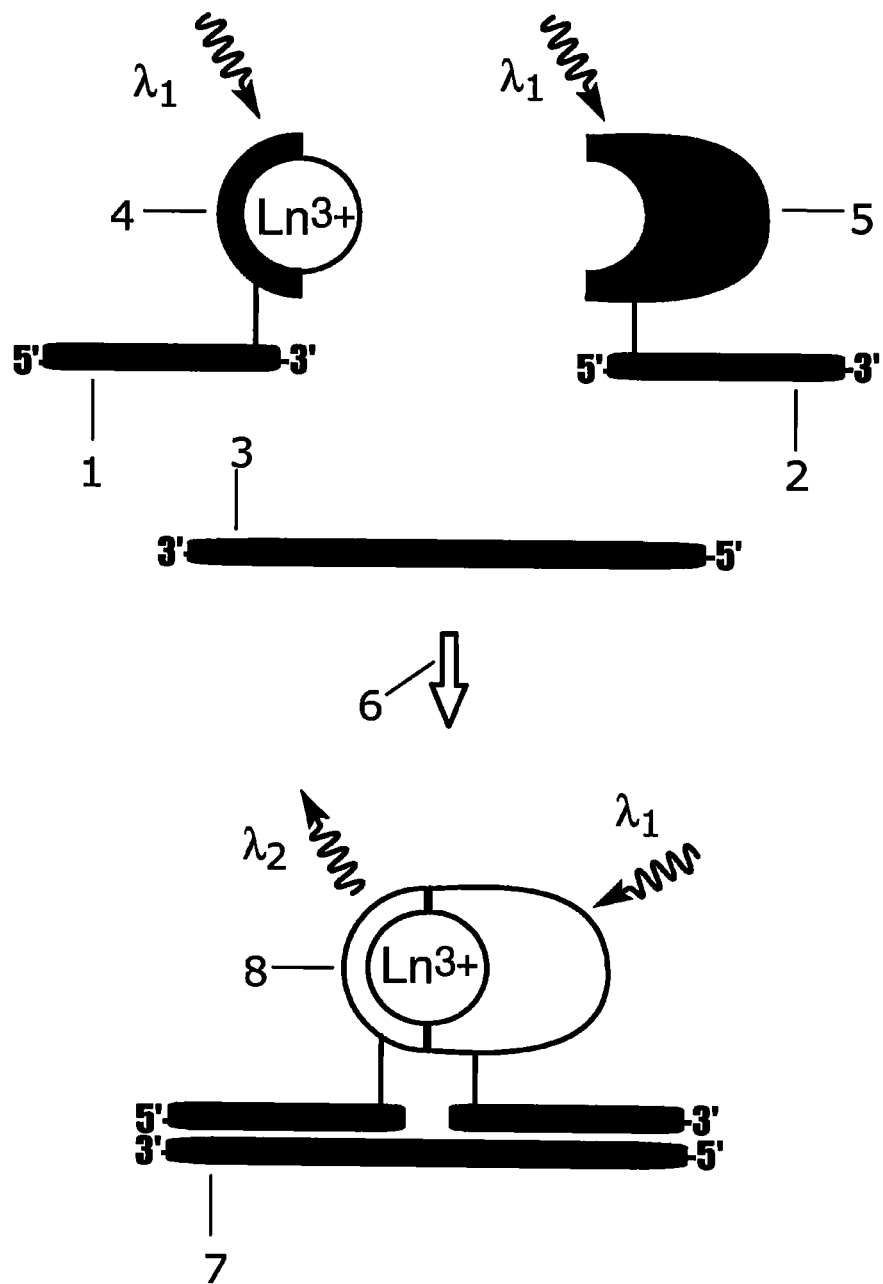
FIG. 2 illustrates an oligonucleotide-directed lanthanide chelate complementation assay using two separate probes hybridizing next to each others in a target sequence (proximity probe approach) enabling the label moieties to form a fluorescent complex.

The principle of lanthanide chelate complementation directed by oligonucleotide hybridization is illustrated in FIG. 2. One oligonucleotide probe (1) is labelled with a lanthanide ion carrier chelate (4) and another probe (2) with a light-harvesting antenna ligand (5). When a target nucleotide sequence (3) with adjacent complementary sequences to the two labelled probes is added (6), a double-stranded nucleic acid hybrid (7) is formed directing the self assembly of the mixed chelate and formation of a highly fluorescent complex (8). The probe sequences (including conjugation site for linker) and linkers (length and composition, including orientation and rigidity) are selected so that the two parts of the reporter, i.e. the ion carrier chelate and the antenna ligand, are brought to close proximity at correct orientation to enable self assembly of the mixed chelate. When the complex is formed fluorescence is excited at one wavelength ($\lambda_1$) and the emission is measured at another wavelength ($\lambda_2$) at the same time or, in time-resolved fluorometry, after a short delay after excitation. This invention comprises combinations of lanthanide chelates and ligand structures coupled to separate oligonucleotides and their use in an improved oligonucleotide-directed lanthanide chelate complementation assay. The inventors have found that the oligonucleotide-directed lanthanide chelate complementation provides an enormous potential to be explored. Previously employed chelates, ligands and conditions have been selected with best knowledge, but provided a weak performance (less than 3-fold signal modulation) [Oser, A and Valet, G (1990) *Angew Chem Int Ed Engl* 29: 1167-1169; Wang, G L et al. (2001) *Anal Biochem* 299: 169-172; and U.S. Pat. No. 6,242,268]. Obtained degree of modulation in all previous examples has been very modest (less than 3-fold), i.e. the switching of the lanthanide fluorescence has been incomplete due to significant and easily observable background fluorescence from the dark state of the reporter system, and no improvement has been disclosed during the years. The inventors have now observed that this fluorescence modulation can be enhanced up to over 1000-fold by selecting an appropriate combination of light-harvesting antenna ligand, ion carrier chelate and optionally an additional ion chelating compound. This is an enormous improvement, as typical best modulation obtained with conventional FRET type hybridization assays is around 20-fold and only 3-fold modulation has been previously obtained based on formation of a mixed lanthanide chelate complex. In lanthanide chelate complementation assays high degree of modulation is achieved through utilization a strict requirement of chelate complementation for signal generation. The improvements result in that essentially no free lanthanide ion is present in solution available to form fluorescent complexes with multiple antenna ligands. The inventors have found that these improvements are also essential for allowing chelate complementation assays with high degree of modulation to be employed at elevated temperatures, e.g. at conditions prevailing during polymerase chain reaction.

The complex mechanism of lanthanide excitation could be considered the springboard for the present invention of a novel complementing lanthanide-based reporter system: the non-fluorescent lanthanide(III) chelate (ion carrier chelate) is switched to highly fluorescent form by complementing the chelate complex with an additional light-harvesting antenna ligand. For the proximity probe principle-based assay, the carrier chelate (containing the ion) and the antenna ligand are coupled to two different biomolecular binding probes (e.g. oligonucleotides), which do not interact in solution at (sub-micromolar) concentrations generally used in bioanalytical assays and thus no fluorescence is observed upon excitation (the reporter is at dark state). However, when the two probes are, as a result of simultaneous recognition of target molecule (e.g. complementary nucleic acid sequence), brought to closely proximal positions, the antenna ligand is coordinated to the lanthanide ion in the carrier chelate (forming a mixed chelate) and the lanthanide ion produces strong fluorescence upon excitation (the reporter is switched to fluorescent state). Complementation of the carrier chelate with the antenna ligand requires molecular contact at correct orientation between the antenna ligand and the central lanthanide ion. The process is actually self-assembling, as high effective local concentration favours binding even through weak coordination interactions, when both the carrier chelate and the antenna ligand are anchored into close proximity.

According to the invention the ion carrier chelate has to be designed to strongly bind the lanthanide ion; i.e. to form a both thermodynamically and kinetically stable complex with a high stability constant; preferred coordination degree (dentate number) is over five and preferably higher such as six or seven of the total nine coordination sites of the lanthanide ion, thus leaving, at least one, but preferably two or three coordination sites for binding of the antenna ligand. The stability of the ligands increases e.g. in series EDTA, DTPA, DO3A, DOTA (most stable). In absence of the antenna ligand, the free coordination sites of the lanthanide ion are occupied by water molecules, efficiently quenching any residual lanthanide fluorescence. The antenna ligand, however, must have only a weak binding strength; the suitable coordination degree is most likely two or three (referring to bidentate or tridentate ligands) and the suitable structures are e.g. individual light-harvesting ligands described in a recent patent application [WO 2005/021538] for construction of azacrown-based triple-antenna chelates. The preferred structure of the organic light-harvesting ligand (triplet state energy level) is dependent on the lanthanide, and thus, different antenna ligands are preferred for e.g. terbium(III) and europium(III) ions.

According to the invention the signal is strictly dependent on the proximity of the ion carrier chelate and the antenna ligand, and to achieve the high specificity of chelate complementation the concentration of the free lanthanide ion is kept minimal by selecting appropriately the ion carrier chelate or by adding a complexing agent to chelate the free lanthanide ion in order to avoid formation of fluorescent complexes not comprising the ion carrier chelate. Preferably the complexing agent is chosen to be selective to the lanthanide ion. The inventors have observed, that binding of the light-harvesting antenna ligand to the ion carrier chelate (and also to the ion chelated by the complexing agent) is more difficult than binding to the free ion, and thus it is essential to keep the concentration of the free lanthanide ion minimal to render signal generation strictly specific and dependent only on the chelate complementation controlled by biomolecular binding and proximity of the ion-carrier chelate and the antenna ligand.

The combination of the ion carrier chelate and the antenna ligand is selected so that the ion carrier ligand is a multidentate ligand that forms a stable (or very stable) complex between the lanthanide ion leaving at least one (but preferably not more than four) of the coordination sites unoccupied, thus enabling the binding of the antenna ligand and formation of a complex, where preferably all coordination sites of the lanthanide are occupied by either of the ligands, thus replacing the coordinated water molecules. The combination can be selected so that complete binding of the antenna ligand may optionally require displacement of one or two dentates of the carrier ligand, but preferably not result in dissociation of the lanthanide ion from the ion carrier chelate.

In case the ion carrier chelate is not very stable, some dissociation of the lanthanide ion may occur at conditions prevailing during the assay and according to the invention in such cases a complexing agent is present in solution to complex the free lanthanide ions preventing formation of fluorescent complexes between the free lanthanide ion and the antenna ligand. The inventors have discovered that this results in an enormous improvement in the assay performance over prior art. This can be explained e.g. due to formation of highly fluorescent multiligand complexes between the antenna ligand and the lanthanide ion, i.e. a single free lanthanide ion can bind to up to three or four antenna ligands, producing a complex which is significantly more fluorescent than a single mixed chelate complex formed by chelate complementation of the lanthanide ion carrier chelate and the antenna ligand. The inventors have now discovered how to provide complete switching of lanthanide fluorescence by chelate complementation and essentially solve this background fluorescence problem, which is present in prior art methods.

According to a preferred embodiment of the invention, the lanthanide ion carrier chelate is selected to be an inert complex, i.e. the dissociation of the lanthanide ion from the complex should be slow at the conditions prevailing during the assay. It is known that the presence of other ions and complexing agents in the aqueous solution and increased temperature will typically result in increased dissociation of the coordination complexes, and thus for certain applications, e.g. real-time monitoring of polymerase chain reaction, it is essential to select a very stable ion carrier chelate providing a slow dissociation rate even at elevated temperature. Typically the lanthanide ion carrier chelate and the antenna ligand are employed at submicromolar concentrations, further increasing the importance of the stability and especially slow dissociation rate of the complex. The lanthanide ion carrier chelates containing ionic macrocyclic chelate structures such as derivatives of 1,4,7-tris(carboxymethyl)-1,4,7,10-tetraazacyclodedecane (DO3A) [Mishra, A. et al. (2005) *Proc. Intl. Soc. Mag. Reson. Med.* 13: 2592] are preferred over ionic linear open chain chelate structures for the inert lanthanide ion carrier chelate to provide slow dissociation rate [Morcos, S. K. (2007) *The British Journal of Radiology* 80: 73-76] at extreme conditions prevailing during some bioassay applications. According to one embodiment the lanthanide ion carrier chelate is selected to provide kinetic stability with dissociation half life at prevailing assay conditions over 2 h, preferably over 10 h and most preferably over 24 h; e.g. estimated dissociation half life of certain macrocyclic chelates at physiological conditions can be several years [Schmitt-Willich, H. (2007) *British Journal of Radiology* 80: 581-582]. Typical bioassay conditions have a pH near neutral value, e.g. between 6.0-9.0, and have an ionic strength between 0.01 M and 1 M. Typical prevailing temperature in bioassays is 20-40° C., but certain applications require temperatures up to 100° C. The thermodynamic and kinetic stability of both macrocyclic and open chain gadolinium(III) chelates has been described by Port M. et al. (2008) *Biometals* 21: 469-490. The macrocyclic compounds such as DO3A and DOTA have showed significantly slower dissociation of the ion than open-chain chelates such as DTPA. In addition, the ionic chelates (negative net charge) have had better stability than non-ionic ones (neutral net charge).

According to a further embodiment of the present invention, an additional, weakly binding quencher ligand can be added into the bioassay solution to replace coordinated water from the lanthanide ion present in the ion carrier chelate and quench the potentially remaining fluorescence of the lanthanide ion carrier chelate not participating in chelate complementation. The quencher ligand would be selected to be monodentate, bidentate or tridentate, and so that it is quickly replaced by the antenna ligand brought into close proximity by biomolecular binding event.

According to yet another embodiment of the present invention, more than one different antenna ligand is employed in combination with one or multiple ion carrier chelates still containing the same lanthanide, resulting in different mixed chelate pairs producing their characteristic luminescence lifetimes enabling measurement of additional parameters.

According to some preferred embodiments of the present invention the ratio of the conditional stability constants of the complex formed by the lanthanide ion carrier ligand and the lanthanide ion and the complex formed by the antenna ligand and the lanthanide ion is at least $10^4$, preferably at least $10^5$, and more preferably at least $10^6$, under the conditions of the analyte determination; i.e. the complex formed by the lanthanide ion carrier ligand and the lanthanide ion is significantly more stable.

DEFINITIONS

The term "fluorescence" and "luminescence" shall be understood to cover photoluminescence, i.e. luminescence excited by light, fluorescence, including delayed fluorescence with microsecond or millisecond fluorescence lifetime, ionic photoluminescence, up-conversion based anti-Stokes photoluminescence, and phosphorescence. In addition, the term shall cover electrogenerated luminescence and electrochemiluminescence.

The term "lanthanide" and "lanthanide ion" shall be understood here to be equivalent to "rare earth metal ion" and to include single trivalent lanthanide ions and any combination of several different lanthanide elements from the following: neodymium, praseodymium, samarium, europium, promethium, gadolinium, terbium, dysprosium, holmium, erbium, thulium, ytterbium and yttrium, especially erbium, praseodymium, thulium, and ytterbium.

In this disclosure the terms "luminescent lanthanide complex", "luminescent lanthanide chelate" and "complemented lanthanide chelate" shall be understood to include luminescent complexes formed by a lanthanide ion carrier chelate and complementing light-harvesting antenna ligand, where the lanthanide ion is excited through a light-harvesting or other excitable ligand structure or a non-luminescent lanthanide ion or a sensitizer lanthanide ion. Complemented lanthanide chelate is an example of a mixed chelate comprising a ion carrier chelate and a light-harvesting antenna ligand.

The term "lanthanide ion carrier chelate", "ion carrier chelate" and "carrier chelate" shall be understood to include as such non-luminescent lanthanide chelate complexes and their derivatives, which comprise a chelating ligand, i.e. ion carrier ligand, and a luminescent lanthanide ion or an activator lanthanide ion, but which do not comprise efficient light-harvesting or other excitable structure or sensitizer lanthanide ion essential to lanthanide luminescence. The lanthanide ion in the chelate can be one single lanthanide ion or a combination of several identical or different lanthanide ions. Examples of lanthanide ion carrier chelates represent cyclic or non-cyclic aminopolycarboxylic acid chelates of Eu(III), Sm(III), Tb(III) and Dy(III), with a coordination number preferably equal to or more than 6 dentates, optimally 7 or 8, but which do not contain efficient light-harvesting or other excitable structure or sensitizer lanthanide ion.

The terms "sensitizer" and "sensitizer lanthanide ion" shall be understood to mean the lanthanide ion responsible for light absorption and acting as energy donor to activator lanthanide ion, which acts as energy acceptor. Example of a sensitizer is trivalent ytterbium and cerium.

The terms "activator" and "activator lanthanide ion" shall be understood to mean the ion responsible for luminescence emission and acting as energy acceptor, accepting energy from the sensitizer lanthanide ion, which acts as an energy donor. Examples of activators are trivalent erbium, thulium, holmium, and terbium. The "stability constant" and "formation constant" of the complex between the ion carrier ligand and the lanthanide ion (or the complex between the antenna ligand and the lanthanide ion; or the complex between the complexing agent and the lanthanide ion) in aqueous solution shall be understood to mean the equilibrium constant for the complexation reaction between ligand and metal ion. Detailed explanation of the term can be found on pp. 279-304 in Quantitative Chemical Analysis, D. C. Harris, 1991, 3rd Edition, Freeman and Co., New York. The value is expressed as log K, where K can be calculated by dividing the concentration of the complex by the product of concentrations of the free ligand (typically fully deprotonated form) and the free metal ion, all prevailing at equilibrium state at certain temperature and ionic strength. The larger the value of the stability constant, the stronger the metal is complexed with the ligand. This implies that lanthanide ion carrier chelates with large stability constants are more stable than those with smaller stability constant. Typically stability constants are measured at room temperature (20-25° C.) and at ionic strength of 0.1 M. Examples of log K values for lanthanide (III) ion complexes can be found from Martell, A. E. and Smith, R. M., Critical stability constants, Vol 1, pp. 204-211, Plenum Press, New York, 1974; and Wu, S L and Horrocks, W D (1997) Journal of the Chemical Society-Dalton Transactions 1497-1502.

The "conditional stability constant" and "conditional formation constant" and "effective formation constant" of the complex between the ion carrier ligand and the lanthanide ion (or the complex between the antenna ligand and the lanthanide ion) in aqueous solution shall be understood to mean the equilibrium constant for formation of a complex under a particular stated set of conditions, such as pH, ionic strength, temperature and concentration of auxiliary complexing species. Detailed explanation of the term can be found on pp. 279-304 in Quantitative Chemical Analysis, D. C. Harris, 1991, 3rd Edition, Freeman and Co., New York.

The term "complementing ligand", "light harvesting antenna" or "antenna ligand" shall be understood to include as such non-luminescent chelating ligands and lanthanide chelates and their derivatives, which comprise a light-harvesting or other excitable ligand structure without a lanthanide ion or chelate complexes of a non-luminescent lanthanide ion or a sensitizer lanthanide ion, and which are capable of complementing a lanthanide ion carrier chelate to form a luminescent lanthanide complex. The lanthanide ion optionally included in the antenna ligand can be one single lanthanide ion or a combination of several identical or different lanthanide ions. Examples of such lanthanide ions utilized to enhance light-absorption or emission intensity in co-fluorescence phenomenon or lanthanide-based upconversion are e.g. Gd(III), Y(III) and Yb(III). Examples of antenna ligands [Latva, M. (1997) J. Lumin 75: 149-169] are organic light-harvesting structures able to coordinate to lanthanide ions preferably with 4 dentates or less, optimally with 3 to 2 dentates and can transfer their excitation energy typically through triplet state to coordinated lanthanide ions such as Eu(III), Sm(III), Tb(III) and Dy(III). Examples of antenna ligand structures suitable for near-infrared emitting lanthanides, such as Yb(III), Er(III) and Nd(III), have also been described [Hofstraat, J. W. et al. (1998) *J Fluorescence* 8: 301-307].

The terms "non-luminescent" and "non-fluorescent" shall be understood as a property of a light absorbing compound not to produce any or a significant amount of a desired type of luminescence, e.g. long lifetime luminescence, when excited and relaxing from the excited state. In contrast to luminescent compounds, the excited-state energy of a non-luminescent compound is predominantly relaxed via non-radiative pathways, typically producing heat instead of light, or rapid emission instead of slowly decaying emission or the excitation efficiency is weak. The molar extinction coefficient or molar absorptivity of a non-luminescent compound is very low, typically below $10\,L\,mol^{-1}cm^{-1}$, or the fluorescence quantum yield of a non-luminescent compound is very poor, typically below 5 percent, or the lifetime of long-lifetime luminescence is shorter than 1 microsecond, typically less than 100 nanoseconds. Examples of non-luminescent compounds are lanthanide chelates, which do not contain a light-harvesting antenna structure for their efficient excitation.

The term "lanthanide luminescence" and "luminescence" shall be understood to mean luminescence (i.e. light emission) obtained from emissive relaxation of electronic transitions of lanthanide ion. Lanthanide luminescence can be generated by excitation of the lanthanide ion by direct or indirect light absorption or by electrogenerated chemical excitation.

The term "chelate" is defined as a coordination complex where a single central ion is coordinated (or multiple central ions are coordinated) to at least one ligand with at least one coordination bond (each). These complexes may be named by different principles, and names like chelates, supramolecular compounds, complexes and complexones are used. Special types of chelates include e.g. polyaminocarboxylic acids, macrocyclic complexes, crown ethers, cryptates, calixarenes and phorphyrins. The term "mixed chelate" shall be understood as a chelate comprising at least two different ligands coordinated with at least one coordination bond each.

The terms "time-resolved lanthanide fluorescence", "time-resolved fluorescence", "long-lifetime lanthanide luminescence" and "long-lifetime fluorescence" shall be understood here as lanthanide luminescence, where a luminescence lifetime of the luminescent compound is equal to or more than 1 microsecond (the lifetime being calculated as the time wherein luminescence emission intensity decays to the relative value of 1/e, i.e. to approximately 37% of the original luminescence emission intensity). Examples of compounds capable of long-lifetime fluorescence include, but are not limited to, intrinsically fluorescent chelate complexes of Eu(III), Sm(III), Tb(III) and Dy(III) containing appropriate light-harvesting antenna.

The terms "light", "excitation light" and "emission light" shall be understood to cover electromagnetic radiation at wavelengths from 200 nm to 1600 nm. These wavelengths are called ultraviolet light below 400 nm, near-ultraviolet light between 300-450 nm, visible light between 400-750 nm, near-infrared light between 700-1000 nm and infrared light above 700 nm.

The term "short-lifetime fluorescence" and "short-lifetime fluorescent compound" shall be understood to cover fluorescence and fluorescent compounds with a luminescence lifetime of less than 1 microsecond, preferably less than 100 nanoseconds.

The terms "lanthanide up-conversion", "up-conversion" and "anti-Stokes photoluminescence" shall be understood here as lanthanide luminescence, where photoluminescence emission from luminescence lanthanide compound is obtained at shorter wavelength than the wavelength of excitation light. Up-converting luminescent lanthanide compounds can thus convert lower energy incident light to higher energy emitted light. It is also called anti-Stokes fluorescence or anti-Stokes photoluminescence. Examples of such compounds are entirely inorganic or hybrid materials containing Er(III) as activator and Yb(III) as sensitizer producing green or red emission under infrared excitation.

The terms "electrogenerated luminescence" and "electrochemiluminescence" shall be understood here as lanthanide luminescence produced by electrogenerated chemical excitation using an electrode and applying electric current or voltage to the electrode. Depending on the electrode where the electrochemical reaction producing luminescence occurs the electrochemiluminescence is called cathodic or anodic electrochemiluminescence. Electrogenerated luminescence compounds are compounds capable of anodic or cathodic electrogenerated luminescence. An example of such a compound is hot electron excited 2,6-bis[N,N-bis(carboxy-methyl)-aminomethyl]-4-benzoyl phenol-chelated Tb(III) producing green emission [Kulmala, S. and Haapakka, K. (1995) *J Alloys Comp* 225: 502-506] but other lanthanide complexes capable of electrogenerated luminescence exist [Kulmala, S. et al. (1998) *Anal Chim Acta* 359: 71-86; and Jiang, Q. et al. (2006) *Anal Chim Acta* 558: 302-309]. Electrogenerated luminescence of lanthanide complexes can also be measured using temporal resolution to improve limit of detection.

In this disclosure, the term "bioassay" shall be understood to refer to detection and/or quantitation of analyte based on lanthanide luminescence and utilizing reaction elements. The analyte is typically detected and/or measured from a sample or an aliquot of sample, which sample is e.g. a biological or environmental sample or a nucleic acid amplification reaction.

The term "homogeneous bioassay" shall be understood to cover bioassays requiring no separation steps. Single or multiple steps of each; addition of reagents, incubation and measurement are the only steps required. The term "separation step" shall be understood to be a step where a labelled bioassay reagent bound onto a solid-phase, such as for example a microparticle or a microtitration well, is separated and physically isolated from the unbound labelled bioassay reagent; for example the microtitration well is washed (liquid is taken out and, to improve the separation, additional liquid is added and the well emptied) resulting in separation of the solid-phase bound labelled bioassay reagent from the labelled bioassay reagent not bound onto the solid-phase.

The term "analyte" shall be understood as a substance of interest, which is to be measured or the effect of which is to be measured by the bioassay. Analyte can be e.g. protein, cell, cell membrane antigen, receptor, nucleic acid, hapten, hormone, peptide, oligonucleotide, product of nucleic acid amplification, specific conformational form of a molecule or change in structure, such as cleavage through protease or nuclease activity, or multimerization of structural subunits, association of two biomolecules through molecular binding interactions, or their dissociation.

The term "hapten" shall be understood to refer to a small molecule, which can elicit an immune response only when attached to a large carrier such as a protein. Examples of haptens are steroid hormones, vitamins, peptides, saccharides, medicaments and drugs of abuse.

The terms "sample" and "biological sample" shall be understood to cover various liquid or solid biological samples whereof the analyte is detected, such as serum, blood, plasma, saliva, urine, faeces, seminal plasma, sweat, liquor, amniotic fluid, tissue homogenate, ascites, samples from environmental studies (water and soil samples), industrial processes (process solutions) and compound libraries (screening libraries which may comprise organic compounds, inorganic compounds, natural products, extracts or results of purification of biological sources containing biological proteins, peptides, or nucleic acids). The sample can also be an enzyme reaction, such as protease or nuclease reaction, or other conversion reaction, polymerase chain reaction or other nucleic acid amplification reaction.

The term "recognition element" refers to any reactant that can be considered to be specific to any compound of relevance in the circumstances referred to and it shall be understood to cover biospecific binding reactants such as antibodies, antibody fragments, protein scaffolds (e.g. darpins, affibodies, monobodies), peptides, aptamers, natural hormone binding proteins, saccharides, lectins, enzymes, receptors, streptavidin, biotin, natural and artificial nucleic acids (such as locked nucleic acids or peptide nucleic acids) and peptide derivatives, and genetically or chemically engineered antibodies, or chimeric compositions of any of the preceding, which can non-covalently or covalently bind and recognize biomolecules to be detected. The recognition elements are typically employed as biospecific binding reactants in immunoassays, nucleic acid hybridization assays, ligand-lectin assays and ligand-receptor assays.

The terms "complexing agent", "agent complexing" and "chelating agent" should be understood in this context as molecules, which can form several coordinate bonds with a single metal ion, i.e. they are polyvalent ligands. The most common and most widely used complexing agents are those that coordinate to metal ions through oxygen or nitrogen donor atoms, or through both. Examples of complexing agents are nitrilotriacetic acid (NTA), ethylenediaminetetraacetic acid (EDTA), diethylenetriaminepentaacetic acid (DTPA) ethyleneglycol-O—O'-bis(2-aminoethyl)-N,N,N',N'-tetraacetic acid (EGTA), 1,4,7-triazacyclononane-N,N',N''-triacetic (NOTA), 1,4,7,10-tetraazacyclododecane-N,N',N'',N'''-tetraacetic acid (DOTA), cyclohexyl 1,2-diamine tetra-acetic acid (CDTA), $N_1N'$-bis(hydroxybenzyl)-ethylenediamine-N,N'-diacetic acid (HBED), triethylene tetramine hexa-acetic acid (TTHA), 1,4,8,11-tetraazacyclotetradecane-N,N',N'',N'''-tetraacetic acid (TETA), hydroxyethyldiamine triacetic acid (HEDTA) and derivatives of any of these chelators.

The term "up-converting lanthanide complex" in this context means a mixed chelate comprising a single lanthanide ion or a combination of different rare earth ions. The antenna ligand may or may not contain a sensitizer lanthanide ion and/or light harvesting structure.

Preferred Embodiments of the Invention

A typical bioassay method for detecting analyte and/or quantifying analyte concentration according to the invention employs a first group comprising a lanthanide ion carrier chelate and a first recognition element, wherein said lanthanide ion carrier chelate comprises a lanthanide ion carrier ligand and a lanthanide ion; a second group comprising an antenna ligand and a second recognition element; wherein
  a) said lanthanide ion carrier chelate binds, in the conditions prevailing in said bioassay method, strongly enough to said lanthanide to result in that essentially no, i.e. less than 1 nmol/L, preferably less than 10 pmol/L, free lanthanide ion is present in the conditions prevailing in said bioassay method; or b) said lanthanide ion carrier chelate binds, in the conditions prevailing in said bioassay method, strongly enough to said lanthanide, to result in that essentially no, i.e. less than 1 nmol/L, preferably less than 10 pmol/L, free lanthanide ion is present and an agent complexing said lanthanide ion at a concentration of at least 1 pmol/l is additionally employed; and said antenna ligand binds weakly to said lanthanide ion, i.e. said antenna ligand is either monodentate, bidentate, tridentate or tetradentate; and wherein recognition of said analyte by said first recognition element of said first group and by said second recognition element of said second group results in either i) chelate complementation, i.e. formation of a mixed lanthanide chelate complex through complementation of said lanthanide ion carrier chelate carrying said lanthanide with said antenna ligand, and accordingly in increased fluorescence; or ii) chelate discomplementation, i.e. said lanthanide ion carrier chelate carrying said lanthanide is separated from said antenna ligand, and accordingly in decreased fluorescence.

In preferred embodiments of the bioassay a) log $K_{LnL1}$ is at least 12, preferably over 18, wherein $K_{LnL1}$ refers to the stability constant of the complex between the ion carrier ligand and the lanthanide ion in solution; or b) when the agent complexing said lanthanide ion is further employed i) log $K_{LnL2}$ is at least 12, wherein $K_{LnL2}$ refers to the stability constant of the complex between the ion carrier ligand and the lanthanide ion in solution; and ii) log $K_{LnL3}$ is at least 8, wherein $K_{LnL3}$ refers to a stability constant between said complexing agent complexing said lanthanide ion and the lanthanide ion in solution.

In typical embodiments of the invention the ion carrier chelate is pentadentate, hexadentate, heptadentate or octadentate, preferably hexadentate, heptadentate or octadentate.

The lanthanide ion of the ion carrier chelate is preferably selected from the group consisting of praseodymium(III), neodymium(III), samarium(III), europium(III), terbium(III), dysprosium(III), holmium(III), erbium(III), thulium(III) and ytterbium(III).

The first and second recognition elements are preferably independently of each other selected from the group consisting of oligonucleotides, aptamers, peptides, proteins, haptens, oligosaccharides.

The antenna ligand is typically tetradentate, tridentate, bidentate or monodentate, preferably tridentate or bidentate.

log $K_{LnL1}$ is typically at least 20, preferably over 22.

The complexing agent is preferably selected from the group consisting of CDTA, EDTA, DOTA, DTPA, EGTA, HBED, HEDTA, NOTA, NTA, TETA and TTHA.

When an agent complexing the lanthanide ion is employed said complexing agent is typically a stronger binder of said lanthanide ion than the antenna ligand, i.e. log $K_{LnL3}$>log $K_{LnL4}$, wherein $K_{LnL4}$ refers to the stability constant of the complex between said antenna ligand and said lanthanide ion in solution; and preferably a weaker binder of the lanthanide ion than the ion carrier chelate, i.e. log $K_{LnL3}$<log $K_{LnL2}$.

The lanthanide ion carrier ligand is typically derived from EDTA, DTPA, NOTA or DOTA, or selected from the structures a) to p) presented in FIGS. 7/i, 7/ii and 7/iii.

The antenna ligand typically comprises a light harvesting structure selected from the group consisting of structures a) to z) illustrated in FIGS. 5/i, 5/ii, 5/iii and 5/iv.

The recognition of the analyte results in increase or decrease of fluorescence and said fluorescence is typically measured at a wavelength between 400 and 1600 nm.

The analyte detected and/or quantified is typically selected from the group consisting of streptavidin, protein, hapten, nucleic acid sequence, cells, viruses and product of nucleic acid amplification reactions, e.g. product of polymerase chain reaction.

The recognition of the analyte results in increase or decrease of fluorescence and typically said fluorescence has a long fluorescence lifetime, i.e. a lifetime >1 µs.

The recognition of the analyte results in increase or decrease of fluorescence and preferably said fluorescence is upconversion fluorescence (i.e. anti-Stokes photoluminescence wherein emission is detected at a shorter wavelength than excitation).

In many preferred embodiments the prevailing conditions comprise a temperature of at least 40° C. or higher.

According to one embodiment of the invention, lanthanide-based reporter technology is applied in hybridization assays and real-time "closed-tube" monitoring of nucleic acid amplification; e.g. polymerase chain reaction, ligase chain reaction or some isothermal nucleic acid amplification procedure [Gill, P. and Ghaemi, A. (2008) *Nucleosides Nucleotides Nucleic Acids* 27: 224-243]. The biomolecular binders are e.g. oligonucleotides or oligonucleotide analogues such as peptide nucleic acids (PNA) or locked nucleic acids (LNA).

The principle of oligonucleotide-directed lanthanide chelate complementation assay for homogenous nucleic acid hybridization assays is described in FIG. 2; this principle enables an assay based on two probes (hybridized next to each other) to be performed without utilizing FRET. One of the probes is labelled with a non-fluorescent lanthanide chelate (4) and the other with complementing antenna ligand (5) coupled to suitable organic light-harvesting structure; together the chelate and the ligand are able to form a fluorescent lanthanide complex. According to other embodiments of the invention, the method can be further extended to padlock or molecular beacon type probes as described in FIG. 3 and FIG. 4 respectively.

Figure 3:
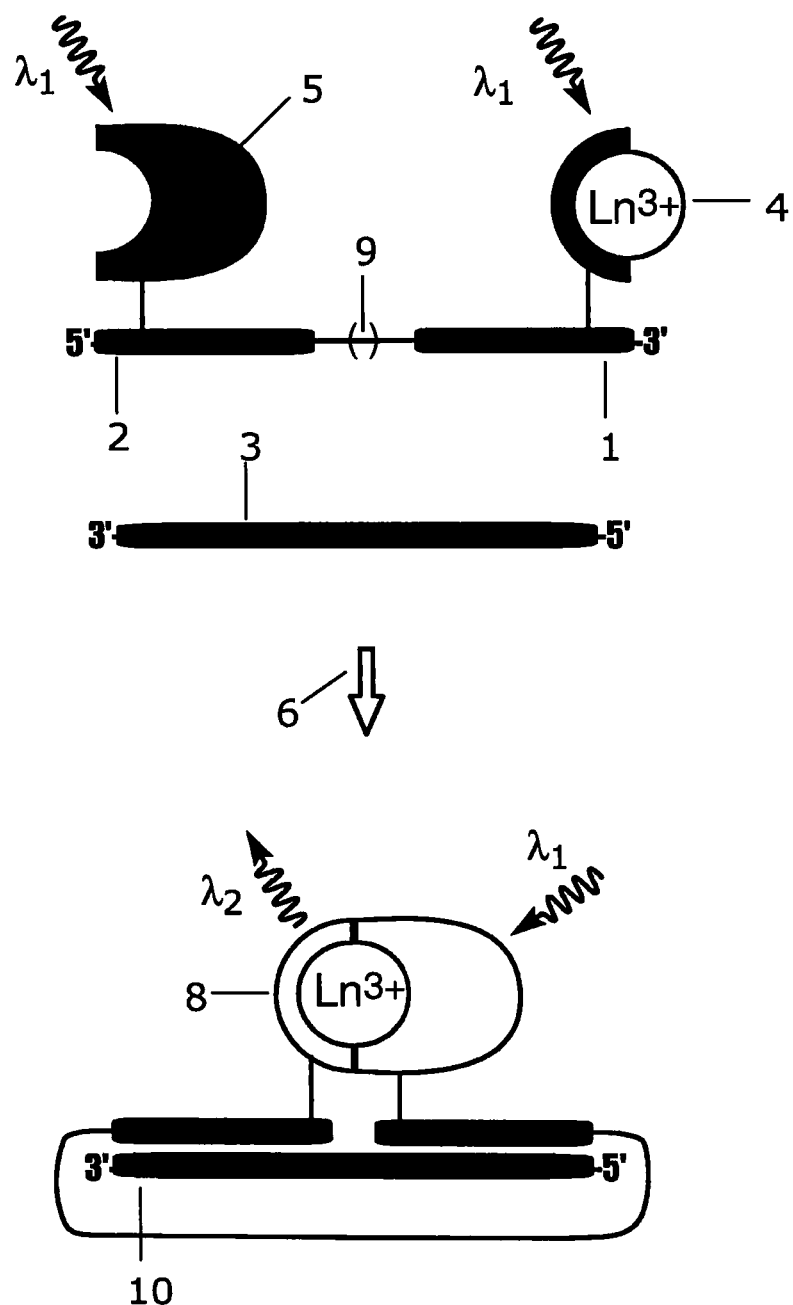
FIG. 3 illustrates an oligonucleotide-directed lanthanide chelate complementation assay using a dual-labelled probe with terminal ends hybridizing next each others in a target sequence (padlock type probe) enabling the label moieties to form a fluorescent complex.

In FIG. 3 the padlock type probe is composed of two terminal oligonucleotide sequences connected with a linker (9) (e.g. an oligonucleotide sequence), and one terminal sequence (1) is labelled with an lanthanide ion carrier chelate (4) and the other terminal sequence (2) with a light-harvesting antenna ligand (5). When a target nucleotide sequence (3) with adjacent complementary sequences to the two labelled terminal ends is added (6), a double-stranded nucleic acid hybrid (10) is formed directing the self assembly of the mixed chelate and formation of a highly fluorescent complex (8). The formation of complex results in increased fluorescence at emission wavelength ($\lambda_2$) excited at excitation wavelength ($\lambda_1$).

Figure 4:
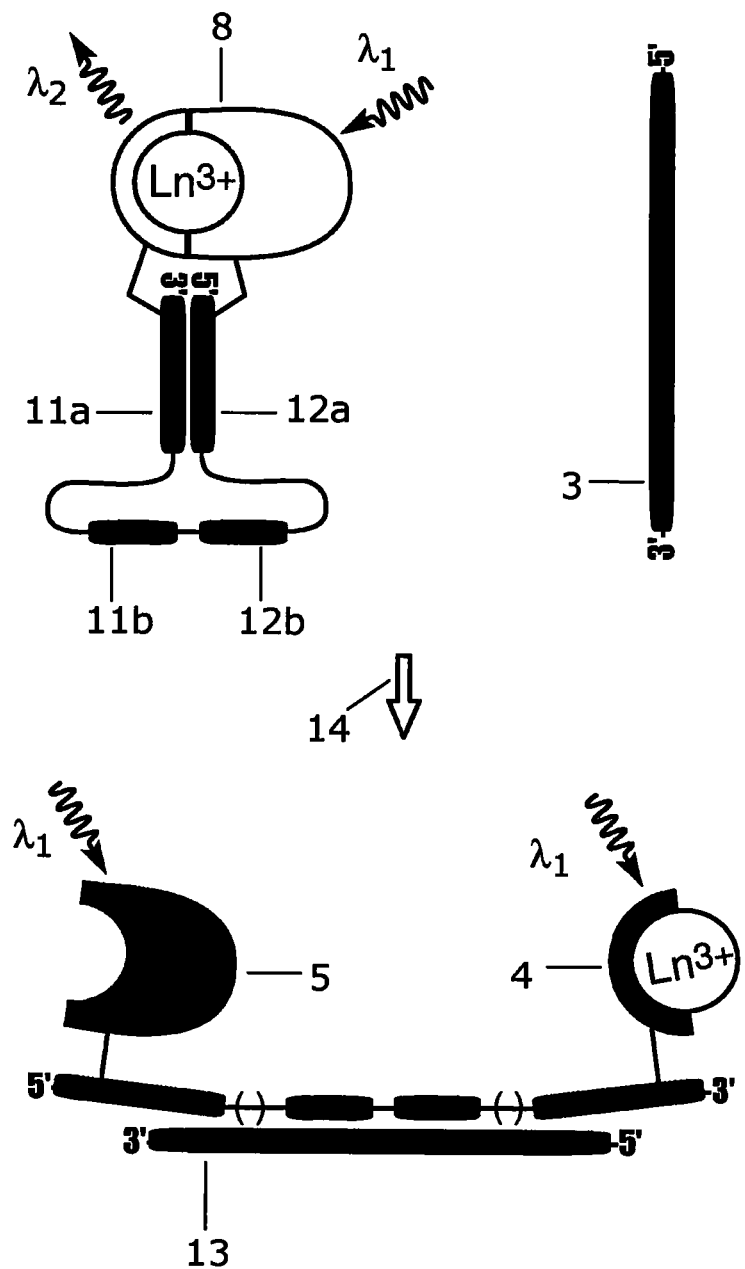
FIG. 4 illustrates an oligonucleotide-directed lanthanide chelate complementation assay using a dual-labelled probe with terminal ends having complementary sequences hybridized to each other (molecular beacon type probe) enabling the label moieties to form a fluorescent complex. The middle sequence hybridizes to a target sequence resulting in a conformational change of the probe that takes apart the fluorescent complex and resulting in decrease of fluorescence.

FIG. 4 illustrates a hybridization assay utilizing molecular beacon type probe, where the labelled probe, in addition to analyte specific sequences (11b and 12b) contains two complementary sequences (11a and 12a) which, in absence of analyte sequence (3) bring the two parts of the chelate, antenna ligand (5) and ion carrier chelate (4) coupled near to the complementary sequences, in close proximity allowing the chelate complementation and formation of a fluorescent complex (8). When the analyte sequence (3) is brought to the solution (14) the analyte specific sequences recognize their complementary sequences forming a partial double stranded duplex (13) which takes the mixed chelate apart and results in reduced fluorescence at emission wavelength ($\lambda_2$) excited at excitation wavelength ($\lambda_1$).

According to another embodiment of the invention, the reporter technology is applied in protein detection and in measurement of protein-protein interactions. In these applications the control of the orientation and distance between the two probes can utilize natural ligands, short binding peptides, or artificial binders designed de novo and/or enriched from molecular binder libraries together with site-specific coupling chemistries. The invention is especially well suitable to detection of multimeric proteins and multimeric protein complexes, including e.g. virus capsid proteins and C-reactive protein as described for molecular pincers [Heyduk E, et al. (2008) Anal Chem. 80: 5152-5159].

According to one embodiment of the invention, the method is applied to detection of protein dimerization (or multimerisation) induced by e.g. change in ion concentration or presence of an analyte or small molecule ligands such as antibiotics or steroids. Example of such an event is calcium ion dependent protein dimerization [Appelblom H, et al. (2007) J Biomol Screen 12: 842-8]. The dimerization can be either formation of hetorodimer or homodimer. Another example has been described utilizing the antigen-dependent reassociation of antibody variable domains [Ueda, H. (2003) J Immunol Methods 279: 209-218].

According to the invention both the carrier chelate and the antenna ligand are covalently attached to the biomolecular binder using e.g. iodoacetamide, N-hydroxysulfosuccinimide, maleimide or isothiocyanate activation. For construction of the biomolecular probes the reporter moieties are conjugated e.g. to oligonucleotide binders comprising e.g. a single amino modified base or terminal amino modification. In case of recombinant protein binders comprising several amino groups (lysine residues), site-specific conjugation can be obtained through thiol groups (additional cysteines) or by "click-chemistry" approaches [Beatty, K E et al. (2005) J Am Chem Soc 127: 14150-14151; Hahn, M E and Muir, T W (2005) Trends Biochem Sci 30: 26-34]. The covalent conjugation of the carrier chelate and the antenna ligand can also be carried out utilizing a specifically designed building block in solid-phase nucleic acid or peptide synthesis [Jaakkola et al. (2007) Solid-phase oligonucleotide labeling with DOTA. Current protocols in nucleic acid chemistry, edited by Beaucage, S. L. et al.; Chapter 14: Unit 4.31; online publication by John Wiley & Sons].

According to preferred embodiment of the invention, the biomolecular binder conjugate of the ion carrier chelate or the antenna ligand is carefully purified from unconjugated moieties and especially of the free ion potentially present in the reactive ion carrier chelate reagent. Examples of efficient methods of purification comprise reverse-phase, affinity and size-exclusion (or gel filtration) chromatography and dialysis. The extraction of the free ion can be improved by adding complexing agent to the probe solution before or while it is being purified. In oligonucleotide hybridization assays the reciprocal distance of the oligonucleotide probes and, in more detail, the actual labelled base positions and structure of the coupling linkers used for conjugation of the reporter moieties define how the carrier chelate and the antenna ligand are spatially located after the two probes are hybridized. If the double helix structure is rigid and the base positions of the two reporter moieties are too far away, or e.g. lengths of the coupling linkers are too short, the complementation may be hindered. In addition to the length and structure of the coupling linkers and the base positions, an additional non-hybridized single stranded sequence can be introduced into the template oligonucleotide between adjacent probe locations. This enables further balancing between freedom of movement and self-assembly of the mixed chelate.

According to yet another embodiment of the invention, reporter technology is employed in heterogeneous solid-phase proximity-probe principle-based assays, where non-specific binding of the reporters defines assay performance. By restricting signal generation only to those reporters present in the analyte bound probes and ignoring the reporters (or actually probes) that are non-specifically bound to solid-phase, the current performance limitation is resolved. The solid-phase assay can comprises e.g. the same oligonucleotide sequences and the same labelled probes than in a homogenous assay, but additionally utilizes e.g. a biotinylated template nucleic acid (analyte) and a streptavidin solid-phase (preferably a microtitration well) to capture the bound complexes. Instead of measuring the fluorescence from solution, the read-out is now from solid-phase after a wash step (separation of the unbound probes). The assay reflects the solid-phase proximity ligation assay [Fredriksson, S et al. (2002) Nat. Biotechnol. 20: 473-477; and Gullberg, M et al. (2003) Curr Opin Biotechnol 14: 82-86] and can provide potentially even more sensitive detection of the template oligonucleotide than the homogeneous model assay.

Protein detection is a more demanding application as the available binders do not as such provide easily predictable binding position or orientation, thus rendering the self-assembly of the complemented chelate more difficult to control. One embodiment of the invention utilizes recombinant antibody fragments, protein scaffolds (e.g. darpins, affibodies, monobodies), aptamers, peptide binders, ligands or haptens as binders combined with site-specific labelling to enable proximity probe based analysis of proteins utilizing lanthanide chelate complementation. Sensitive and specific proximity probe-based analysis of proteins and potential in medical diagnostics has been described by Gustafsdottir, S. M. (2005) Anal Biochem 345: 2-9 utilizing proximity ligation of two oligonucleotide probes.

Yet another embodiment of the invention utilizes protein or e.g. aptamer directed biomolecular recognition combined with oligonucleotide assisted self-assembly of the complementing lanthanide-based fluorescent reporter. The latter resembles the approach utilized in proximity ligation-based detection, where oligonucleotide tails attached to the protein or aptamer binders are connected in presence of short complementary oligonucleotide. The binder proteins can be derivatized with oligonucleotide tails, or more preferably produced as recombinant antibody fragments with weakly interacting leucine zippers [Ohiro, Y et al. (2002) Anal Chem 74: 5786-5792] or other interacting binder pair similarly to molecular pincers [Heyduk E, et al. (2008) Anal Chem. 80: 5152-5159], bearing the complementing lanthanide-chelate based reporter system. The random chemical conjugation on the antibodies is a potential problem, and recombinant antibody fragments and "click-chemistry" approaches can be utilized to enable site-specific conjugation.

Yet another embodiment of the invention is entirely protein directed self-assembly of the complementing lanthanide-based reporter, which requires molecular modelling based design, but provides improved performance. One approach is an analyte-driven controlled protein association and site-specific labelling with the complementing lanthanide-based reporter. The controlled protein association has been originally utilized for enzyme complementation with antibody Fv fragment heavy and light-chain domains [Ueda, H et al. (2003) J Immunol Methods 279: 209-218]. The interaction between heavy and light chain is artificially weakened, so that the association is dependent on the presence of the antigen. Site-specific labelling can be directed to additional cysteine residues introduced at the C-termini of the Fv domains. This approach, however, is not limited only to antibody structure, because ligand induced multimerization is a common phenomenon observed especially with regulatory proteins, which could be utilized as specific sensors for their natural ligands. Another, even more interesting approach is to utilize reporter-derivatized relatively short synthetic peptides as binders, which recognize adjacent positions on e.g. a multimeric protein analyte [Appelblom, H et al. (2007) *J Biomol Screen* 12: 842-848].

According to yet another embodiment of the invention, more than one different lanthanide ions are employed in separate ion carrier chelates combined with one or multiple light harvesting antenna ligands, thus enabling multiparametric assay designs.

According to yet another embodiment, the lanthanide ion carrier chelate and the antenna ligand can form an upconverting lanthanide complex. The collected energies of two or more photons are sequentially transferred from the antenna ligand by intramolecular non-radiative processes to the lanthanide ion in the carrier chelate, which thereafter emits a single photon of characteristic emission.

According to yet another embodiment of the invention, the fluorescence intensity of the complementing lanthanide-based reporters can potentially be enhanced by utilizing the co-luminescence phenomenon [Xu, Y Y et al. (1992) Analyst 117: 1061-1069; and Latva, M et al. (1995) J Chem Soc Perkin Trans 2 995-999].

Examples of preferred complementing light-harvesting antenna ligands containing the light harvesting structure are illustrated in FIG. 5/i-iv, a)-z). These structures comprise in addition weak metal chelating ligand and reactive group with optional linker/spacer enabling conjugation to molecular binders similarly as with the ion carrier chelate. Abbreviation X refers to the described chemical structure enabling conjugation of the lanthanide(III) ion carrier chelate to molecular binders, abbreviation -A- refers to a chemical linker or spacer sequence, abbreviation L refers to a chemical moiety independently selected from the schematic structures illustrated in FIG. 6, a)-h) and abbreviation -Z refers to a chemical moiety independently selected from FIG. 6, i)-I) or -Z is not present (i.e. it is replaced by hydrogen). Methoxy (—OMe) group included in structures FIG. 5/ii, i) and j) as well as FIG. 6, I) can be replaced with ethoxy (—OEt) group. In FIGS. 5/v, w)-z) the abbreviation -G refers to either —CF$_3$, —CF$_2$CF$_3$ or —CF$_2$CF$_2$CF$_3$. Typically the linker is composed of one or plurality of short aliphatic carbon chain, ether, carbonyl, amide, amine, ester thioether, and/or phenylene, and the reactive group is a chemical functionality, which may be, but is not limited to alcohols, thiols, carboxylic acids, primary or secondary amines, vinylsulfonyls, aldehydes, epoxides, hydrazides, succinimidyl esters, maleimides, alpha-halo carbonyl moieties (such as iodoacetyls), isocyanates, isothiocyanates, and aziridines. Preferably the chemical functionality is chosen from N-hydroxysuccinimides, isothiocyanate, maleimide, iodoacetyl and dichlorotriazine. Isothiocyanate activation can form an irreversible thiourea linkage with primary amino group of e.g. lysine amino acid, terminal amino of peptide or amino modification in oligonucleotide.

Typically the antenna ligand is a monodentate, bidentate, tridentate or tetradentate ligand, most preferably bidentate or tridentate ligand, the organic light harvesting structure contains aromatic rings or heterocycles, and the light-harvesting structures has a triplet state energy level appropriate for the trivalent lanthanide ion present in the ion carrier chelate. Examples of suitable triplet state energies and light-harvesting structures for lanthanide ions are presented in the literature [Latva, M. et al. (1997) J Luminescence 75: 149-169]. According to one embodiment of the invention, the light-harvesting organic structure is based on 7-amino-4-methyl-2 (1H)-quinoline (cs124), quinolone-like or coumalin-like structures [Li, M., and Selvin, P. R. (1997) Bioconj Chem 8.127-132; and U.S. Pat. No. 5,622,821].

Examples of preferred schematic structures for non-fluorescent lanthanide(III) ion carrier chelates suitable for complementation assay are illustrated in FIG. 7/i-iii, a)-p). These structures comprise metal a chelating ligand and a reactive group with an optional linker/spacer enabling conjugation to molecular binders such as peptides, proteins or nucleic acids via e.g. primary amino or thiol groups. Other conjugation chemistries including site-specific click-chemistry conjugation methods are also possible. Abbreviation Ln$^{3+}$ in the schematic structures refers to trivalent lanthanide ion and -X to reactive group enabling conjugation of the lanthanide(III) ion carrier chelate to molecular binders. In FIG. 7/i-iii, a)-p), abbreviation -A- refers to a linker or spacer e.g. alkyl chain containing 1-12 carbon atoms, and -X to a reactive group, e.g. amino, aminoxy, haloacetamido (where the halide is bromide or iodide), isothiocyanato, 3,5-dichloro-2,4,6-triazinylamino, maleimido, a thioester or an active ester of a carboxylic acid such as N-hydroxysulfosuccinimide. In FIG. 7/ii, f)-g) the value of n is either 1 or 2. Additional structures of ion carrier chelates for labelling of an oligonucleotide are illustrated e.g. in U.S. Pat. No. 6,949,639.

According to one embodiment of the invention, the ion carrier chelate contains one or a plurality of carboxylic acid groups as illustrated in FIG. 7/i-iii, a)-r). According to yet another embodiment the one or plurality of the carboxylic acid groups in the ion carrier chelate is replaced by neutral chelating groups, such as —CONH$_2$, CONHR$_1$ or —CONR$_1$R$_2$, where R$_1$ and R$_2$ are same or different chemical structures, as described in WO 2007/082996.

The preferred ion carrier ligand structures are hexadentate, heptadentate, or octadentate ligands capable to form thermodynamically and kinetically stable or preferably very stable complexes with lanthanide(III) ions as described also e.g. in U.S. Pat. No. 5,428,154, Carrera, C. et al. (2007) *Dalton Trans.* 4980-4987, Morcos, S. K. (2007) *The British Journal of Radiology* 80: 73-76; U.S. Pat. No. 5,622,688 and EP 0 416 033. Preferably, the chelating atoms in the ion carrier ligand are oxygen and nitrogen and according to one embodiment of the invention the chelating ligand contains a plurality of carboxylic acid groups. Derivatization methods for chelating ligands such as DOTA, EDTA and DTPA to conjugate linker and reactive group are described by Brücher, E. (2002) Topics in Current Chemistry 221: 103-122; Mishra, A. et al. (2005) Proc Intl Soc Mag Reson Med 13: 2592; and in U.S. Pat. No. 6,190,923. For example, suitable macrocyclic lanthanide ion carrier ligands containing active group (or their respective non-activated forms) are commercially available from Macrocyclics, Inc. (Dallas, Tex.); structures include e.g. 3,6,9,15-Tetraazabicyclo[9.3.1]pentadeca-1(15),11,13-triene-4-S-(4-isothiocyanatobenzyl)-3,6,9-triacetic acid; 1-Oxa-4,7,10-tetraazacyclododecane-5-S-(4-isothiocyanto-benzyl)-4,7, 10-triacetic acid; [(R)-2-Amino-3-(4-isothiocyanatophenyl) propyl]-trans-(S,S)-cyclohexane-1,2-diamine-pentaacetic acid; and 1,4,7,10-Tetraazacyclo-dodecane-1,4,7,10-tetraacetic acid mono-N-hydroxysuccinimide ester. When a complexing agent is employed, the lanthanide ion carrier chelate can be selected to have conditional formation constant at least the same or greater than EDTA complex at conditions prevailing in the bioassay. In case no complexing agent is preferred to be used, the ion carrier chelate can be selected to have conditional formation constant at least the same or greater than DTPA complex at conditions prevailing in the bioassay. When no complexing agent is employed, the ion carrier chelate is preferably selected to have slower dissociation than that of EDTA complex, more preferably slower than that of DTPA complex, at conditions prevailing in the bioassay.

Preferably, the ion carrier chelate is chosen from the schematic structures illustrated in FIG. 7/i-iii and the lanthanide (III) ion ($Ln^{3+}$) can be any of the trivalent lanthanide ions, but $Sm^{3+}$, $Eu^{3+}$, $Tb^{3+}$ and $Dy^{3+}$ are preferred for long-lifetime fluorescence-based assays utilizing time-resolved fluorometry and $Er^{3+}$ and $Tm^{3+}$ for upconversion fluorescence based assays. Preferably the ion carrier chelate is chosen not to contain any light-harvesting structure, in case of time-resolved fluorometry, which would be coordinated to the lanthanide ion and absorb at a wavelength range over 300 nm, preferably even over 280 nm.

Preferably both the ion carrier chelate and the light-harvesting antenna ligand are soluble in water, and the bioconjugates of them are soluble in water.

According to one embodiment of the current invention, the solubility of the light harvesting ligand is improved by adding solubility enhancing substituents to the structure, by adding a carboxylic acid (—COOH, —$CH_2$COOH), sulphonic acid, phosphonic acid or sugar residue (e.g. α-galactopyranoxy) as described in EP 1 447 666 and WO 2008/020113. Preferably, the chelating atoms in the antenna ligand are oxygen and nitrogen and according to one embodiment of the invention the antenna ligand contains one or two carboxylic acid groups.

Preferably, the optimal combination of the lanthanide(III) ion carrier chelate and the antenna ligand, which together are able to form the fluorescent lanthanide complex, is selected so that the sum total of ligand coordination sites (dentate count) is either nine or ten.

Preferably, for $Eu^{3+}$ and $Sm^{3+}$ the antenna ligand is chosen from schematic structures illustrated in FIG. 5/i-ii, a)-j), and for $Tb^{3+}$ and $Dy^{3+}$ from FIG. 5/i-ii, e)-j).

Complementing lanthanide-based fluorescent reporter technology is applicable to quantitative measurement of nucleic acids and proteins. Since a signal is only obtained when two probes, the other labelled with lanthanide ion carrier chelate and the other with light absorbing antenna, are bound precisely in adjacent position to the target molecule and only when the label components are in very tight contact, the generation of the signal is highly specific. The long emission lifetime of the lanthanide complex enables time-resolved measurement, which eliminates autofluorescence and unspecific binding derived background. This approach can also be used to monitor several analytes simultaneously (multianalyte approach) by using other lanthanide ion chelates and suitable light-harvesting ligands since lanthanide chelates have such unique spectral and temporal characteristics.

The method according to the present invention is suitable to monitoring both isothermal [Van Ness, J., et al. (2003) Proc Natl Acad Sci USA 100: 4504-4509] and thermocycled [Saiki et al. (1988) Science 239: 487-491] nucleic acid amplification reactions. For monitoring of polymerase chain reaction it is preferable to utilize a thermodynamically and kinetically very stable ion carrier chelate.

Polymerase chain reaction (PCR) is a method for increasing a copy number of specific sequence of double stranded DNA (amplicon) specified by short oligonucleotides (primers) complementary to different strands of target DNA. PCR is based on sequential, exponential increase of amplicon copy number by DNA polymerase activity. The cycling reaction includes typically three major steps, which are typically repeated for from 30 to 45 cycles. This is done on an automated cycler, which can heat and cool the reaction mixture in a very short time. The common reaction steps are:

1. Denaturation at high temperature, typically 90° C. or higher such as 94° C. yet below 100° C. During the denaturation, the double stranded DNA melts and opens to single stranded DNA, and all enzymatic reactions stop (e.g. the extension from a previous cycle).

2. Annealing at warm temperature, typically higher than 50° C., but lower than 75° C., e.g. 54° C. During the annealing, the primers associate with complementary single stranded target DNA or amplicon sequences.

3. Extension at medium high temperature, typically higher than 60° C., but lower than 75° C., e.g. 72° C. The bases (complementary to the template) are coupled to the primer on the 3' side (the polymerase adds dNTP's from 5' to 3', reading the template from 3' to 5' side, bases are added complementary to the template).

Steps 2 and 3 can be combined to a single step with conditions resembling step 2, but combining functions of both steps.

Typically each step takes a time varying from a few seconds to a few minutes, commonly the times being from tens of seconds to one or two minutes. Thus, the length of a PCR run and exposure of the reaction contents to warm and high temperatures varies from several minutes to a few hours. Typically the length of PCR is between 15 minutes and 1 h 30 minutes.

In real-time quantitative PCR or homogeneous end-point PCR the increase in copy number or the presence of amplicon can be detected using the method of the present invention.

When the method of the present invention is employed within PCR the conditions prevailing, i.e. temperature varying from 50° C. to 98° C. or more commonly from 60° C. to 98° C., impose significant requirements on the conditional stability of the ion carrier chelate. Dissociation of the lanthanide ion from the ion carrier chelate must be negligible in these conditions during the entire PCR, i.e. at least several minutes, typically more than 15 minutes and up to 2 hours.

The embodiments of the present invention provide a stability that allow both real-time and end-point detection of the amplified PCR product using the method of the present invention. The conditional stability constants of metal chelates of ligands are dependent on the prevailing conditions, including temperature. It is known that typically the conditional stability constants of metal chelates decrease with increasing temperature. This is due to increased dissociation at higher temperature. Thus only such ion carrier chelates are suitable for PCR that possess a high enough conditional formation constant also at conditions prevailing, i.e. at high temperature, and that are kinetically inert, i.e. that have slow dissociation at high temperature. The high enough conditional constant of the ion carrier chelate results in that the ion is not dissociated from the carrier chelate during PCR.

The complemented mixed lanthanide chelate formed by proximity probe-based recognition can be further utilized as donor in resonance energy transfer with luminescent (acceptor) or non-luminescent (quencher) fluorescent compound. The acceptor can be also selected not to have spectral overlapping with donor emission.

EXAMPLES

Example 1

Homogeneous Proximity Probe-Based Hybridization Assay

Synthetic target DNA oligonucleotide (5'-GATGCAG-TAGCAGGAAGAGGATCG-TAGCAATG-3'; SEQ ID NO: 1), amino-modified probe A oligonucleotide (5'-CAT-TGC-TACGATCC(C6dT)C-3'; SEQ ID NO: 2) and amino-modified probe B oligonucleotide (5'-T(C2dT)CCTGCTACTG-CATC-3'; SEQ ID NO: 3) were purchased from Sigma-Aldrich (St. Louis, Mo.). Probe A was labelled with $Eu^{3+}$ ion carrier chelate, ($N^1$-(4-isothiocyanatobenzyl)diethylenetriamine-$N^1,N^2,N^3,N^3$-tetrakis(acetato)europium(III) [Mukkala, V.-M. et al. (1989) Anal. Biochem., 176: 319], $Eu^{3+}$—N1) at the primary amino group modification located near the 3'-end and probe B was labelled with light harvesting antenna ligand (4-((isothio-cyanatophenyl)ethynyl)pyridine-2,6-dicarboxylic acid, 3d-antenna) near the 5'-end. Probe A, 25 nmol, was incubated with 20-fold molar excess of $Eu^{3+}$—N1 in 50 mM carbonate buffer, pH 9.8, at +37° C. over night. The total volume of the labelling reactions was 50 µL. For labelling of probe B with 3d-antenna, the 3d-antenna was dissolved in N,N-dimethylformamide (Sigma-Aldrich) and combined with oligonucleotide dissolved in water, and thereafter carbonate buffer, pH 9.8, was added to a concentration of 50 mM. In the labelling reaction, the molar excess of the 3d-antenna was 50-fold in a total volume of 110 µL. The reaction was incubated at +50° C. with slow rotation over night.

The purification of labelled probes was carried out with HPLC (instrumentation from Thermo Electron Corp., Waltham, Mass., USA) using an ODS C18 Hypersil column from Thermo Scientific (Waltham, Mass., USA) for purification of 3d-antenna-labeled probe B, and Luna C18 (2) column from Phenomenex (Torrance, Calif., USA) for purification of $Eu^{3+}$-N1-labeled probe A. Both columns were 150 mm long and i.d. of 4.6 mm. Purifications were performed using a gradient from 86% A and 14% B to 70% A and 30% B in 21 min with a flow rate of 0.5 mL min$^{-1}$ (A, aqueous 50 mM triethylammonium acetate (TEAA; Fluka Biochemica, Buchs, Switzerland); B, 50 mM TEAA in acetonitrile (J. T. Baker, Phillipsburg, N.J., USA)). The liquid from the collected fractions was evaporated in vacuum (Hetovac VR-1, Heto-Holten A/S, Allerod, Denmark) and then dissolved again in 10 mM Tris-HCl (pH 7.5), 50 mM NaCl. Labelled probes were characterized by measuring absorbance readings at 260 and 330 nm and the total $Eu^{3+}$ concentrations were measured with DELFIA technology (PerkinElmer Life and Analytical Sciences, Wallac, Turku, Finland).

The assay was performed by using Low Fluorescence 96-well Maxisorp microtitration plates purchased from Nunc (Roskilde, Denmark) in assay buffer containing 50 mM Tris-HCl (pH 7.75), 600 mM NaCl, 0.1% Tween 20, 0.05% $NaN_3$, and 30 µm diethylenetriaminepentaacetic acid (DTPA). The probe A-$Eu^{3+}$—N1 and probe B-3d-antenna (10 or 50 nM) and the target oligonucleotide (0-50 nM) were combined in a total volume of 60 µL and added to the wells. The plate was incubated first at slow shaking for a short period of time and then without shaking for 15 and 60 minutes at RT. Time-resolved fluorescence measurements were made with a 1420 Victor Multilabel Counter (Perkin-Elmer Life And Analytical Life Sciences, Turku, Finland) by using a 340 nm excitation filter, 615 nm emission filter, 400 µs delay and 400 µs measurement time, and counting 1000 measurement cycles.

The principle of the chelate complementation assay method is presented in FIG. 1. Two 16-mer probes, probe A labelled with a europium(III) ion carrier chelate ($N^1$-(4-isothiocyanatobenzyl)diethylenetriamine-$N^1,N^2,N^3,N^3$-tetrakis(acetato)europium(III) [Mukkala et al. (1989)] $Eu^{3+}$—N1, schematic structure in FIG. 8a), at an amino-modified thymine placed one nucleotide internal to the 3' end and probe B labelled with a light harvesting antenna (4-((isothiocyanatophenyl)-ethynyl)pyridine-2,6-dicarboxylic acid, 3d-antenna, schematic structure in FIG. 8b), at an amino-modified thymine placed one nucleotide internal to the 5' end, were complementary to a 32-mer target oligonucleotide. Since the affinity of probe A-$Eu^{3+}$—N1 and probe B-3d-antenna towards each other is minimal, no fluorescence can be detected in the absence of complementary target oligonucleotide. In the presence of the target oligonucleotide, the probe A-$Eu^{3+}$—N1 and probe B-3d-antenna hybridize to adjacent positions on the target oligonucleotide and $Eu^{3+}$—N1 and 3d-antenna form a mixed chelate complex which will fluorescence at a specific wavelength with a large Stoke's shift, sharp emission peak and long fluorescence lifetime.

Figure 9:
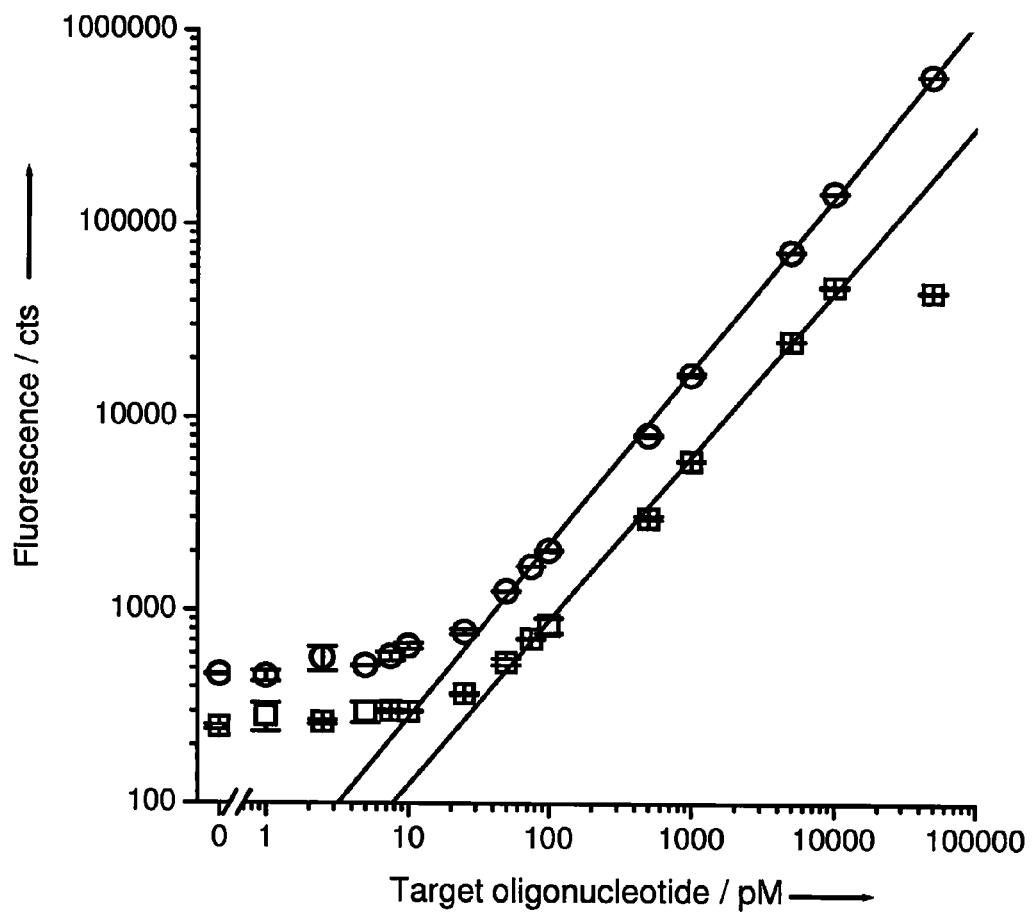
FIG. 9 presents results from homogeneous hybridization assay described in Example 1. Time-resolved fluorescence after hybridization of the labelled probe pair (10 nM: square; 50 nM: circle) with increasing concentration of the target oligonucleotide. Cts refers to counts. Error bars indicate standard deviation of the mean.

Results of the experiment are illustrated in FIG. 9, where the $Eu^{3+}$-specific fluorescence after hybridization of probe A-$Eu^{3+}$—N1 and probe B-3d-antenna with the target oligonucleotide is presented. The squares present the measured results from reactions with 10 nM concentrations of probe A-$Eu^{3+}$—N1 and probe B-3d-antenna and circles results from reactions with 50 nM concentrations of the same probes. The amount of probe A-$Eu^{3+}$—N1 and probe B-3d-antenna was constant while the amount of target oligonucleotide increased. The detection limit, defined as the concentration corresponding to three times standard deviation of background signal, is 13 pM (0.78 fmol per assay) when the amount of probe A-$Eu^{3+}$—N1 and probe B-3d-antenna was 50 nM. The detection limit in our assay was better than previously [A. Oser, G. Valet (1990) Angew. Chem. 102, 1197; Angew. (1990) Chem. Int. Ed. Engl. 29, 1167] reported, and especially the signal to background ratio over thousand (up to 1400:1) and the signal level in our assay were outstanding compared to prior art [Wang, G., Yuan, J., Matsumoto, K., and Hu, Z. (2001) Anal. Biochem. 299: 169], where ratios below three (lower than 3:1) have been presented. This was achieved by using appropriately selected ion carrier chelate, antenna ligand, linker sequences, oligonucleotide modifications, and especially adding the complexing agent to complex virtually any free europium(III) ion present in solution. The dynamic range in our assay covers four orders of magnitude and the fluorescence signal was stable for at least one hour.

The surprising effect of DTPA concentration is illustrated in Table 1. Optimal DTPA concentration in the example was 30 µM or higher. In absence of DTPA the signal-to-background with 10 nM probe concentration was less than two, whereas with 30 and 100 µM DTPA concentrations ratios over 70 were obtained. This illustrates the significant improvement obtained by the present invention over the prior art, where the background has been clearly observable. The results indicate that at the prevailing conditions the concentration of the free lanthanide ion is originally nanomolar in absence of the complexing agent, whereas with complexing agent added, the concentration of the free ion can be reduced by a factor at least one hundred, potentially over one thousand, to picomolar concentrations, or to concentrations less than one picomolar. This will result in dramatic decrease in the assay background and significant increase in the obtained signal to background ratio.

TABLE 1

Effect of DTPA concentration on the assay performance.

| | Fluorescence (counts) | | | | |
|---|---|---|---|---|---|
| DTPA/microM | 0 | 5 | 10 | 30 | 100 |
| no template (background) | 93317 | 8521 | 3139 | 839 | 649 |
| 10 nM template (signal) | 166234 | 58486 | 55254 | 60170 | 49414 |
| S/B ratio | 1.8 | 6.9 | 17.6 | 71.7 | 76.1 |

Example 2

Specificity in Signal Generation

Non-complementary target oligonucleotide (5'-CTGCTC-TATCCACGGCG-CCCGCGGCTCCTCTC-3'; SEQ ID NO: 4) was purchased from Biomers.net (Ulm, Germany). The experiment described in Example 1 was repeated by replacing the target oligonucleotide with the non-complementary target oligonucleotide. Replacement of the complementary target oligonucleotide with variable concentrations of a noncomplementary 32-mer oligonucleotide resulted in the same fluorescence signal as in the absence of complementary target oligonucleotide; no detectable signal differences were observed in presence of variable concentrations non-complementary target oligonucleotides compared to zero concentration of target oligonucleotides; i.e. blank control. This indicates that the signal generation mechanism in the present invention is highly specific and dependent on the two simultaneous biomolecular recognition events.

Example 3

Emission Spectrum and Fluorescence Lifetime

Additional probe, amino-modified probe C oligonucleotide (5'-CATTGCTACGAT-CC(C2dT)C-3'; SEQ ID NO: 5) was purchased from Sigma-Aldrich (St. Louis, Mich.) and labelled with intrinsically fluorescent 2,2',2'',2'''[[4-[(4-isothiocyanatophenyl)-ethynyl] pyridine-2,6-diyl]bis(methylenenitrilo)]tetrakis(acetato)europium(III) ($Eu^{3+}$-7d; schematic structure in FIG. 8c). Probe C, 5 nmol, was incubated with 20-fold molar excess of $Eu^{3+}$-7d in 50 mM carbonate buffer, pH 9.8, at +37° C. over night and purified as described for A-$Eu^{3+}$—N1 in Example 1.

Figure 10:
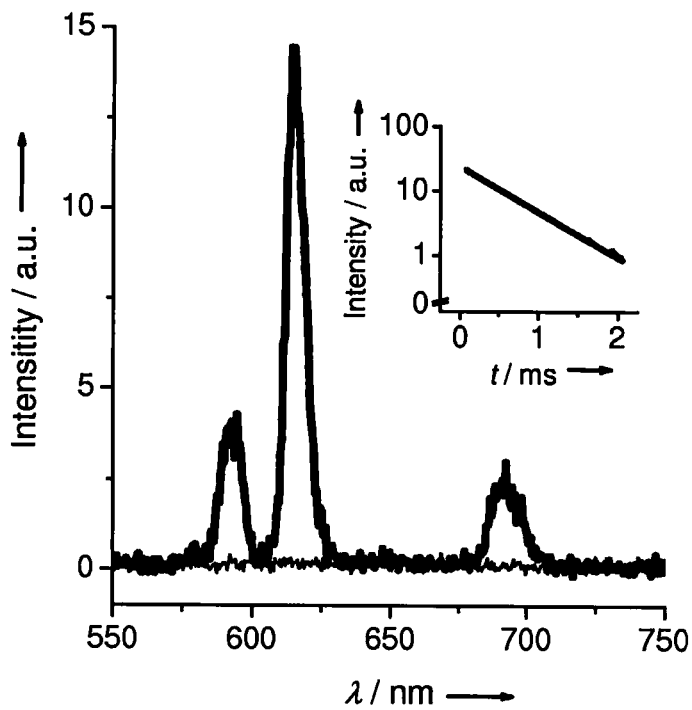
FIG. 10 illustrates the fluorescence emission spectrum of a) oligonucleotide directed complex formed of probe A-$Eu^{3+}$—N1 and probe B-3d-antenna with 0 nM (dashed line) and 10 nM (thick solid line) target oligonucleotide and b) probe C-$Eu^{3+}$-7d obtained in Example 2. The fitted emission decay spectrum of the complex formed of probe A-$Eu^{3+}$—N1 and probe B-3d-antenna with 10 nM target oligonucleotide and decay spectrum of the probe C—$Eu^{3+}$-7d are presented in figure inserts. A.u. refers to arbitrary unit.
Figure 10:
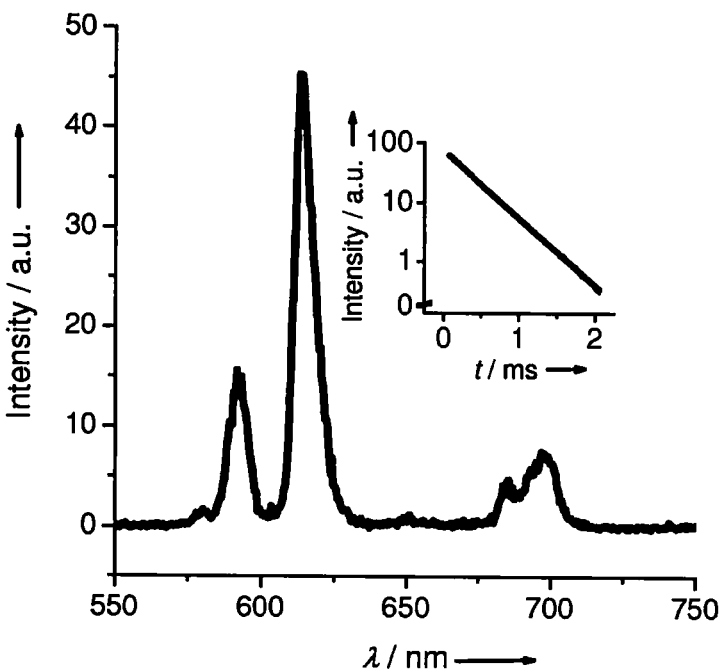

Fluorescence spectrum and emission lifetime of an intrinsically fluorescent $Eu^{3+}$-chelate labelled probe C—$Eu^{3+}$-7d, and separately the target oligonucleotide directed complex of the probe A-$Eu^{3+}$—N1 and probe B-3d-antenna were measured with a Varian Cary Eclipse fluorescence spectrophotometer (Varian Scientific Instruments, Mulgrave, Australia). The target oligonucleotide (0 or 10 nM) was mixed with probe A-$Eu^{3+}$—N1 and probe B-3d-antenna (50 nM) in assay buffer and incubated for 30 minutes at RT before the measurement. The fluorescence spectra with 0 nM (narrow line) and 10 nM (thick line) of target oligonucleotide are illustrated in FIG. 10a. To compare the fluorescence properties of the complex to the fluorescence properties of intrinsically fluorescent $Eu^{3+}$-chelate, the probe C—$Eu^{3+}$-7d was diluted to a concentration of 50 nM in assay buffer and the spectra were measured. The fluorescence spectrum of the probe C—$Eu^{3+}$-7d is shown in FIG. 10b. The complex that formed in the presence of target oligonucleotide from probe A-$Eu^{3+}$—N1 and probe B-3d-antenna generated fluorescence spectrum similar to the intrinsically fluorescent probe C—$Eu^{3+}$-7d with the main emission peak at 615 nm. In the absence of the target oligonucleotide, no long-lifetime fluorescence emission with probe A-$Eu^{3+}$—N1 and probe B-3d-antenna was detected resulting in a flat line in the spectrum. The fluorescence decay time of the complex formed of probe A-$Eu^{3+}$—N1 and probe B-3d-antenna in the presence of 10 nM target oligonucleotide was 618 μs (decay spectrum inset in FIG. 10a) and the fluorescence decay time of the probe C—$Eu^{3+}$-7d was 380 μs (inset in FIG. 10b). This indicates that the mixed chelate complex is better protected from the water molecules than the ion in the intrinsically fluorescent 7 dentate chelate in the probe C—$Eu^{3+}$-7d.

Example 4

Heterogeneous Proximity Probe-Based Hybridization Assay

Amino-modified probe oligonucleotides (probe A, 5'-CATTGCTACGATCC-(C6dT)C-3', SEQ ID NO: 2 and probe B, 5'-T(C2dT)CCTGCTACTGCATC-3', SEQ ID NO: 3) were purchased from Sigma-Aldrich (St. Louis, Mich.). Probe A was labelled with $N^1$-(4-isothiocyanatobenzyl)diethylenetriamine-$N^1,N^2,N^3,N^3$-tetrakis-(acetato)europium(III) [V.-M. Mukkala et al. (1989) *Anal. Biochem.* 176, 319] ($Eu^{3+}$—N1; schematic structure in FIG. 8a) and with an intrinsically fluorescent 2,2',2'',2'''-[[4-[(4-isothiocyanatophenyl)ethynyl]pyridine-2,6-diyl]bis(methylene-nitrilo)]tetrakis(acetato)europium(III) [H. Takalo et al. (1994) *Bioconjugate Chem,* 5, 278] ($Eu^{3+}$-7d; schematic structure in FIG. 8c), and probe B was labeled with 4-((isothiocyanatephenyl)ethynyl)pyridine-2,6-dicarboxylic acid (antenna; schematic structure in FIG. 8b). Probe A, 25 nmol and 5 nmol, were incubated with 20-fold molar excess of $Eu^{3+}$—N1 and $Eu^{3+}$-7d, respectively, in 50 mM carbonate buffer, pH 9.8, at +37° C. over night. The total volume of the labelling reactions was 50 μl. For labelling of probe B with antenna, the antenna was dissolved in N,N-dimethylformamide (Sigma-Aldrich) and combined with oligonucleotide dissolved in water, and thereafter carbonate buffer, pH 9.8, was added to a concentration of 50 mM. In the labelling reaction, the molar excess of the antenna was 50-fold in a total volume of 110 μl. The reaction was incubated at +50° C. with slow rotation over night.

The purification of labelled probes was carried out with HPLC (instrumentation from Thermo Electron Corp., Waltham, Mass., USA) using an ODS C18 Hypersil column from Thermo Scientific (Waltham, Mass., USA) for purification of antenna-labelled probe B, and Luna C18 (2) column from Phenomenex (Torrance, Calif., USA) for purification of $Eu^{3+}$—N1 and $Eu^{3+}$-7d-labelled probe A. Purifications were performed using a gradient from 86% A and 14% B to 70% A and 30% B in 21 min with a flow rate of 0.5 mLmin$^{-1}$ [A, aqueous 50 mM triethylammonium acetate (TEAA; Fluka Biochemica, Buchs, Switzerland); B, 50 mM TEAA in acetonitrile (J. T. Baker, Phillipsburg, N.J., USA)]. The liquid from the collected fractions was evaporated in vacuum (Hetovac VR-1, Heto-Holten A/S, Allerod, Denmark) and then dissolved again in 10 mM Tris-HCl (pH 7.5), 50 mM NaCl. Labelled probes were characterized by measuring absorbance readings at 260 and 330 nm and the total $Eu^{3+}$ concentrations were measured with DELFIA system (PerkinElmer Life and Analytical Sciences, Wallac, Turku, Finland).

Biotinylated target oligonucleotide (5'-biotin-TTGATG-CAGTAGCAGGAAGAGG-ATCGTAGCAATG-3'; SEQ ID NO: 6) was purchased from Biomers.net GmbH (Ulm, Germany). The assays were performed in C8 White Maxisorp plates (Nunc, Roskilde, Denmark) that were spot-coated [L. Välimaa et al. (2008) *Anal. Bioanal. Chem.* 391, 2135] with N-succinimidyl S-acetylthioacetate (SATA, Pierce Biotechnology, Rockford, Ill.)-activated [J. Ylikotila et al. (2008) *Colloids and Surfaces B: Biointerfaces*, doi: 10.1016/j.colsurfb.2008.12.042] streptavidin (BioSpa, Milan, Italy). All dilutions were made in assay buffer containing 50 mM Tris-HCl (pH 7.75), 600 mM NaCl, 0.1% (v/v) Tween20, 0.05% (w/v) NaN$_3$, 1 µM diethylenetriaminepentaacetic acid. The wells were prewashed once with DELFIA Wash Solution (PerkinElmer Life and Analytical Sciences, Wallac) supplemented with NaCl to the final concentration of 600 mM. Biotinylated target oligonucleotide, 0-200 nM in 30 µl, was added and the plate was incubated for 30 min at RT in slow shaking before adding probe A-Eu$^{3+}$—N1 and probe B-antenna or probe A-Eu$^{3+}$-7d, 200 nM in 30 µl. After 30 min of shaking, the plate was washed three times like previously and left to dry at RT before time-resolved fluorescence measurement with a 1420 Victor Multilabel Counter (Perkin-Elmer Life and Analytical Sciences, Turku, Finland) by using a 340 nm excitation filter, 615 nm emission filter, 400 µs delay and 400 µs measurement time.

Figure 11:
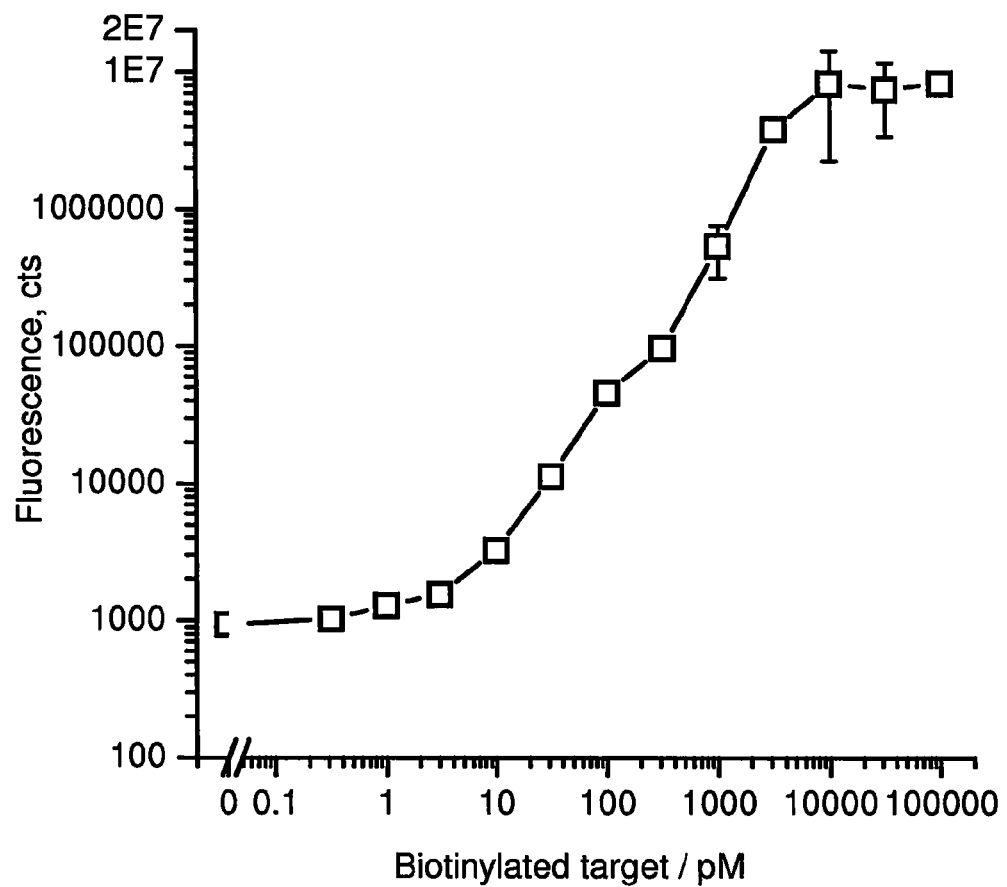
FIG. 11 presents results of heterogeneous proximity probe-based hybridization assay described in Example 4. Time-resolved fluorescence after incubation of a) probe A-$Eu^{3+}$—N1 and probe B-antenna with increasing concentration of biotinylated target oligonucleotide and b) probe A-$Eu^{3+}$-7d with increasing concentration of biotinylated target oligonucleotide. Cts refers to counts.
Figure 11:
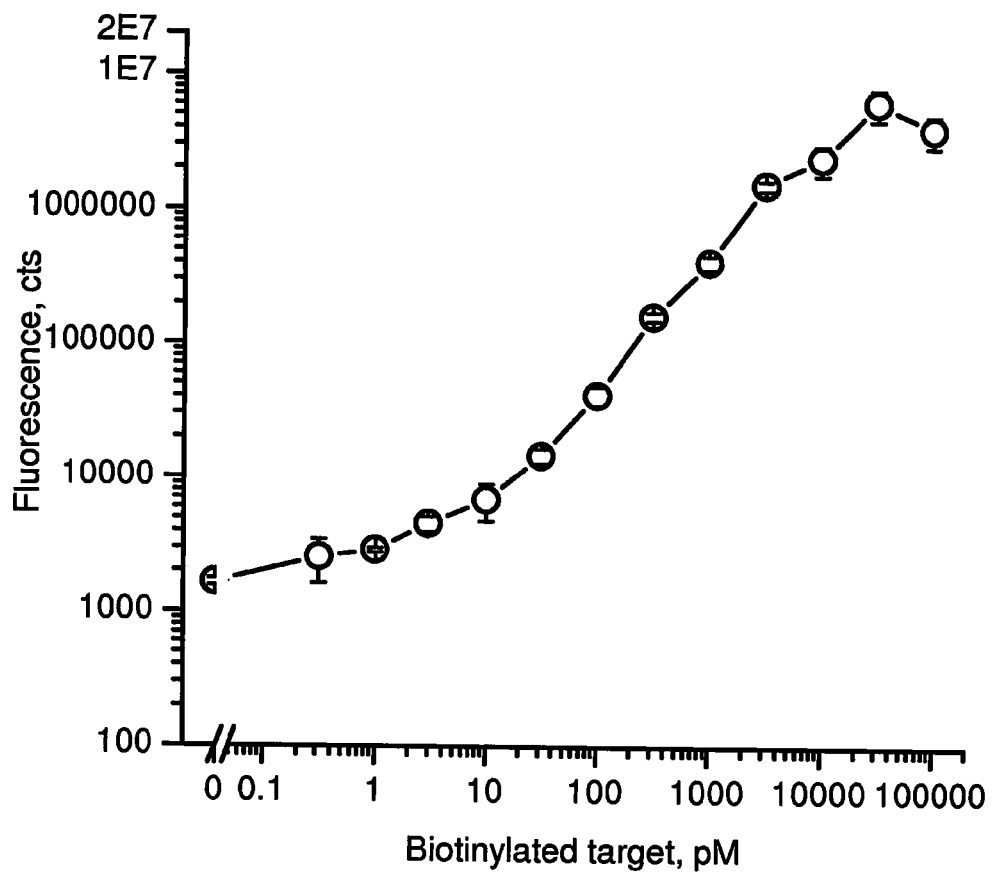

The results obtained with increasing concentration of biotinylated target oligonucleotide using probe A-Eu$^{3+}$—N1 and probe B-antenna is illustrated in FIG. 11a and results using probe A-Eu$^{3+}$-7d are shown in FIG. 11b. The proximity probe-based assay with complementing chelate approach as described in the present invention enabled lower fluorescence background with same fluorescence signal and resulted in improved limit of detection. This indicates that the present invention is applicable to heterogeneous assays, improving the assay performance. The signal generation is restricted only to mixed chelate complexes, which require two adjacent biomolecular recognition events for their formation.

Example 5

Homogeneous Proximity Probe-Based Assay for Streptavidin and Avidin

Figure 12:
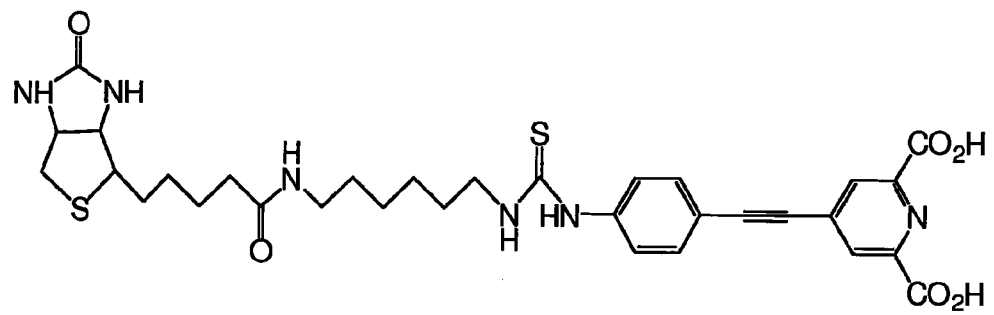
FIG. 12 illustrates biotin conjugates employed in the proximity probe-based assay for streptavidin and avidin in Example 5. a) (+)-biotinyl-hexanediamine-3d-antenna and b) (+)-biotinyl-3,6-dioxaoctanediamine-$Eu^{3+}$—N1.
Figure 12:
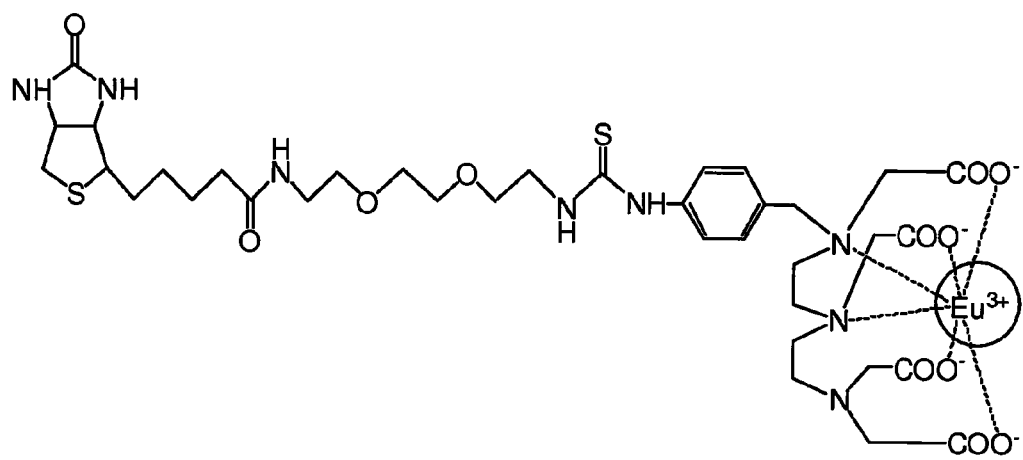

N-(6-aminohexyl)-5-(2-oxohexahydro-1H-thieno[3,4-d]imidazol-4-yl)pentanamide ((+)-biotinyl-hexanediamine) was coupled to 4-((isothiocyanatephenyl)ethynyl)-pyridine-2,6-dicarboxylic acid (antenna). The schematic structure of the product of coupling reaction is illustrated in FIG. 12a. For coupling, (+)-biotinyl-hexanediamine and antenna were dissolved in N,N-dimethylformamide (Sigma-Aldrich, St. Louis, Mo.) and combined, and thereafter carbonate buffer, pH 9.8, was added to a concentration of 50 mM. In the coupling reaction, the molar excess of the (+)-biotinyl-hexanediamine was 3-fold in a total volume of 270 µl. The reaction was incubated at +50° C. with slow rotation over night.

The purification of the coupling reaction was carried out with HPLC (instrumentation from Thermo Electron Corp., Waltham, Mass., USA) using an ODS C18 Hypersil column from Thermo Scientific (Waltham, Mass., USA) and an HPLC Column Oven 2155 (Pharmacia LKB, Uppsala, Sweden). Purification was performed using a gradient from 80% A and 20% B to 0% A and 100% B in 30 min with a flow rate of 0.5 mL min$^{-1}$ [A, aqueous 50 mM triethylammonium acetate (TEAA; Fluka Biochemica, Buchs, Switzerland); B, 50 mM TEAA in acetonitrile (J. T. Baker, Phillipsburg, N.J., USA)] at +50° C. The liquid from the collected fractions was evaporated in vacuum (Hetovac VR-1, Heto-Holten A/S, Allerod, Denmark) and then dissolved again in 10 mM Tris-HCl (pH 7.5), 50 mM NaCl, 0.05% w/v NaN$_3$. Dissolved fractions were characterized by measuring absorbance reading at 330 nm.

N-(2-(2-(2-aminoethoxy)ethoxy)ethyl)-5-(2-oxohexahydro-1H-thieno[3,4-d]imidazol-4-yl)pentanamide (Pierce, Rockford, Ill., USA) ((+)-biotinyl-3,6-dioxaoctanediamine) was conjugated to N$^1$-(4-isothiocyanatobenzyl)diethylenetriamine-N$^1$,N$^2$,N$^3$,N$^3$-tetrakis(acetato)europium(III) [Mukkala V.-M., et al. (1989) *Anal. Biochem.* 176, 319] (Eu$^{3+}$—N1) purchased from Perkin Elmer Life and Analytical Sciences (Wallac Oy, Turku, Finland). The schematic structure of the product of coupling reaction is illustrated in FIG. 12b. The conjugation reaction and purification by HPLC was carried out like previously described [Kuningas, T. et al. (2005) *Anal. Chem.* 77, 2826].

Assays were performed in C8 white Maxisorp microtitration plates purchased from Nunc (Roskilde, Denmark) in assay buffer containing 50 mM Tris-HCl (pH 7.5), 50 mM NaCl, 10 µM diethylenetriaminepentaacetic acid. The wells were blocked with bovine serum albumin beforehand to prevent non-specific binding of streptavidin or avidin on the well surfaces. Streptavidin from BioSpa (Milan, Italy) or avidin from Sigma (0-100 nM) and (+)-biotinyl-hexanediamine-antenna (schematic structure of the conjugate in FIG. 12a) and (+)-biotinyl-3,6-dioxaoctanediamine-Eu$^{3+}$—N1 (schematic structure of the conjugate in FIG. 12b) (20 nM) were combined in a total volume of 60 µl and added to the wells. The plate was incubated first at slow shaking for a short period of time and then without shaking for 15 and 60 minutes at RT. Time-resolved fluorescence measurements were made with a 1420 Victor Multilabel Counter (Perkin-Elmer Life And Analytical Life Sciences, Turku, Finland) by using a 340 nm excitation filter, 615 nm emission filter, 400 µs delay and 400 µs measurement time.

Figure 13:
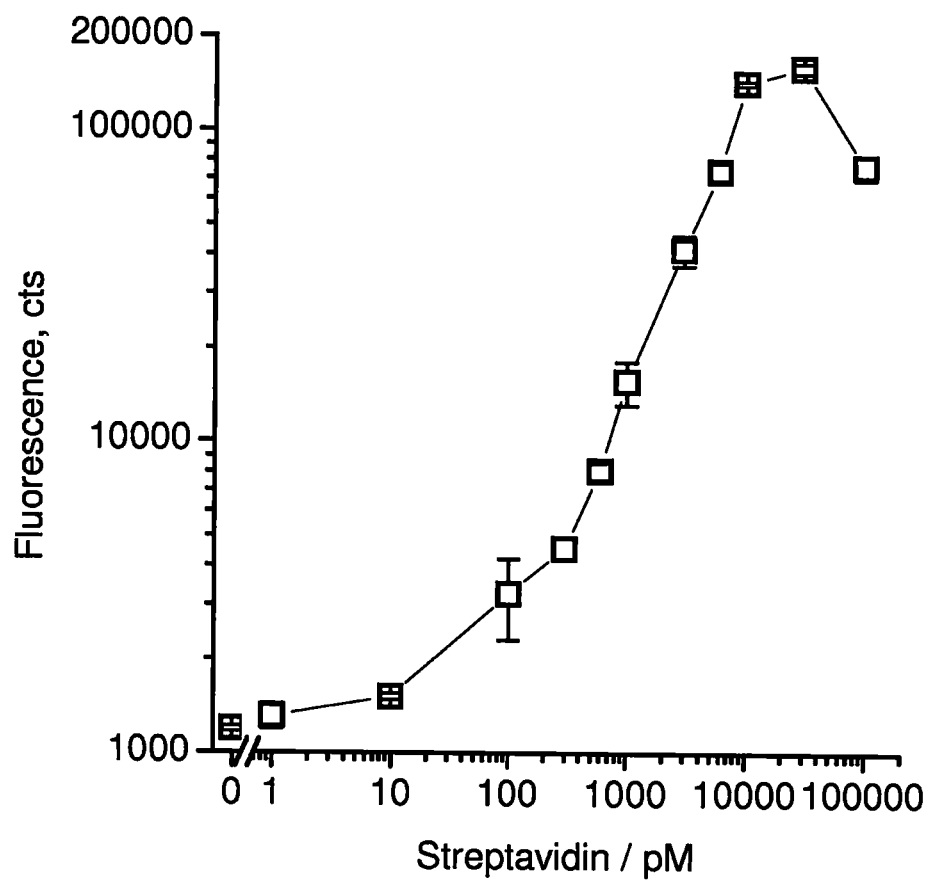
FIG. 13 presents results of streptavidin and avidin assay described in Example 5. Time-resolved fluorescence after incubation of (+)-biotinyl-hexane-diamine-antenna and (+)-biotinyl-3,6-dioxaoctanediamine-$Eu^{3+}$—N1 with increasing concentration of a) streptavidin or b) avidin. Cts refers to counts.
Figure 13:
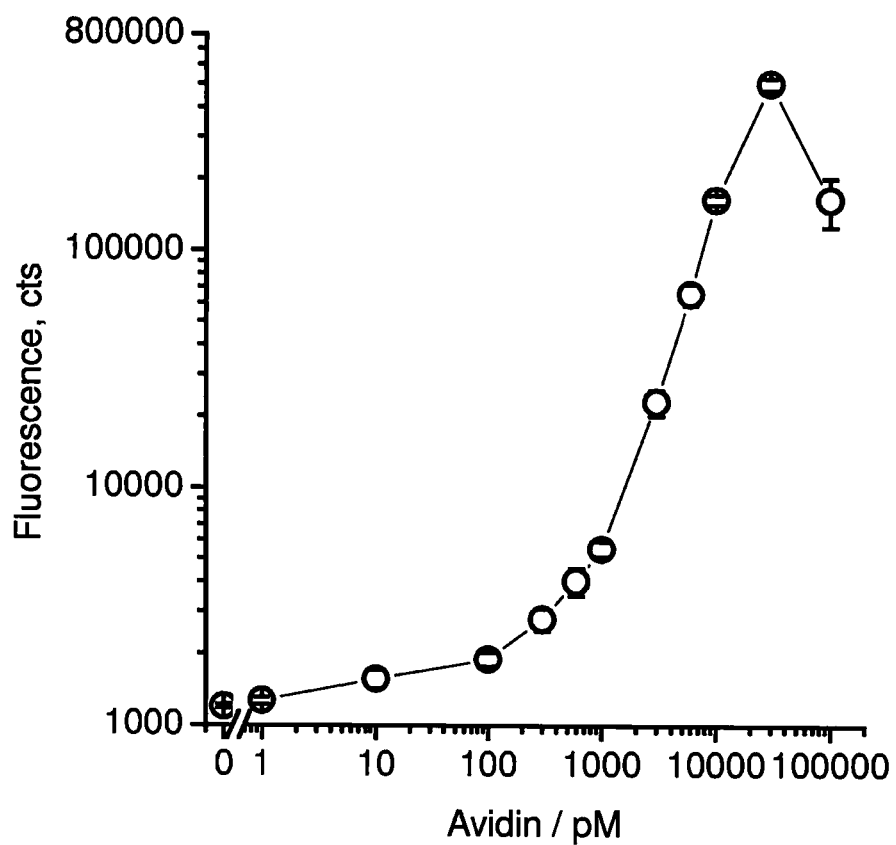

The results obtained with increasing concentration of streptavidin are shown in FIG. 13a and results with avidin in FIG. 13b. The results indicate that the present invention is also applicable to detection of multimeric proteins (streptavidin and avidin are tetrameric proteins). The label moieties, i.e. the lanthanide ion carrier chelate and the antenna ligand are coupled to such biomolecular recognition elements, that have separate binding sites on the protein molecule at suitable distance. In the example the biotin binding sites were identical and there was one of those in each monomer of streptavidin.

Example 6

Homogeneous Hybridization Assay Using Terbium(III) Ion

Synthetic target DNA oligonucleotide (5'-GATGCAG-TAGCAGGAAGAGGATCG-TAGCAATG-3'; SEQ ID NO: 1) and amino-modified probe A oligonucleotide (5'-CAT-TGCTACGATCC(C2dT)C-3'; SEQ ID NO:2) were purchased from Sigma-Aldrich (St. Louis, Mich., USA) and amino-modified probe B oligonucleotide (5'-T(C2dT)CCT-GCTACTGCATC-3'; SEQ ID NO: 3) was purchased from Thermo Scientific (Waltham, Mass., USA). Probe A was labelled with Tb$^{3+}$ ion carrier chelate, (N$^1$-(4-isothiocyanatobenzyl)diethylenetriamine-N$^1$,N$^2$,N$^3$,N$^3$-tetrakis(acetato)-terbium(III), Tb$^{3+}$—N1) at the primary amino group modification located near the 3' end and probe B was labelled with light harvesting antenna ligand (4-(3-(4-iso-thiocyanatophenetyl)-2,4,6-trimethoxyphenyl)pyridine-2,6-dicarboxylic acid, TMP-antenna) near the 5' end. Probe A, 10 nmol, was incubated with 20-fold molar excess of Tb$^{3+}$—N1 in 50 mM carbonate buffer, pH 9.8, at +37° C. over night. The total volume of the labelling reactions was 50 µL. For labelling of probe B with TMP-antenna, the TMP-antenna was dissolved in 75% N,N-dimethylformamide (Sigma-Aldrich), combined with oligonucleotide, and thereafter carbonate buffer, pH 9.8, was added to a concentration of 50 mM. In the labelling reaction, the molar excess of the TMP-antenna was 50-fold in a total volume of 70 µL. The reaction was incubated at +50° C. with slow rotation over night.

The purification of labelled probes from conjugation reactions was carried out first with gel filtration using NAP-5 Sephadex colums (GE Healthgare, Buckinghamshire, United Kingdom) and thereafter with HPLC (instrumentation from Thermo Electron Corp., Waltham, Mass., USA) using an ODS C18 Hypersil column from Thermo Scientific for purification of TMP-antenna-labeled probe B and Luna C18 (2) column from Phenomenex (Torrance, Calif., USA) for purification of $Tb^{3+}$-N1-labeled probe A. The eluate from the gel filtration was evaporated in vacuum (Hetovac VR-1, Heto-Holten A/S, Allerod, Denmark), dissolved in 10 mM Tris-HCl (pH 7.5), 50 mM NaCl and used for the HPLC purification. HPLC purifications were performed using a gradient from 86% A and 14% B to 70% A and 30% B in 21 min with a flow rate of 0.5 mL $min^{-1}$ (A, aqueous 50 mM triethylammonium acetate (TEAA; Fluka Biochemica, Buchs, Switzerland); B, 50 mM TEAA in acetonitrile (J. T. Baker, Phillipsburg, N.J., USA)). The liquid from the collected fractions was evaporated in vacuum and then dissolved again in 10 mM Tris-HCl (pH 7.5), 50 mM NaCl. Labelled probes were characterized by measuring absorbance readings at 260 and 330 nm and the total $Tb^{3+}$ concentrations were measured with DELFIA technology (PerkinElmer Life and Analytical Sciences, Wallac, Turku, Finland). The purification of the coupling reactions included two different methods to improve the purification efficiency.

The assay was performed by using Low Fluorescence 96-well Maxisorp microtitration plates purchased from Nunc (Roskilde, Denmark) in assay buffer containing 50 mM Tris-HCl (pH 7.75), 600 mM NaCl, 0.1% Tween 20, 0.05% $NaN_3$, and 30 µm diethylenetriaminepentaacetic acid (DTPA). The probe A-$Tb^{3+}$—N1 and probe B-TMP-antenna (10 or 50 nM) and the target oligonucleotide (0-50 nM) were combined in a total volume of 60 µL and added to the wells. The plate was incubated first at slow shaking for a short period of time and then without shaking for 45 minutes at RT. Time-resolved fluorescence measurements were made with a 1420 Victor Multilabel Counter (Perkin-Elmer Life And Analytical Life Sciences, Turku, Finland) by using a 340 nm excitation filter, 545 nm emission filter, 400 µs delay and 1200 µs measurement time, and counting 2000 measurement cycles.

Figure 14:
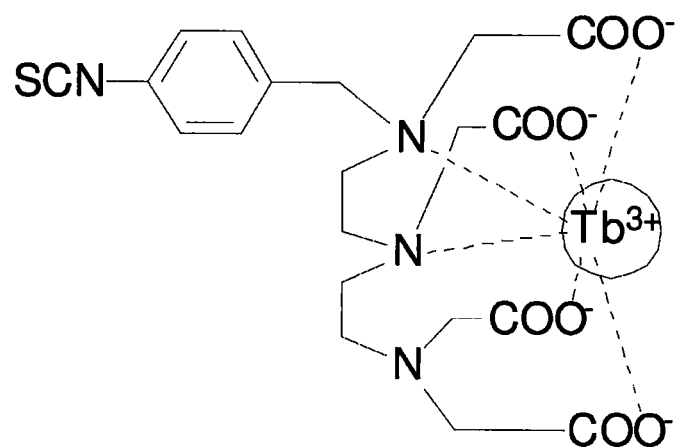
FIG. 14 shows schematic structures of a) terbium(III) carrier chelate $N^1$-(4-iso-thiocyanatobenzyl)diethylenetriamine-$N^1,N^2,N^3,N^3$-tetrakis(acetato)terbium(III) ($Tb^{3+}$—N1; carrier chelate) and b) light-harvesting antenna ligand 4-(3-(4-isothio-cyanatophenetyl)-2,4,6-trimethoxyphenyl)pyridine-2,6-dicarboxylic acid (TMP-antenna) employed in Example 6 and Example 7.
Figure 14:
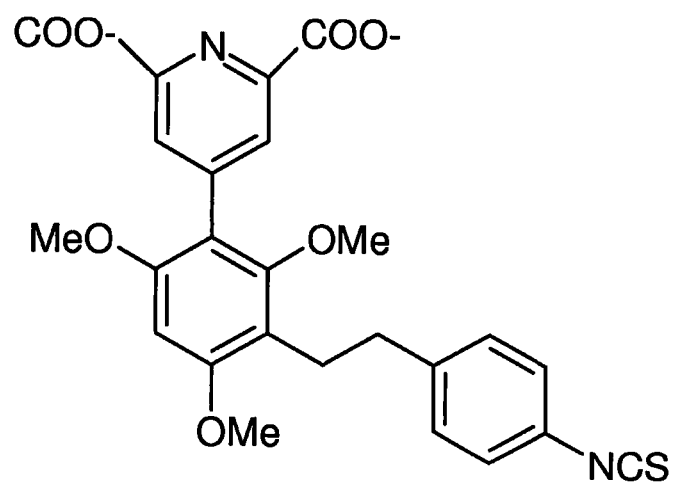

For the terbium chelate complementation assay two 16-mer probes complementary to a 32-mer target oligonucleotide were used: probe A labelled with a terbium ion carrier chelate ($N^1$-(4-isothiocyanatobenzyl)diethylenetriamine-$N^1$, $N^2$,$N^3$,$N^3$-tetrakis(acetato)terbium(III), $Tb^{3+}$—N1, FIG. 14a) at an amino-modified thymine placed one nucleotide internal to the 3' end and probe B labelled with a reactive light harvesting antenna (4-(3-(4-isothiocyanatophenetyl)-2,4,6-trimethoxyphenyl)pyridine-2,6-dicarboxylic acid), TMP-antenna, FIG. 14b) at an amino-modified thymine placed one nucleotide internal from the 5' end. Since the affinity of probe A-$Tb^{3+}$—N1 and probe B-TMP-antenna towards each other is minimal, no fluorescence can be detected in absence of complementary target oligonucleotide. In the presence of the target oligonucleotide, the probe A-$Tb^{3+}$—N1 and probe B-TMP-antenna hybridize to the target and $Tb^{3+}$—N1 and TMP-antenna form a complex which will fluorescence at a specific wavelength with a large Stoke's shift, sharp emission peaks and long fluorescence lifetime.

Figure 15:
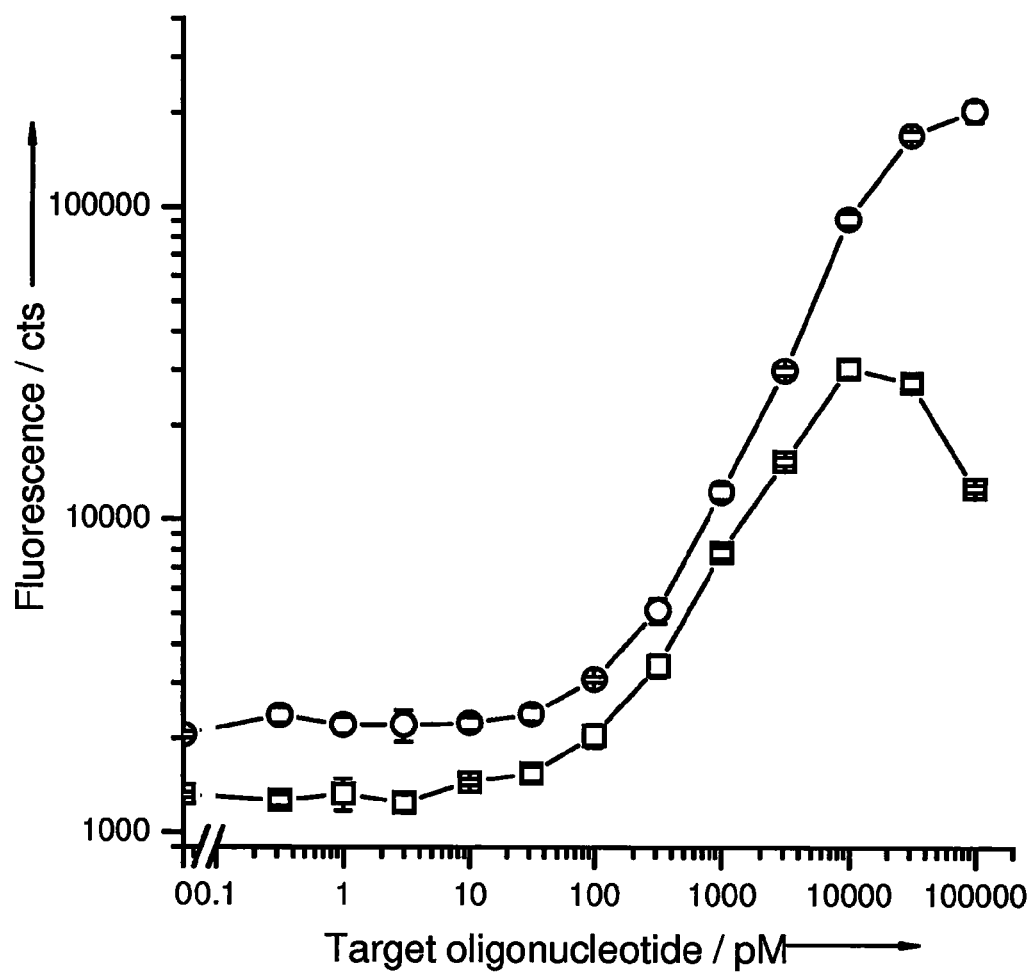
FIG. 15 presents results from the homogeneous hybridization assay described in Example 6. Time-resolved fluorescence after hybridization of the labelled probe pair (10 nM: square; 50 nM: circle) with increasing concentration of the target oligonucleotide. Cts refers to counts.

The $Tb^{3+}$-specific fluorescence after hybridization of probe A-$Tb^{3+}$—N1 and probe B-TMP-antenna with the target oligonucleotide is presented in FIG. 15. The amount of probe A-$Tb^{3+}$—N1 and probe B-TMP-antenna was constant (either 10 nM, results shown with squares, or 50 nM, results shown with circles) while the amount of target oligonucleotide was varied. The time-resolved emission at main emission peak at 545 nm was measured. The detection limit was less than 100 pmol/l concentration of target oligonucleotide and the dynamic range in our assay covered up to four orders of magnitude. DTPA was present at 30 µM concentration. The result indicates that the present invention is easily transferable to other luminescent lanthanide ions by selecting suitable light harvesting antenna ligand.

Example 7

Emission Spectrum and Fluorescence Lifetime with Terbium(III) Ion

Fluorescence spectrum and emission lifetime of the target oligonucleotide directed complex of the probe A-$Tb^{3+}$—N1 and probe B-TMP-antenna were measured with a Varian Cary Eclipse fluorescence spectrophotometer (Varian Scientific Instruments, Mulgrave, Australia). The target oligonucleotide (0 or 10 nM) was mixed with probe A-$Tb^{3+}$—N1 (50 nM) and probe B-TMP-antenna (50 nM) in assay buffer and incubated for 60 minutes at RT before the measurement.

Figure 16:
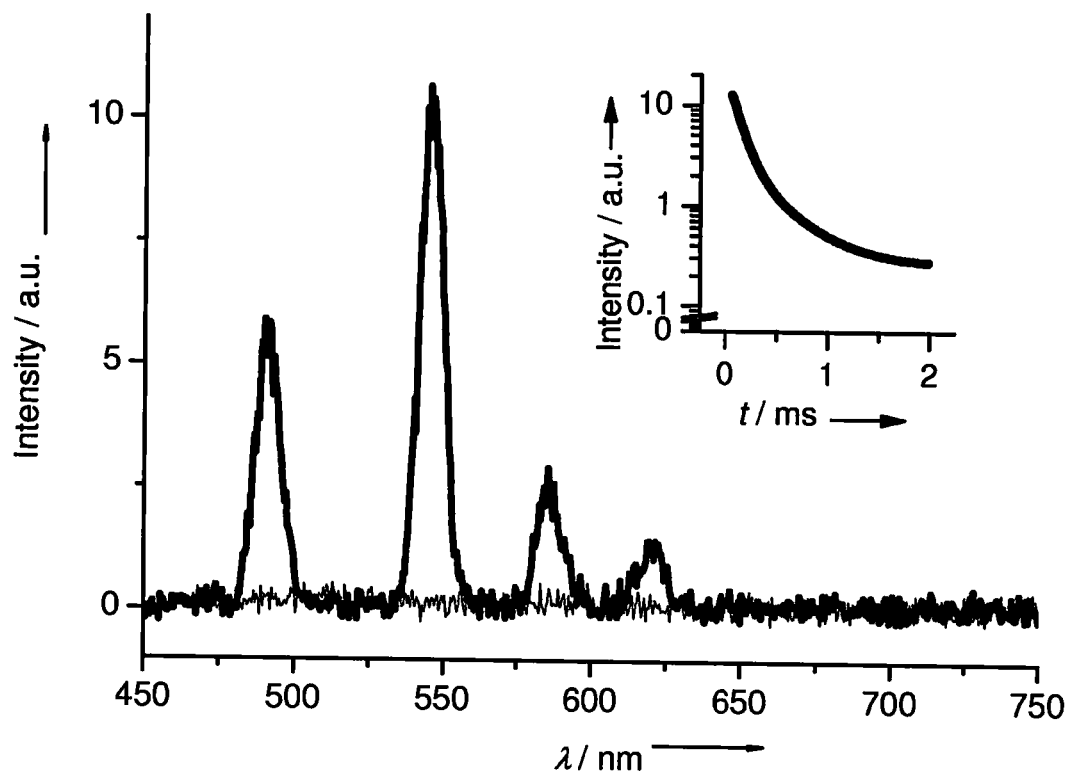
FIG. 16 shows the fluorescence emission spectrum of oligonucleotide directed complex formed of probe A-$Tb^{3+}$—N1 and probe B-TMP-antenna with 0 nm (dashed line) and 10 nM (thick solid line) target oligonucleotide obtained in Example 7. The fitted emission decay spectrum of the complex formed of probe A-$Eu^{3+}$—N1 and probe B-3d-antenna with 10 nm target oligonucleotide is presented in figure insert.

The complex that formed in the presence of target oligonucleotide (FIG. 16; thick line) from probe A-$Tb^{3+}$—N1 and probe B-TMP-antenna generated fluorescence spectrum with the main emission peak at 545 nm. In the absence of the target oligonucleotide (thin line), no fluorescence emission with probe A-$Tb^{3+}$—N1 and probe B-TMP-antenna was detected. The fluorescence decay time of the complex formed of probe A-$Tb^{3+}$—N1 and probe B-TMP-antenna in the presence of 10 nM target oligonucleotide was measured. The lifetime of the emission (see decay spectrum in FIG. 16 inset) was found double exponential; the shorter component had a lifetime of 105 µs and the longer component 400 µs. This indicates that the coupling linkers (affecting the distance and orientation of label moieties) have to be optimized for e.g. different antenna ligands as their structural dimensions vary affecting the efficiency of the chelate complementation directed by biomolecular recognition events.

Example 8

Oligonucleotide Directed Chelate Complementation Assay (OCCA)

Figure 8:
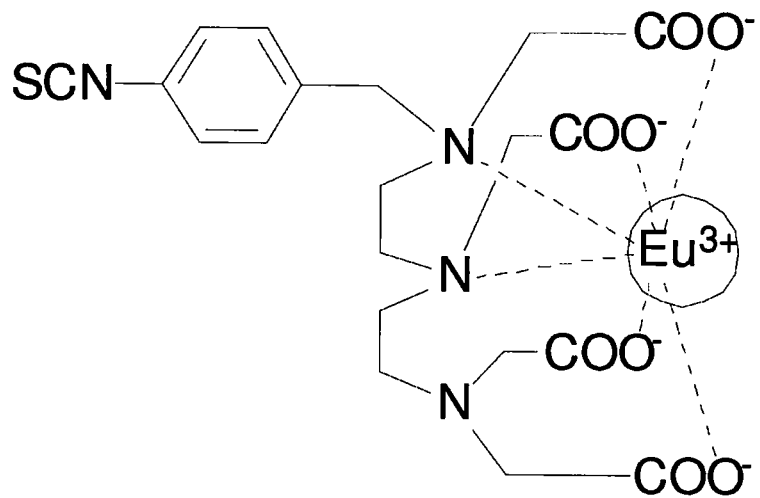
FIG. 8 shows schematic structures of a) europium(III) carrier chelate $N^1$-(4-iso-thiocyanatobenzyl)diethylenetriamine-$N^1,N^2,N^3,N^3$-tetrakis(acetato)europium(III) ($Eu^{3+}$—N1; ion carrier chelate) and b) light-harvesting antenna ligand 4-((isothio-cyanatophenyl)ethynyl)pyridine-2,6-dicarboxylic acid (3d-antenna) employed in Examples 1, 2, 3, 4 and 5; intrinsically fluorescent c) europium(III) chelate {2,2',2'',2'''-{[4-[(4-isothiocyanatophenyl)ethynyl]pyridine-2,6-diyl]-bis(methylene-nitrilo)}tetrakis(acetato)}europium(III) ($Eu^{3+}$-7d; fluorescent lanthanide chelate) employed in Example 2 and d) europium(III) carrier chelate, europium(III) chelate of 2,2'2''-(10-(3-isothiocyanatobenzyl)-1,4,7,10-tetraazacyclododecane-1,4,7-triyl)-triacetic acid employed in Example 8.
Figure 8:
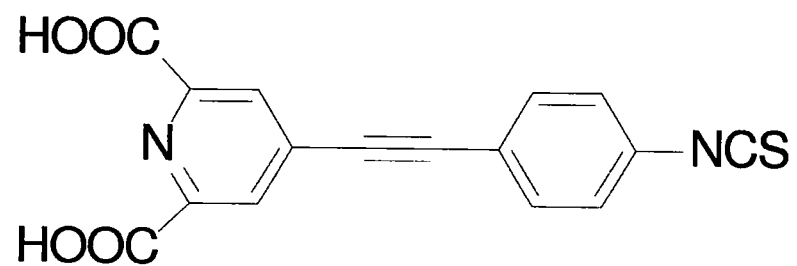
Figure 8:
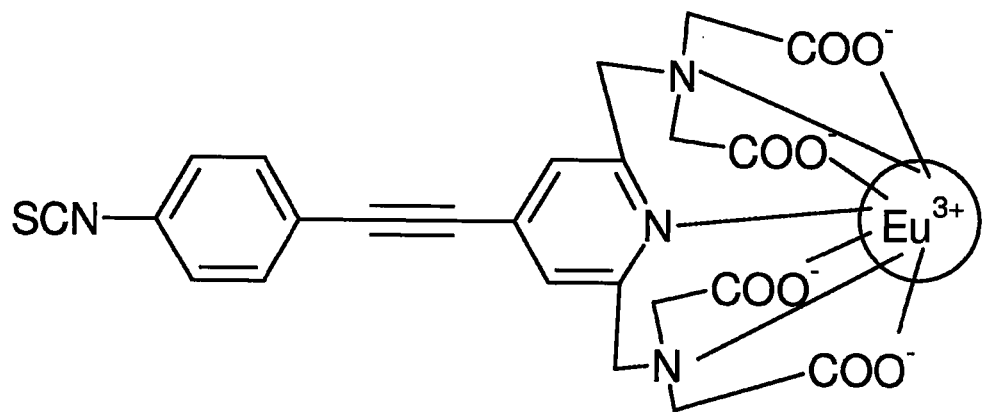
Figure 8:
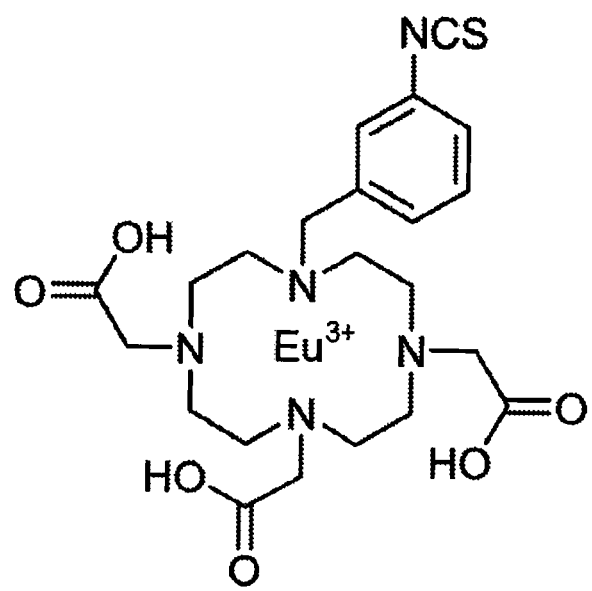

The performance of the detection technology was studied in closed tube real-time PCR by amplifying 0-$10^5$ molecules of synthetic template (5' CTTCAGCGCTACACACGCT-CAAATCATCGAGGAAAACCGTATGAGAAAC-GGATCTAAGCTTGT-CATTTGATAAAGCATCATG-CAACATTAACCCGAGATACGATTTGTCCATATCTT TGATACGACGCCGCAAAAGCTCTTC-CCAAGCCGAGTCTACAG3'; SEQ ID NO: 7; Thermo Scientific, USA). Real-time PCR was performed by using 96-well PCR plate (Thermo-Fast® 96 Robotic PCR Plate, Thermo Scientific) closed with optical caps (MicroAmp®, Optical 8-Cap strip, Applied Biosystems, USA). Each 40 µl PCR reaction contained 500 nM primers (5' primer 5' CTG-TAGACTCGGCTTGGGAAGAGC3', SEQ ID NO: 8 and 3' primer 5' AAGCCTTCCCTTTATACGCTCAAGC3', SEQ ID NO: 9; Thermo Scientific), 50 nM Probe A (5' AATCG-TATCTCGGGTTAATG[AmC7]; SEQ ID NO: 10; Thermo Scientific) labelled with non-luminescent $Eu^{3+}$ ion carrier chelate of (2,2'2''-(10-(3-isothiocyanatobenzyl)-1,4,7,10-tetraazacyclododecane-1,4,7-triyl)triacetic acid; FIG. 8*d*), 50 nM Probe B (5' T(AmC2dT)GCATGATGCTTTATCAAA 3' with 3' phosphate; SEQ ID NO: 11; Thermo Scientific)) labelled with light harvesting antenna-ligand (4-((4-isothiocyanatophenyl)ethynyl)pyri-dine-2,6-dicarboxylic acid) [U. Karhunen et al., Anal Chem, 82 (2010) 751], 30 μM DTPA, 400 μM dNTPs, 0.6 μl Phire Hot Start DNA Polymerase (Finnzymes, Finland), Phire Reaction Buffer (Finnzymes) and variable amount of synthetic single stranded oligonucleotide template. The thermal cycling consisted of a 2 min initial denaturation and polymerase activation step at 98° C. followed by 8 cycles of 15 s at 98° C., 20 s at 60° C. and 15 s at 72° C.; 17 cycles of 15 s at 98° C., 20 s at 60° C., 15 s at 72° C., 15 s at 98° C., 20 s 60° C., 15 s at 72° C., 15 s at 94° C. and 30 s at 30° C. The thermal cycling was performed using PTC-200 thermal cycler (MJ Research, USA) and time resolved fluorescence was measured at 30° C. starting at cycle 9 with Victor 1420 Multilabel counter (Perkin Elmer life science, Finland) by using a 340 nm excitation filter, 615 nm emission filter, 400 μs delay and 400 μs measurement time, and counting 1000 measurement cycles. For each fluorescence measurement the PCR plate was moved temporarily from PTC-200 thermal cycler to Victor 1420 Multilabel counter.

Figure 17:
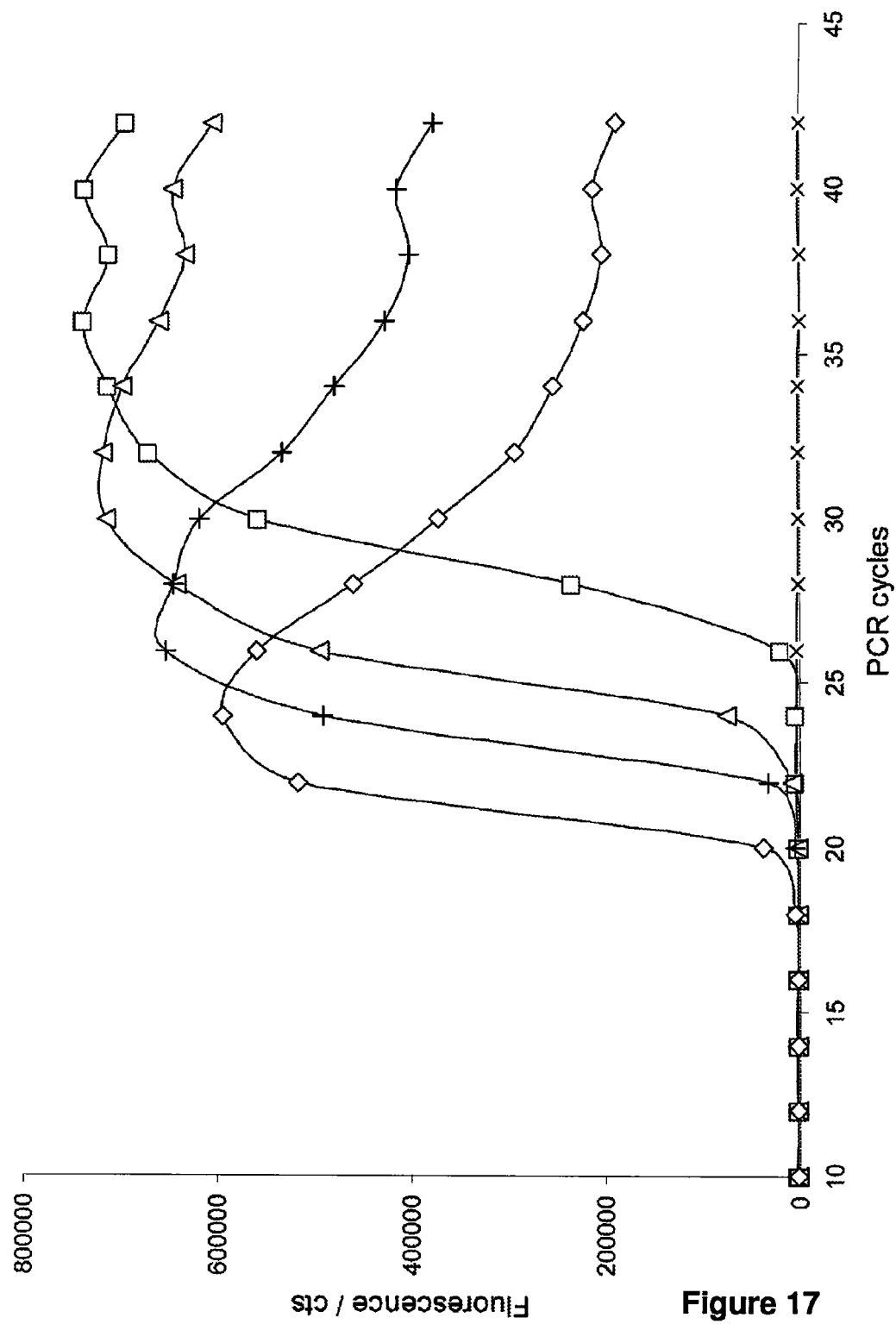
FIG. 17 presents results from the oligonucleotide directed chelate complementation assay (OCCA) described in Example 8. Amplification and detection of 100000 (◇), 10000 (+), 1000 (Δ), 100 (□) and 0 (x) template molecules. Graph shows fluorescence signal measured every second PCR cycle starting at the cycle 10.

Varying amounts of oligonucleotide template was amplified and measured in real-time PCR. The $Eu^{3+}$ specific fluorescence after hybridization of probe A and probe B with the target oligonucleotide is presented in FIG. 17. Amplification plots were generated by plotting the each fluorescence measurement as a function of the PCR cycle number.

Other Preferred Embodiments

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

The invention claimed is:

1. A bioassay method for detecting and/or quantitating an analyte comprising contacting said analyte with a first group and a second group, said first group comprising a non-luminescent lanthanide ion carrier chelate covalently linked to a first recognition element specific for said analyte, wherein said non-luminescent lanthanide ion carrier chelate comprises a lanthanide ion carrier ligand bound a lanthanide ion and said second group comprising an antenna ligand covalently linked to a second recognition element specific for said analyte;

wherein said lanthanide ion carrier chelate is an ionic macrocyclic chelate structure selected from the group consisting of pentadentate, hexadentate, heptadentate and octadentate;

wherein said antenna ligand binds to said lanthanide ion and the antenna ligand is either monodentate, bidentate, tridentate or tetradentate, and the combination of ion carrier chelate and antenna ligand is selected so that the sum total of ligand coordination sites is nine or ten; and recognizing said analyte by said first recognition element of said first group and by said second recognition element of said second group, such that chelate complementation by formation of a mixed lanthanide chelate complex through complementation of said non-luminescent lanthanide ion carrier chelate carrying said lanthanide ion with said antenna ligand occurs that results in increased fluorescence.

2. The bioassay according to claim 1 wherein the ionic macrocyclic chelate structure is selected from the group consisting of structures f, q, h, i, j, k, l, m and n below, wherein X is a reactive group;
A is a linker or spacer group;
Ln is a trivalent lanthanide ion;

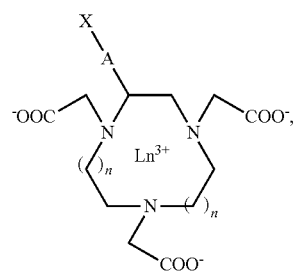
f)

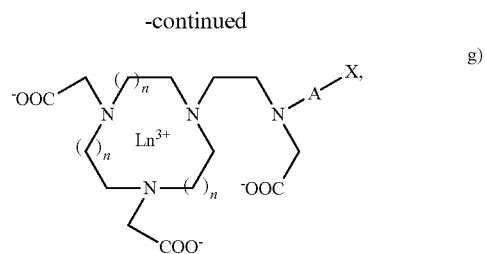
g)

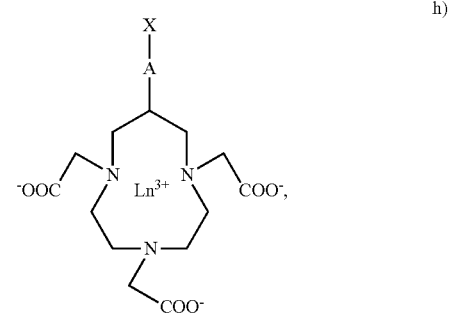
h)

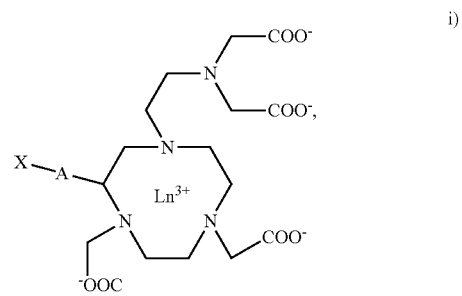
i)

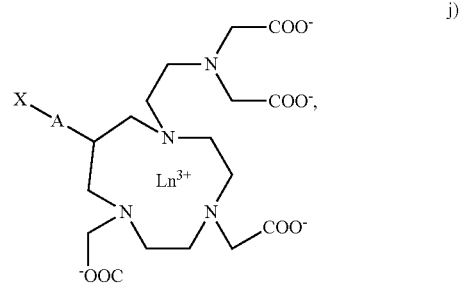
j)

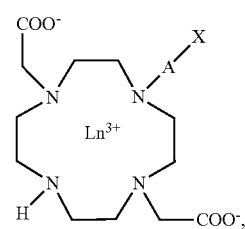
k)

l)
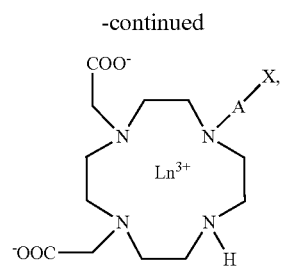

m)
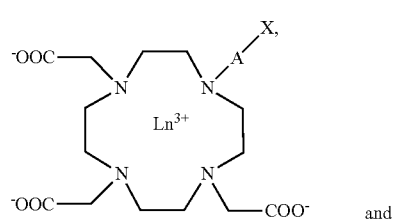
and n)
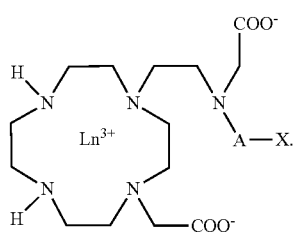

3. The bioassay according to claim 1, wherein an agent complexing said lanthanide ion at a concentration of at least 1 pmol/l is added to a solution containing said analyte, wherein said agent is selected from the group consisting of CDTA, EDTA, DOTA, DTPA, EGTA, HEED, HEDTA, NOTA, NTA, TETA and TTHA.

4. The bioassay according to claim 1, wherein the lanthanide ion of the ion carrier chelate is selected from the group consisting of praseodymium(III), neodymium(III), samarium(III), europium(III), terbium(III), dysprosium(III), holmium(III), erbium(III), thulium(III) and ytterbium(III).

5. The bioassay according to claim 1 wherein the first and second recognition elements are independently of each other selected from the group consisting of oligonucleotides, aptamers, peptides, proteins, haptens and oligosaccharides.

6. The bioassay according to claim 3, wherein said complexing agent is a stronger binder of said lanthanide ion than the antenna ligand, so that log $K_{LnL3}$>log $K_{LnL4}$, wherein $K_{LnL4}$ refers to stability constant of the complex between said antenna ligand and said lanthanide ion in solution.

7. The bioassay according to claim 1 wherein said fluorescence is measured at a wavelength between 400 and 1600 nm.

8. The bioassay according to claim 1 wherein the analyte detected and/or quantified is selected from the group consisting of streptavidin, protein, hapten, nucleic acid sequence, cells, viruses, product of nucleic acid amplification reactions and product of polymerase chain reaction.

9. The bioassay according to claim 1 wherein said fluorescence has a fluorescence lifetime of >1 μs.

10. The bioassay according to claim 1 wherein said fluorescence is upconversion fluorescence wherein emission is detected at a shorter wavelength than excitation.

11. The bioassay according to claim 3, wherein
    i) log $K_{LnL2}$ is at least 12, wherein $K_{LnL2}$ refers to the stability constant of the complex between the ion carrier ligand and the lanthanide ion in solution; and
    ii) log $K_{LnL3}$ is at least 8, wherein $K_{LnL3}$ refers to a stability constant between said complexing agent complexing said lanthanide ion and the lanthanide ion in solution.

12. The bioassay according to claim 6, wherein said complexing agent is a weaker binder of the lanthanide ion than the ion carrier chelate, so that log $K_{LnL4}$<log $K_{LnL2}$.

13. A bioassay method for detecting and/or quantitating an fluorescent mixed lanthanide chelate complex analyte, comprising
    providing a fluorescent mixed lanthanide chelate complex comprising a lanthanide ion carrier chelate and an antenna ligand,
        wherein said lanthanide ion carrier chelate is non-luminescent and comprises a lanthanide ion bound to an ionic macrocyclic chelate structure selected from the group consisting of pentadentate, hexadentate, heptadentate and octadentate,
        wherein said antenna ligand is either monodentate, bidentate, tridentate or tetradentate, and the combination of ion carrier chelate and antenna ligand is selected so that the sum total of ligand coordination sites is nine or ten,
        wherein at least one of said lanthanide ion carrier chelate and said antenna ligand is covalently attached to an analyte-specific recognition element,
    contacting said fluorescent mixed lanthanide chelate complex with an analyte such that discomplementation of said fluorescent mixed lanthanide chelate complex occurs by separation of said lanthanide ion carrier chelate from said antenna ligand, thereby resulting in decreased fluorescence.

14. The bioassay according to claim 1, wherein the antenna ligand is selected from the group consisting of structures a, b, c, d, e, i, j, w, x, y and z below, wherein
    X is a reactive group,
    A is a linker or spacer group,
    G is —$CF_3$, —$CF_2CF_3$ or —$CF_2CF_2CF_3$, a)
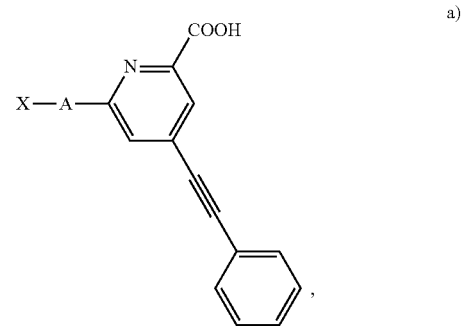

-continued
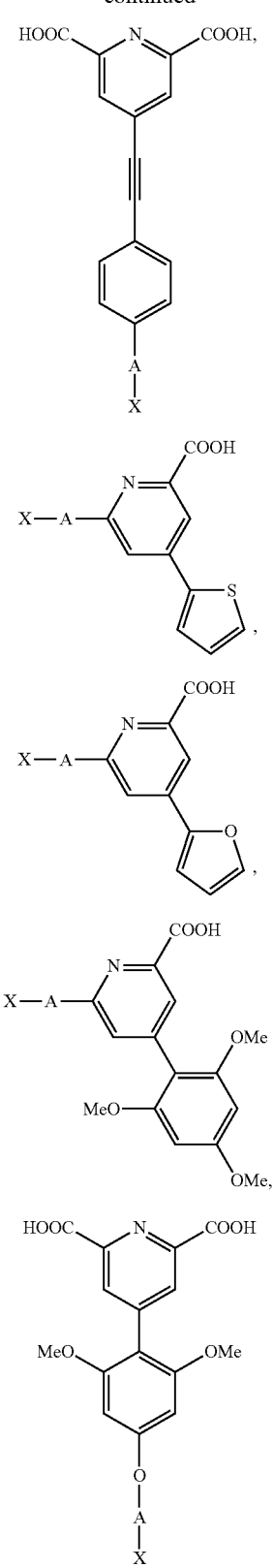
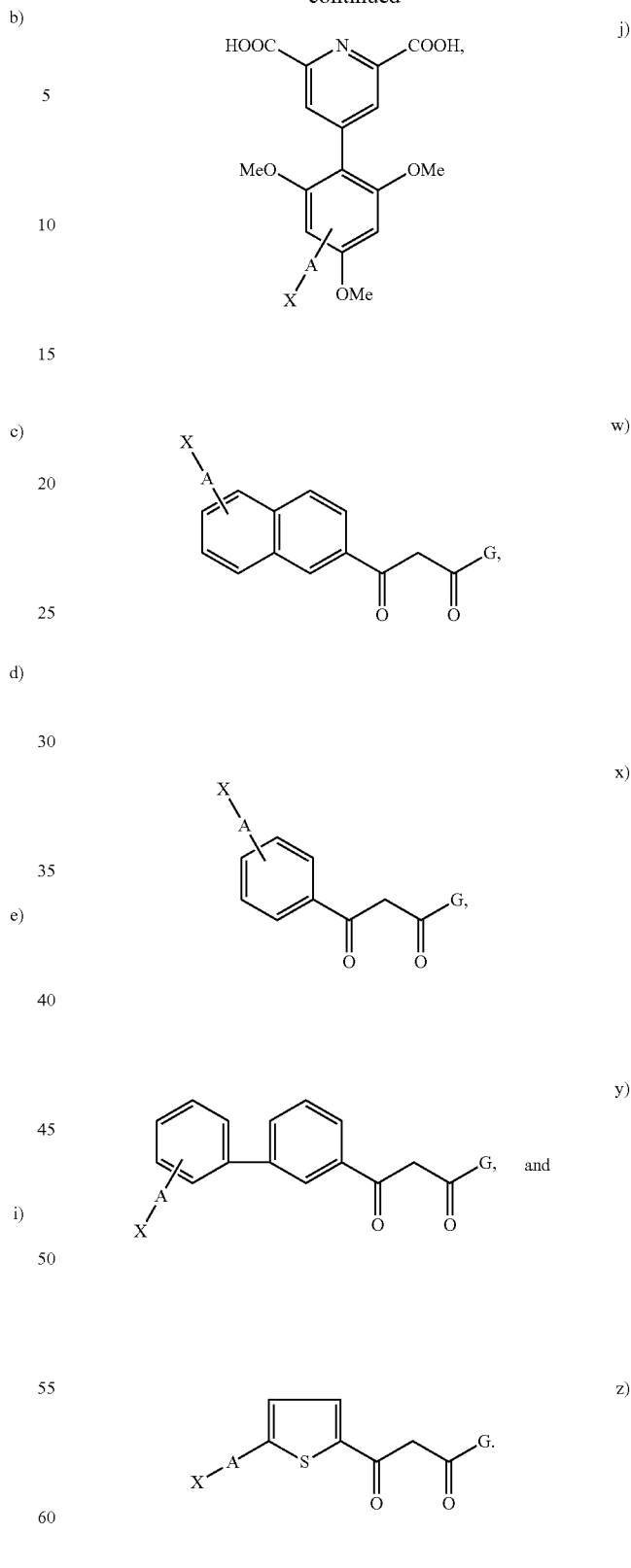
* * * * *